(12) United States Patent
Montgomery et al.

(10) Patent No.: US 7,678,329 B2
(45) Date of Patent: Mar. 16, 2010

(54) NO$_x$ SENSING DEVICES HAVING CONDUCTIVE OXIDE ELECTRODES

(75) Inventors: Frederick C. Montgomery, Oak Ridge, TN (US); David L. West, Oak Ridge, TN (US); Timothy R. Armstrong, Clinton, TN (US); Lonnie C. Maxey, Powell, TN (US)

(73) Assignee: Babcock & Wilcox Technical Services Y-12, LLC, Oak Ridge, TN (US)

( * ) Notice: Subject to any disclaimer, the term of this patent is extended or adjusted under 35 U.S.C. 154(b) by 847 days.

(21) Appl. No.: 10/949,854

(22) Filed: Sep. 24, 2004

(65) Prior Publication Data

US 2006/0073070 A1    Apr. 6, 2006

(51) Int. Cl.
*G01N 21/76*    (2006.01)
(52) U.S. Cl. ............................................. 422/52
(58) Field of Classification Search .................. 422/52
See application file for complete search history.

(56) References Cited

U.S. PATENT DOCUMENTS

| | | | |
|---|---|---|---|
| 4,462,890 A | | 7/1984 | Touda et al. |
| 5,217,588 A | * | 6/1993 | Wang et al. .................. 205/781 |
| 5,397,442 A | | 3/1995 | Wachsman |
| 5,643,429 A | * | 7/1997 | Wachsman .................. 205/781 |
| 5,736,028 A | | 4/1998 | Hjortsberg et al. |
| 6,019,881 A | * | 2/2000 | Kurosawa et al. ........... 204/424 |
| 6,051,123 A | | 4/2000 | Joshi et al. |
| 2004/0104114 A1 | | 6/2004 | Schulte et al. |

FOREIGN PATENT DOCUMENTS

GB    2 087 569    5/1982

OTHER PUBLICATIONS

Email Correspondences of Dec. 9 & 15, 2009 and draft of amended claims.*
N. Kato, et al., "Thick Film ZrO2 Sensor for the Measurement of Low NOx Concentraitons," SAE Technical Paper Series, 1998, vol. 980170.
A. Kunimoto, et al., "New Total-NOx Sensor Based on Mixed Potential for Automobiles," SAE Technical Paper, 1999, vol. 1999-01-1280.
F. Menil, et al., "Critical Review of Nitrogen Monoxide Sensors for Exhaust Gases of Lean Burn Gasoline Engines," Sensors and Actuators B, 2000, pp. 1-23, vol. 67.
W. Gopel, et al., "Trends in the Development of Solid State Amperometric and Potentiometrick High Temperature Sensors," Solid State Ionics, 2000, pp. 519-531, vol. 136-137.

(Continued)

*Primary Examiner*—Walter D Griffin
*Assistant Examiner*—Bobby Ramdhanie
(74) *Attorney, Agent, or Firm*—Michael J. Renner; Luedeka, Neely & Graham, P.C.

(57) ABSTRACT

A NO$_x$ sensing device includes at least one pair of spaced electrodes, at least one of which is made of a conductive oxide, and an oxygen-ion conducting material in bridging electrical communication with the electrodes.

29 Claims, 42 Drawing Sheets

OTHER PUBLICATIONS

N. Docquier and S. Candel, "Combustion Control and Sensors: A Review," Progress in Energy and Combustion Science, 2002, pp. 107-150, vol. 28.

N. Miura, et al., "Progress in Mixed-Potential Type Devices Based on Solid Electrolyte for Sensing Redox Gases," Solid State Ionics, 2000, pp. 533-542, vol. 136-137.

V. Coillard, et al., "Nitrogen Minoxide Detection with a Planar Spinel Coated Amperometric Sensor," Sensors and Acuators B, 2001, pp. 113-118, vol. 78.

K-Y. Ho, et al., "NOx Response Properties in DC Current of Nd2CuO4/4YSZ/Pt Element," Jouranl of the Ceramic Society of Japan, 1996, pp. 995-999, vol. 104.

M. L. Grilli, et al., "Electrochemical NOx Sensors Based on Interfacing Nanosized LaFeO3 Perovskite-Type Oxide & Ionic . . . ," J of Electrocheml Soc, 2001, pp. H98-H102, vol. 148.

N. Miura, et al., "Impedancemetric Gas Sensor Based on Zirconia Solid Electrolyte & Oxide Sensing Electrode . . . ," Sensors & Actuators B, 2003, pp. 221-228, vol. 93.

Miura N. et al., "High-Temperature Potentiometric/Amperometric NOx Sensors Combining Stabilized Zirconia with . . . ," Sensors and Actuators B, 1998, pp. 169-178, vol. 52, No. 1-2.

D.L. West et al., Electrode Material for Mixed-Potent NOx . . . , Database Inspec 'Online! Inst of Elect Engrs, Stevenage, GB, 2004, DBase acc. No. 8404719, vol. 25, No. 3.

D.L. West et al., Electrode Mat. for Mixed . . . , Dbase Inspec 'Online! Inst of Elect Engrs, Stevenage, GB, 2004, DBase acc. No. 8404719, Abstract & pp. 494-495, vol. 25, No. 3.

D.L. West et al., "Electrically Biased NOx Sensing Elements with Co-Planar . . . ," Database Compendex 'Online! Engr Info, Inc. Asscesion No. E2005229135824, vol. 152, No. 6.

D.L. West et al., "Electrically Biased NOx Sensing Elementsr . . . ," Database Compendex 'Online! Engr Info, Inc. Asscesion No. E2005229135824, Abstract pp. 914, vol. 152, No. 6.

D.L. West, et al., "Electrically Biased NOx Sensing elements with Coplanar Electrodes," Journal of the Electrochemical Society, 2005, pp. H74-H79, vol. 152, No. 6.

D.L. West, et al., "Use of La0.85Sr0.15CrO3 in High-Temperature NOx Sensing Elements," Sensors and Actuators B, 2005, pp. 758-765, vol. 106, No. 2.

J.W. Yoon et al., "The NO2 Response of Solid Electrolyte Sensors Made Using Nano-Sized LaFe03 Electrodes," Sensors and Actuators B, 2001, pp. 483-488, vol. 76, No. 1-3.

\* cited by examiner

$NO_x$ SENSING DEVICES HAVING CONDUCTIVE OXIDE ELECTRODES

The United States Government has rights in this invention pursuant to contract no. DE-AC05-00OR22725 between the United States Department of Energy and UT-Battelle, LLC.

FIELD OF THE INVENTION

The present invention relates to $NO_x$ sensing devices, and more particularly to $NO_x$ sensing devices that are fabricated with coplanar electrodes.

BACKGROUND OF THE INVENTION

Pollutants in combustion exhausts from low-sulfur fuels are generally comprised of carbon monoxide (CO), hydrocarbons (HC), and oxides of nitrogen ("$NO_x$", which generally comprises a mixture of NO and $NO_2$). Currently, for spark-ignited, fuel-injected passenger car engines, a three-way catalyst (TWC) is employed that greatly reduces the levels of all three of these pollutants. The TWC is only effective within a narrow range of oxygen ($O_2$) concentrations in the exhaust, losing its effectiveness for $NO_x$ removal at higher $O_2$ contents. Therefore the TWC cannot generally be employed for $NO_x$ remediation of exhausts from diesel and lean-burn gasoline engines, which tend to be $O_2$-rich.

Engines that produce $O_2$-rich exhausts require on-board $NO_x$ remediation with techniques such as selective catalytic reduction (SCR) with reagent (HC and/or urea) injection. The amount of reagent injection during SCR is critical, as enough must be supplied to completely decompose the $NO_x$, but the addition of excess must be avoided. Therefore, it is essential to develop sensors that can rapidly and accurately assess the $NO_x$ levels in these exhausts and enable improved emissions control and on-board diagnostics. $NO_x$ sensors suitable for these applications should be compact, robust, low-cost, capable of operating at temperatures near 600-700° C., and able to measure $NO_x$ in the concentration range $\sim 0$ $ppm_V \leq [NO_x] \leq 1500$ $ppm_V$ at $O_2$ levels varying between 5 and 20%.

OBJECTS OF THE INVENTION

Accordingly, objects of the present invention include the provision of compact, robust, low-cost $NO_x$ sensors that are capable of operating at temperatures near 600-700° C., and are able to measure $NO_x$ in the concentration range $\sim 0$ $ppm_V \leq [NO_x] \leq 1500$ $ppm_V$ at $O_2$ levels varying between 5 and 20%. Further and other objects of the present invention will become apparent from the description contained herein.

SUMMARY OF THE INVENTION

In accordance with one aspect of the present invention, the foregoing and other objects are achieved by a $NO_x$ sensing device comprising a conductive oxide that forms at least one pair of spaced electrodes, and an oxygen-ion conducting material in bridging electrical communication with said pair of spaced electrodes, said device being configured to sense at least one chemical selected from the group consisting of NO and $NO_2$.

In accordance with another aspect of the present invention, a $NO_x$ sensing device comprising a first electrode comprised of a conductive oxide, a second electrode consisting essentially of a conductive material, and an oxygen-ion conducting material in bridging electrical communication with said first electrode and said second electrode, said device being configured to sense at least one chemical selected from the group consisting of NO and $NO_2$.

BRIEF DESCRIPTION OF THE DRAWINGS

In the figs., elements that are essentially the same are called out with the same numerals.

FIG. 1b is a view through A-A' of FIG. 1a.

FIG. 5b is a view through B-B' of FIG. 5a.

FIG. 6b is a view through C-C' of FIG. 6a.

FIG. 7b is a view through D-D' of FIG. 7a.

FIG. 8b is a view through E-E' of FIG. 8a.

For a better understanding of the present invention, together with other and further objects, advantages and capabilities thereof, reference is made to the following disclosure and appended claims in connection with the above-described drawings.

DETAILED DESCRIPTION OF THE INVENTION

Figure 1A:
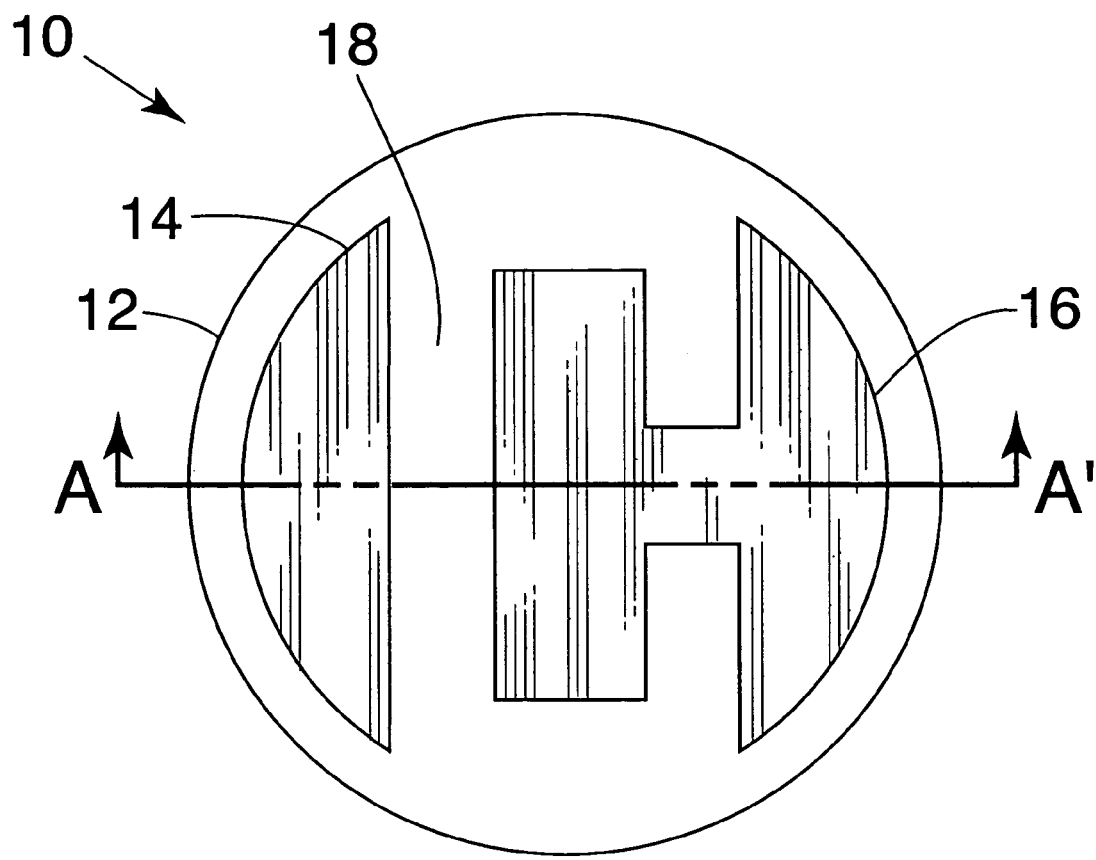
FIG. 1a is a schematic, not-to-scale, top view of a sensing element in accordance with an embodiment of the present invention.
Figure 1B:
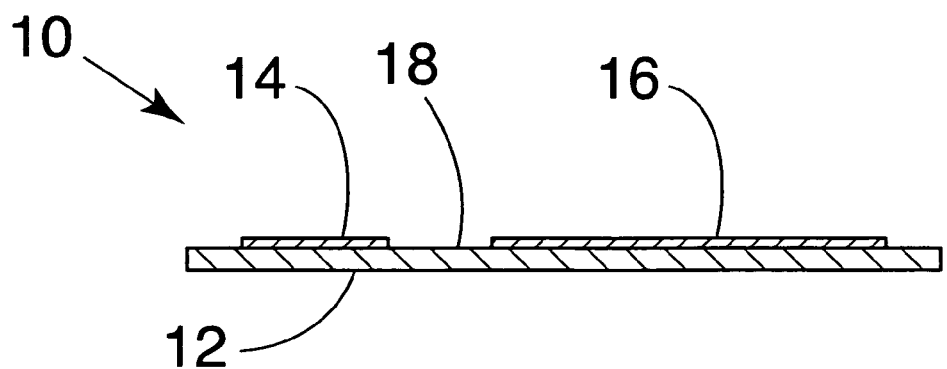

Referring to FIGS. 1a and 1b, a $NO_x$ sensing device 10 in accordance with some embodiments of the present invention generally comprises an oxygen-ion conducting substrate 12 (for example, yttria-stabilized zirconia, "YSZ"). A pair of co-planar electrodes 14, 16 is in layer form; the electrodes 14, 16 are separated by a gap 18. The electrodes 14, 16 are essentially identical in composition.

A suitable oxygen-ion conducting substrate 12 can be produced by tape-casting and sintering commercially obtained YSZ. Other suitable oxygen-ion conducting substrate materials include, but are not limited to $M'_xZr_{1-x}O_{2-\delta}$, and $M''_xCe_{1-x}O_{2-\delta}$, where M' and M'' are additives intended to induce oxygen conduction, and $La_{1-y}M'''_yGa_{1-z}M''''_zO_{3-\delta}$, where M''' and M'''' are additives that induce oxygen ion conduction and/or stabilize a perovskite phase. Examples of suitable oxygen-ion conducting substrate materials include, but are not limited to:

$Y_{1-a}Zr_aO_{2-\delta}$, $Sc_{1-a}Zr_aO_{2-\delta}$, $Ca_{1-a}Zr_aO_{2-\delta}$, $Mg_{1-a}Zr_aO_{2-\delta}$, $Gd_{1-b}Ce_bO_{2-\delta}$, $La_{1-b}Ce_bO_{2-\delta}$, $Yb_{1-b}Ce_bO_{2-\delta}$, $La_{2-b}Sr_bMo_2O_9$, $La_{2-b}Ba_bMo_2O_9$, $La_{1-b}Sr_bGa_{1-c}Mg_cO_{3-\delta}$, $La_{1-b}Sr_bGa_{1-a-d}Mg_aNi_dO_{3-\delta}$, $La_{1-b}Sr_bGa_{1-a-d}Mg_aCo_dO_{3-\delta}$, $La_{1-b}Sr_bGa_{1-a-d}Mg_aFe_dO_{3-\delta}$, $La_2MO_{2-e}Nb_eO_9$, $La_2Mo_{2-e}Ta_eO_9$, and $La_2Mo_{2-e}W_eO_9$, where $0<a<0.2$, $0<b<0.3$, $0<c<0.3$, $a+d<0.3$, and $0<e<1$.

Other methods of production thereof include, but are not limited to dry pressing, roll compaction, injection molding, etc. followed by appropriate heat or other treatments to remove processing aids and densify the substrate. Typically, the substrate can be of a thickness in the range of about 0.02 cm to about 0.3 cm, although substrate thickness is not considered to be a critical feature of the present invention.

A suitable pair of electrodes 14, 16 can be deposited onto the substrate 12 using any of the various well-known methods of screen-printing a dispersion of electrode material followed by appropriate thermal treatment. Suitable electrode materials include, but are not limited to, either alone or in combination: noble metals such as Pd, Pt, Au, Ag, and Ir, for example; and transition metal oxides such as, for example, $Cr_2O_3$, $NiCr_2O_4$, $Ba_{0.08}Cu_{0.92}Cr_2O_4$, $La_{1-x}A_xCr_yO_3$ (A=Sr, Ca, or Ba, $0.01 \leq x \leq 0.35$, $0.95 \leq y \leq 1.05$), and $La_{1-x}A_xMn_yO_3$ (A=Sr, Ca, or Ba, $0.01 \leq x \leq 0.35$, $0.95 \leq y \leq 1.05$).

In addition to the various constituents cited above, the geometries, as described especially in Examples I-IV below, when biased, have been shown to yield "total-$NO_x$" or "NO-selective" behavior when the oxide employed was $La_{0.8}Sr_{0.2}MnO_3$, $La_{0.75}Sr_{0.25}CrO_3$, $La_{0.75}Sr_{0.25}Mn_{0.5}Cr_{0.50}O_3$, $Cr_2O_3$, $La_2CoNiO_5$, $La_{1.8}Sr_{0.2}CoO_4$, $La_{1.8}Sr_{0.2}NiO_4$, or $NiCr_2O_4$. Therefore, it is expected a very large variety of oxide compositions can be employed in embodiments of the disclosed invention with success. Examples of suitable perovskite oxides include, but are not limited to the following, either alone or in any combination:

$Y_{1-x}A_xM_{1-z}M'_zO_3$, $Ln_{1-y}A_yM_{1-z}M'_zO_3$, where Ln is a Lanthanide (La, Ce, Pr, Nd, Sm, Eu, Gd, Th, Dy, Ho, Er, Tm, Yb, Lu); A is an alkaline-earth metal (Mg, Ca, Sr, Ba); M and M' are transition elements from period 4 (Sc, Ti, V, Cr, Mn, Fe, Co, Ni, Cu, Zn); $0 \leq x \leq 0.4$; $0 \leq y \leq 0.4$; and $0 \leq z \leq 1$.

Dispersions for screen printing can be made using commercially available powders and processing aids; some may be obtained commercially in a form suitable for screen printing. Thickness of the electrodes can be in the range of less than 5 μm to more than 100 μm, although electrode thickness is not considered to be a critical feature of the present invention.

Electrodes can be deposited by any suitable conventional means. Alternate methods of electrode deposition include, but are not limited to sputtering, chemical and physical vapor deposition, spin coating of sol-gel solutions, pulsed laser deposition.

Figure 2:
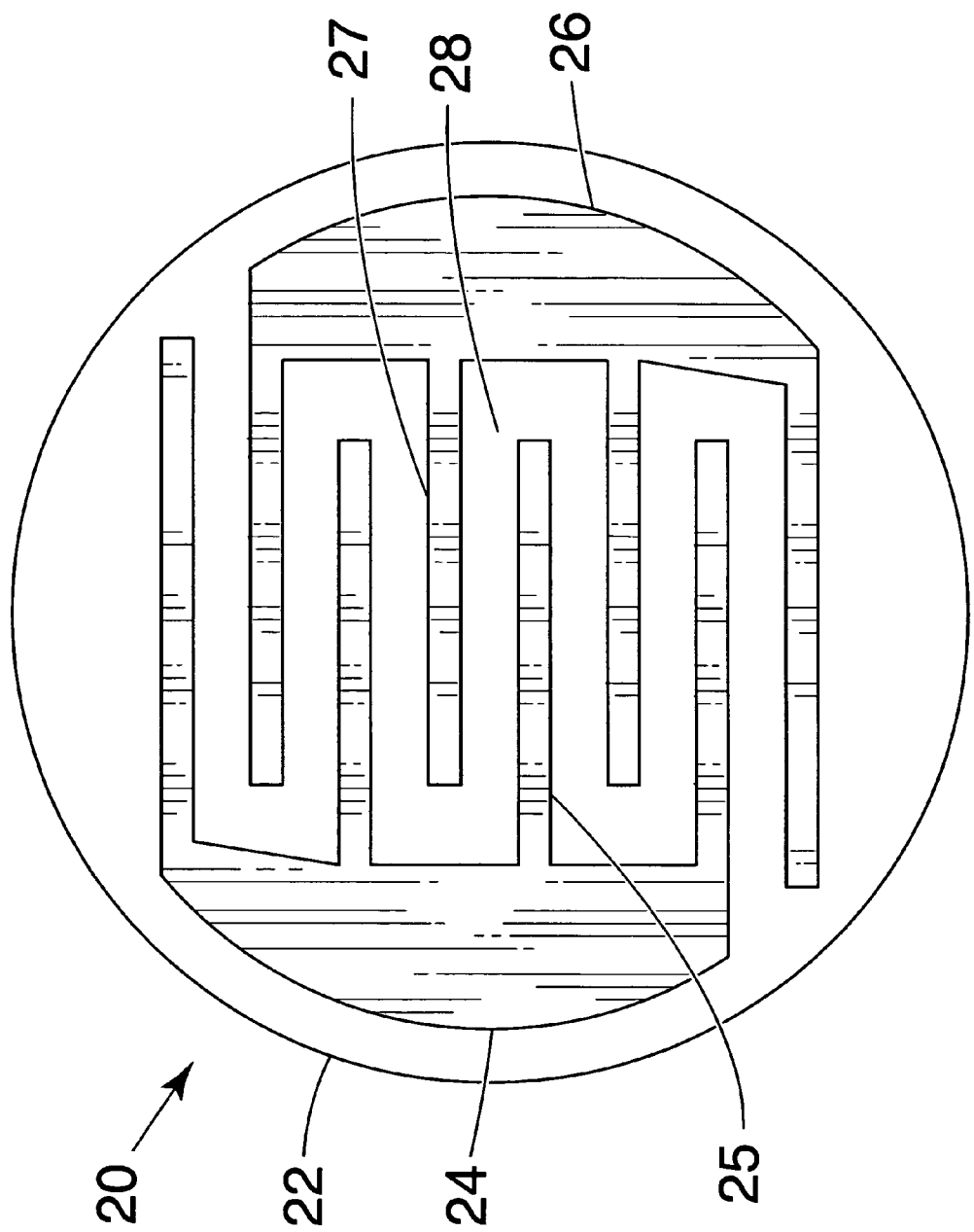
FIG. 2 is a schematic, not-to-scale, top view of a sensing element in accordance with another embodiment of the present invention.

Referring to FIG. 2, a sensing device 20 can be comprised of an oxygen-ion conducting substrate 22 with co-planar, interdigitated electrodes 24, 26. Electrodes 24, 26 are essentially identical in composition, thickness, and area, having respective fingers 25, 27 that define a serpentine gap 28.

Figure 3:
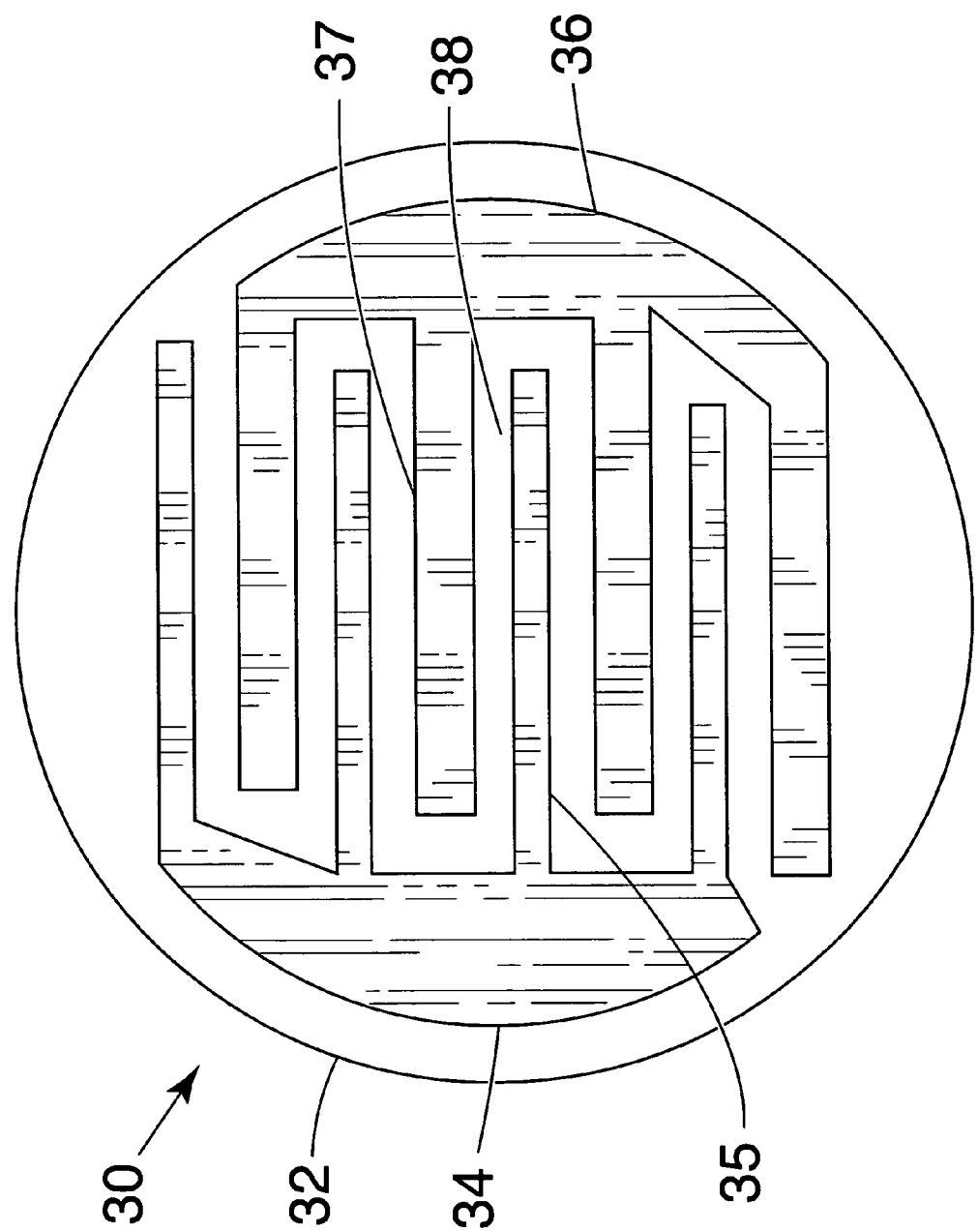
FIG. 3 is a schematic, not-to-scale, top view of a sensing element in accordance with another embodiment of the present invention.

Referring to FIG. 3, a sensing device 30 can be comprised of an oxygen-ion conducting substrate 32 with co-planar, interdigitated electrodes 34, 36. Electrodes 34, 36 are essentially identical in composition and thickness, but different in area, having respective fingers 35, 37 that define a serpentine gap 38. The fingers 37 of one electrode 36 are wider than the fingers 35 of the other electrode 34, increasing the overall area of the one electrode 36.

Figure 4:
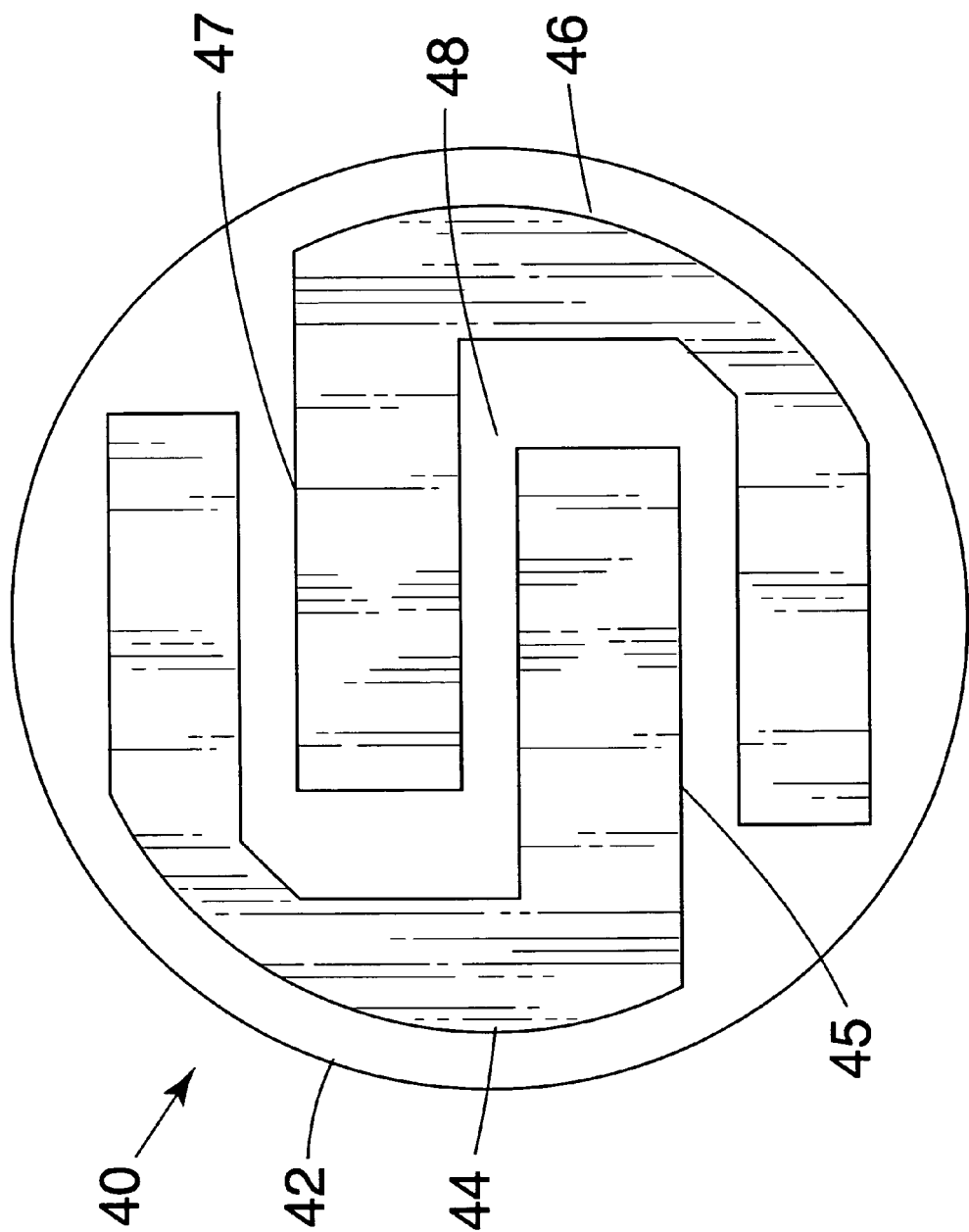
FIG. 4 is a schematic, not-to-scale, top view of a sensing element in accordance with another embodiment of the present invention.

Referring to FIG. 4, a sensing device 40 can be comprised of an oxygen-ion conducting substrate 42 with co-planar, coarsely interdigitated electrodes 44, 46. Electrodes 44, 46 are essentially identical in composition, thickness, and area, having respective fingers 45, 47 that define an s-shaped gap 48.

Figure 5A:
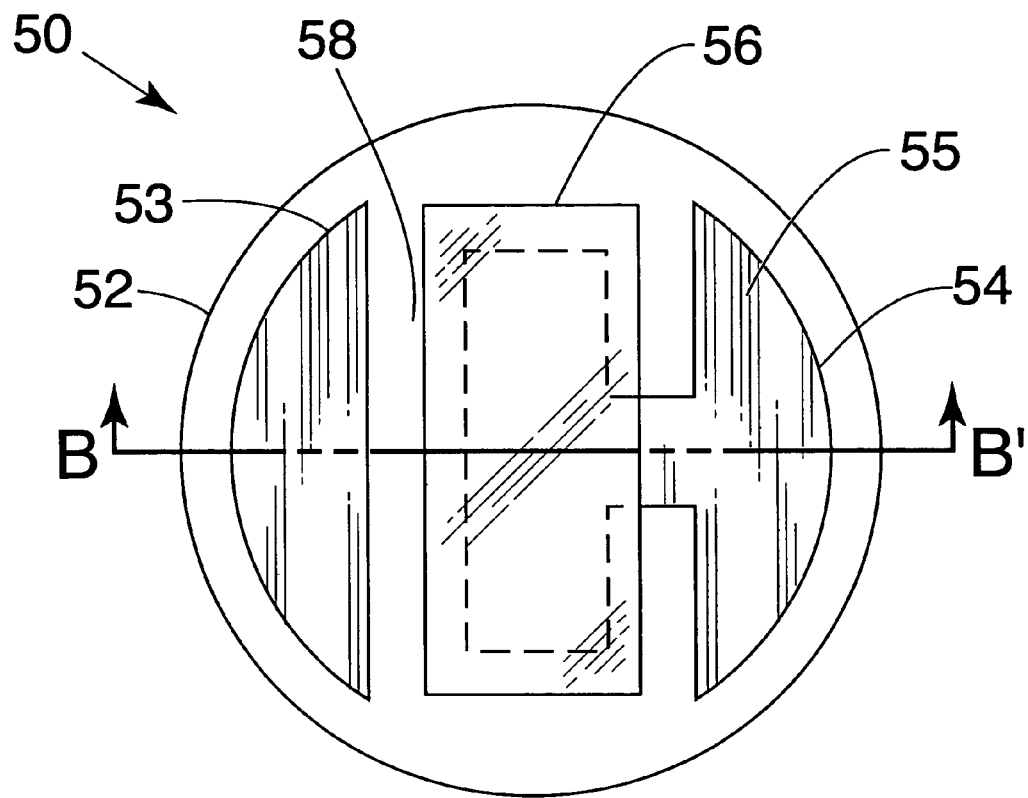
FIG. 5a is a schematic, not-to-scale, top view of a sensing element in accordance with another embodiment of the present invention.
Figure 5B:
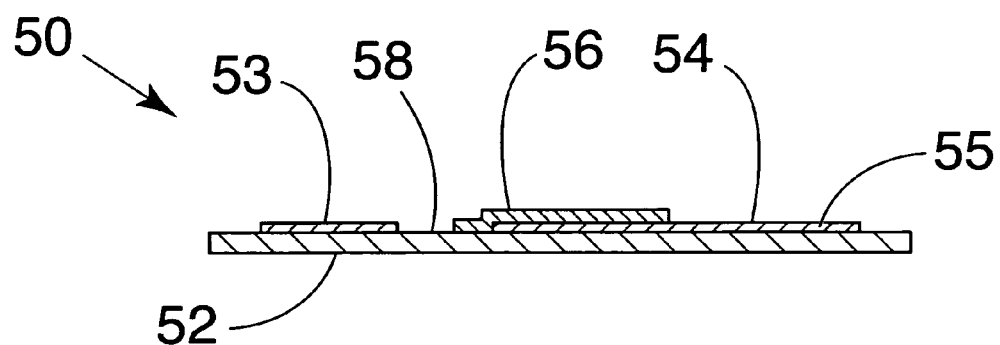

In some embodiments of the invention, the electrodes can be made of a plurality of layers. Referring to FIGS. 5a and 5b, a $NO_x$ sensing device 50 in accordance with some embodiments of the present invention generally comprises an oxygen-ion conducting substrate 52 as described herein. A first, single-layered electrode 53 is deposited directly onto the substrate 52. A second, two-layered electrode 54 comprises a first layer 55 and an overlayer 56. The electrodes 52, 54 are separated by a gap 58. The first layer 55 is an electronically conductive material deposited directly onto the substrate 52, and can be comprised of the same composition as the first electrode 53 or a different composition. The overlayer 56 is deposited over the first layer 55. The overlayer 56 can overlap the first layer 55 as shown, if desired. The overlayer 56 can be, for example, a porous oxide as described herein. Advantages of the overlayer configuration include, but are not limited to: enhanced electrical contact of the overlayer layer 56 with requisite electronic circuitry and the ability to adjust the relative catalytic activity of the two co-planar electrodes.

Figure 6A:
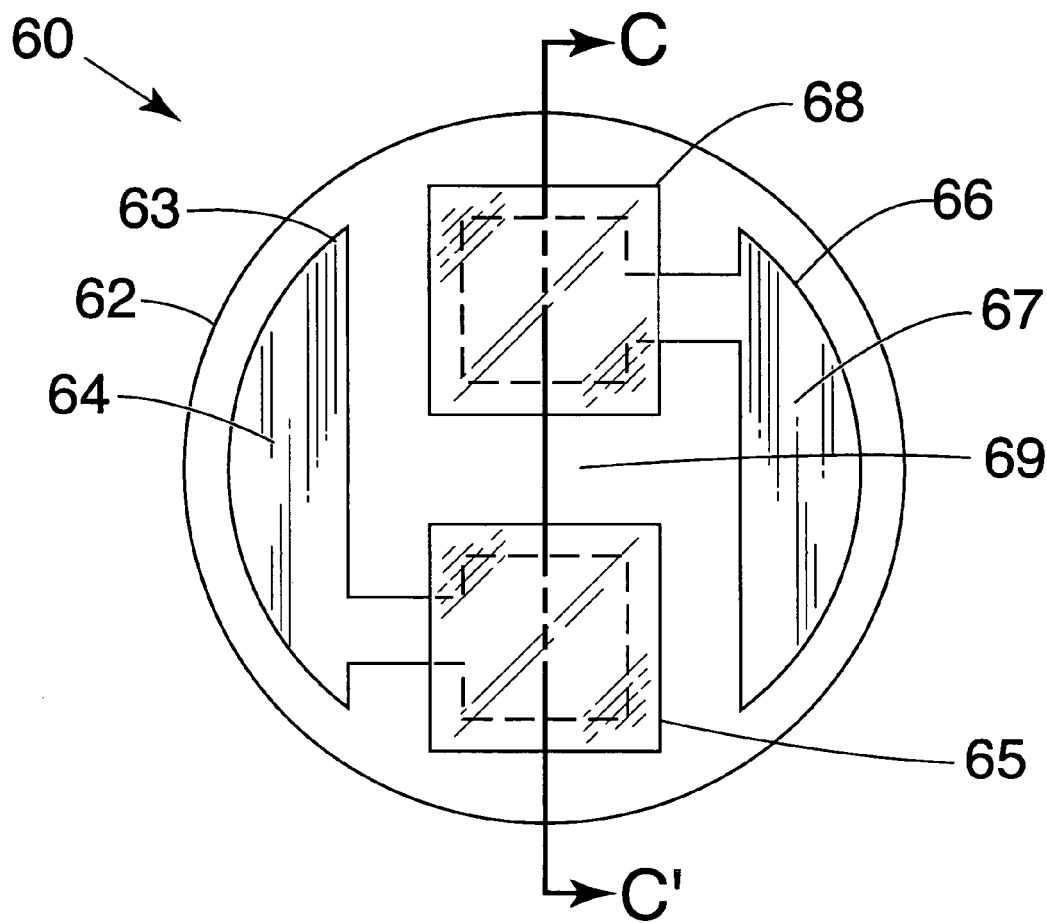
FIG. 6a is a schematic, not-to-scale, top view of a sensing element in accordance with another embodiment of the present invention.
Figure 6B:
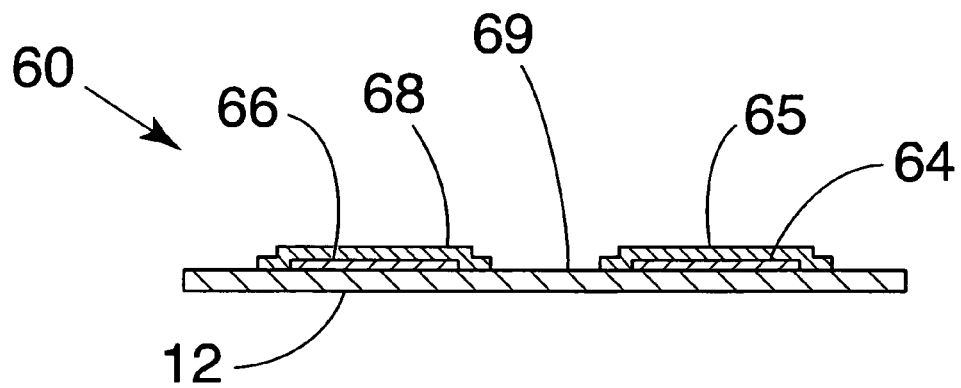

Referring to FIGS. 6a and 6b, a $NO_x$ sensing device 60 in accordance with some embodiments of the present invention generally comprises an oxygen-ion conducting substrate 62. A pair of co-planar electrodes 63, 66 is in layer form, separated by a gap 69. One electrode 63 comprises an electronically conductive material first layer 64 and an optionally overlapping oxide overlayer 65. The other electrode 66 comprises an electronically conductive material first layer 67 and an optionally overlapping oxide overlayer 68. The first layer 64 of one electrode 63 can comprise the same composition as the first layer 67 of the other electrode 66 or it can comprise a different composition. Moreover, the overlayer 65 of one electrode 63 can comprise the same composition as the overlayer 68 of the other electrode 66 or it can comprise a different composition. Advantages of the two-overlayer configuration of FIGS. 6a, 6b include, but are not limited to: the ability to individually adjust the catalytic properties of the two electrodes.

Figure 7A:
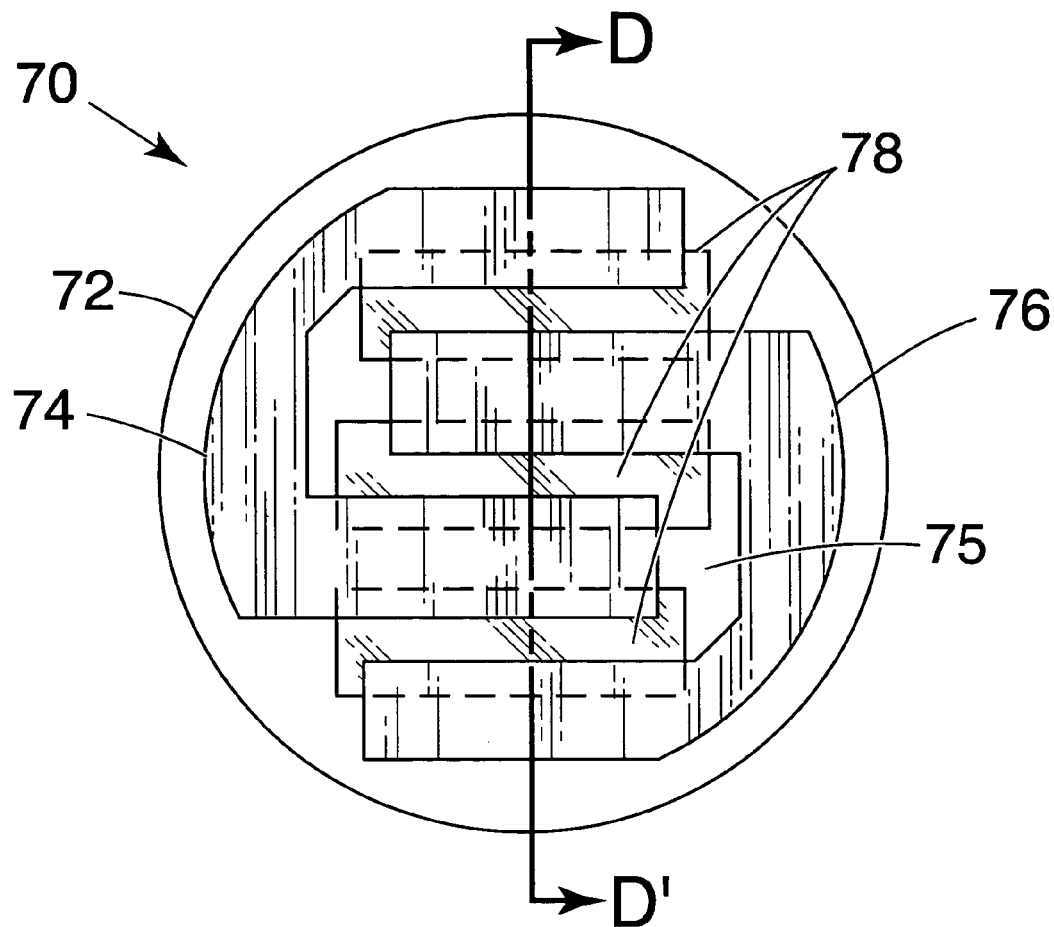
FIG. 7a is a schematic, not-to-scale, top view of a sensing element in accordance with another embodiment of the present invention.
Figure 7B:
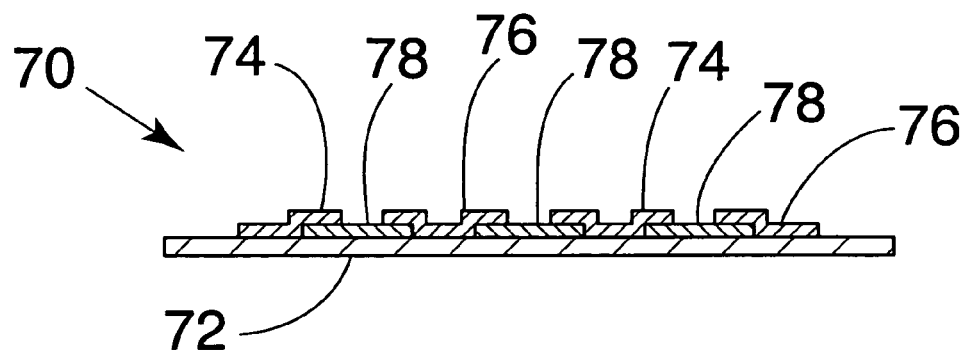

The amount of oxygen ion conducting material in the sensing device can be minimized by using a less expensive, dielectric material for a substrate and depositing the oxygen ion conducting material as one of the layers thereon. Referring to FIGS. 7a and 7b, another sensing device 70 in accordance with some embodiments of the present invention generally comprises a dielectric (electrically insulating) substrate 72 such as $Al_2O_3$, for example. On the substrate a base layer 78 of an oxygen ion conducting material (for example YSZ) is deposited (by screen printing, for example). The base layer 78 is shown as discontinuous but can be a continuous layer if desired. An electrode layer comprising two electrodes 74, 76 is deposited on the dielectric substrate 72 so that the electrodes 74, 76 have a gap 75 therebetween and make contact with base layer 78 along the gap 75 so that the base layer 78 forms a bridge that is, essentially, the sole path for electrical communication between the electrodes 74, 76. The layers may be deposited in reverse order; the electrodes 74, 76 can be deposited first, and the base layer 78 can be deposited thereover. The critical aspect is that the base layer 78 forms a path of electrical communication between the electrodes 74, 76.

Figure 8A:
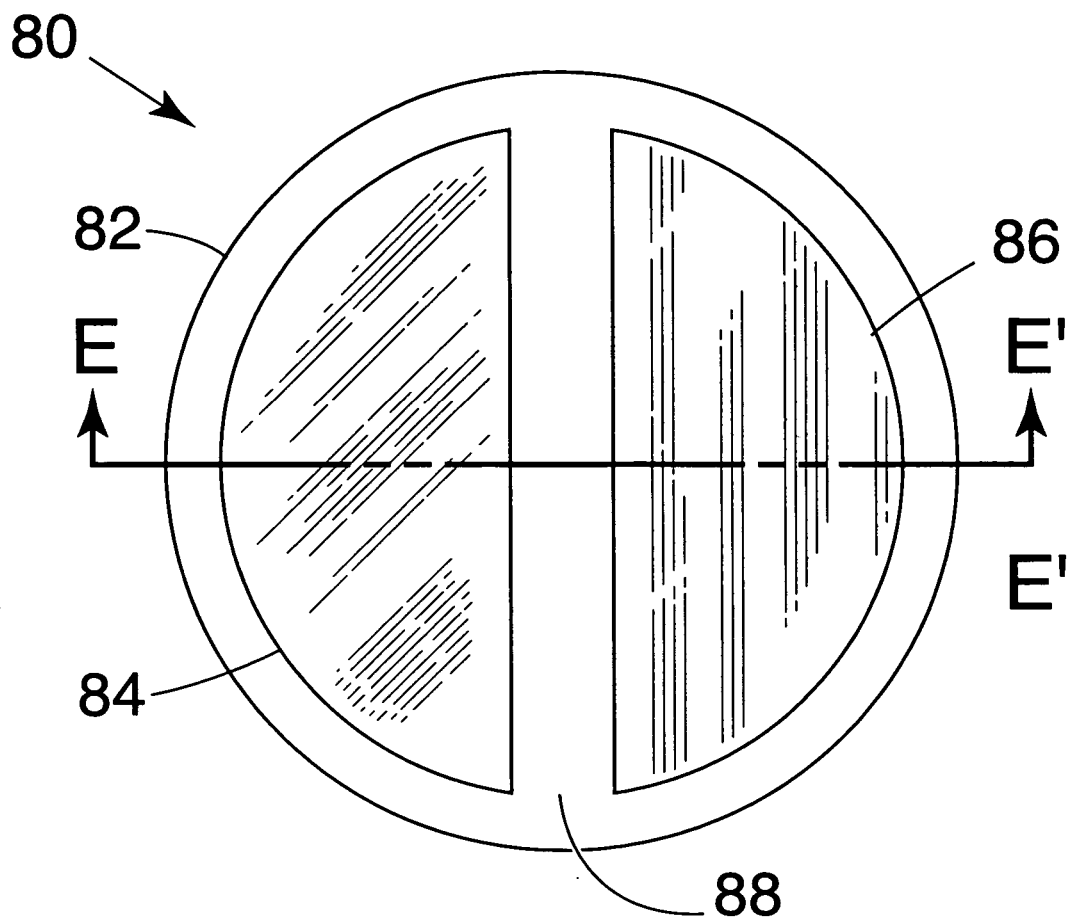
FIG. 8a is a schematic, not-to-scale, top view of a sensing element in accordance with another embodiment of the present invention.
Figure 8B:
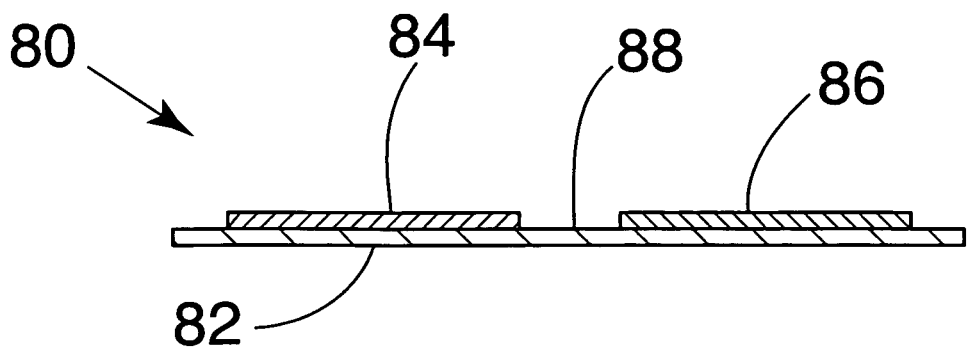
Figure 9:
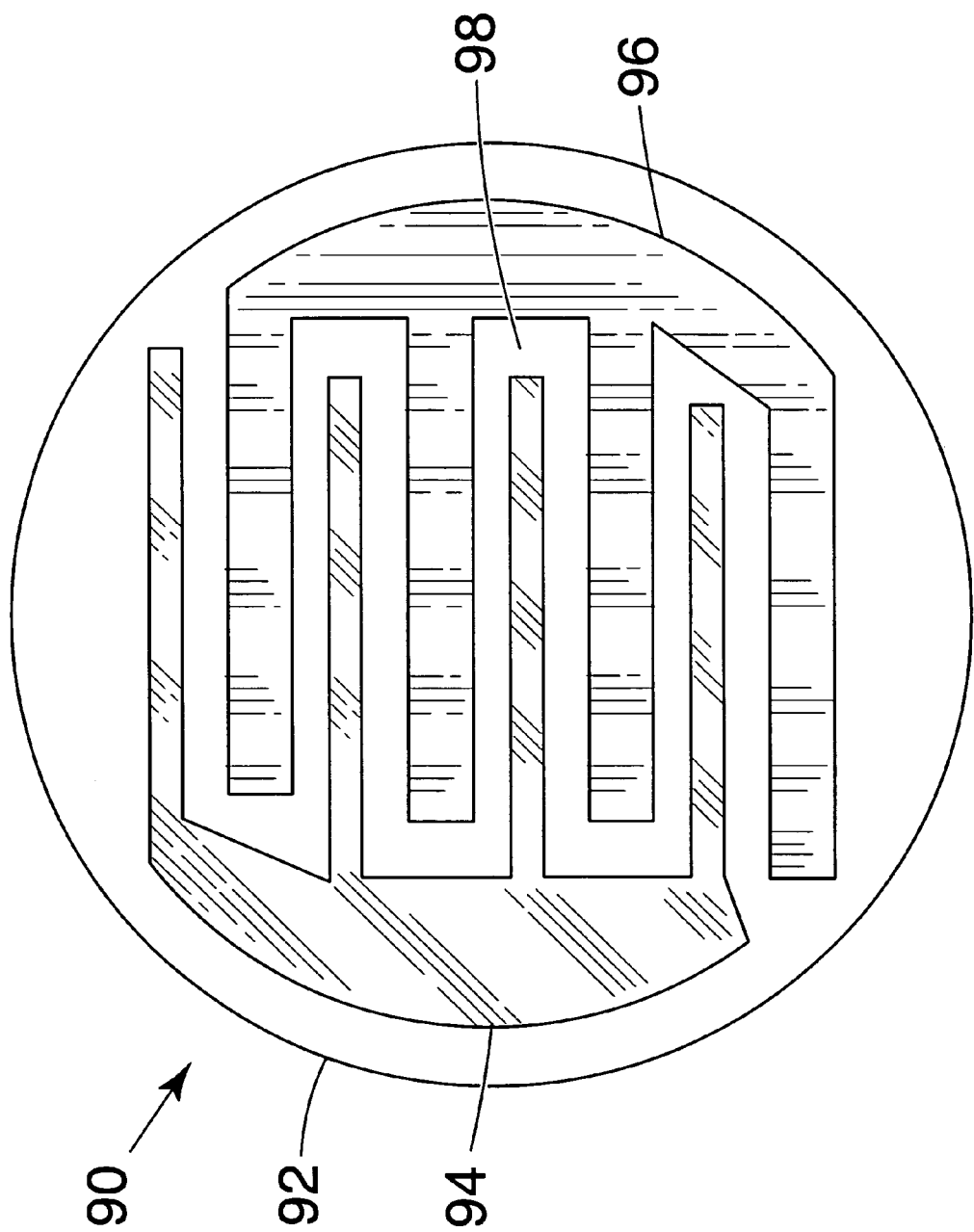
FIG. 9 is a schematic, not-to-scale, top view of a sensing element in accordance with another embodiment of the present invention.

FIGS. 8 and 9 show two more multi-layered embodiments (both employing a YSZ substrate) of the present invention but for these embodiments the multiple layers do not physically touch. For the embodiment in FIG. 8, the co-planar electrodes are nominally identical in area but the composition of the two electrodes is different. For the embodiment in FIG. 9, the co-planar electrodes differ both in area and composition.

Referring to FIG. 8, a sensing device 80 can be comprised of an oxygen-ion conducting substrate 82 with co-planar electrodes 84, 86 separated by a gap 28. The electrodes 84, 86 are comprised dissimilar materials.

Referring to FIG. 9, a sensing device 90 can be configured in similar fashion to the sensing device illustrated in FIG. 3 and comprised of an oxygen-ion conducting substrate 92 with co-planar, interdigitated electrodes 94, 96 that define a serpentine gap 98. The electrodes 94, 96 are comprised dissimilar materials. One electrode 96 has a greater surface area than the other electrode 94.

The embodiments of the present invention shown in FIGS. 8 and 9 can employ, for example, one electronically conductive oxide electrode and the noble metal electrode. These embodiments can also employ two different oxide electrodes, or oxides partnered with alternate noble metal/noble metal alloys such as, for example, Pt modified with a small amount of gold as is done for the first cavity of conventional pumping-type $NO_x$ sensors.

Figure 10:
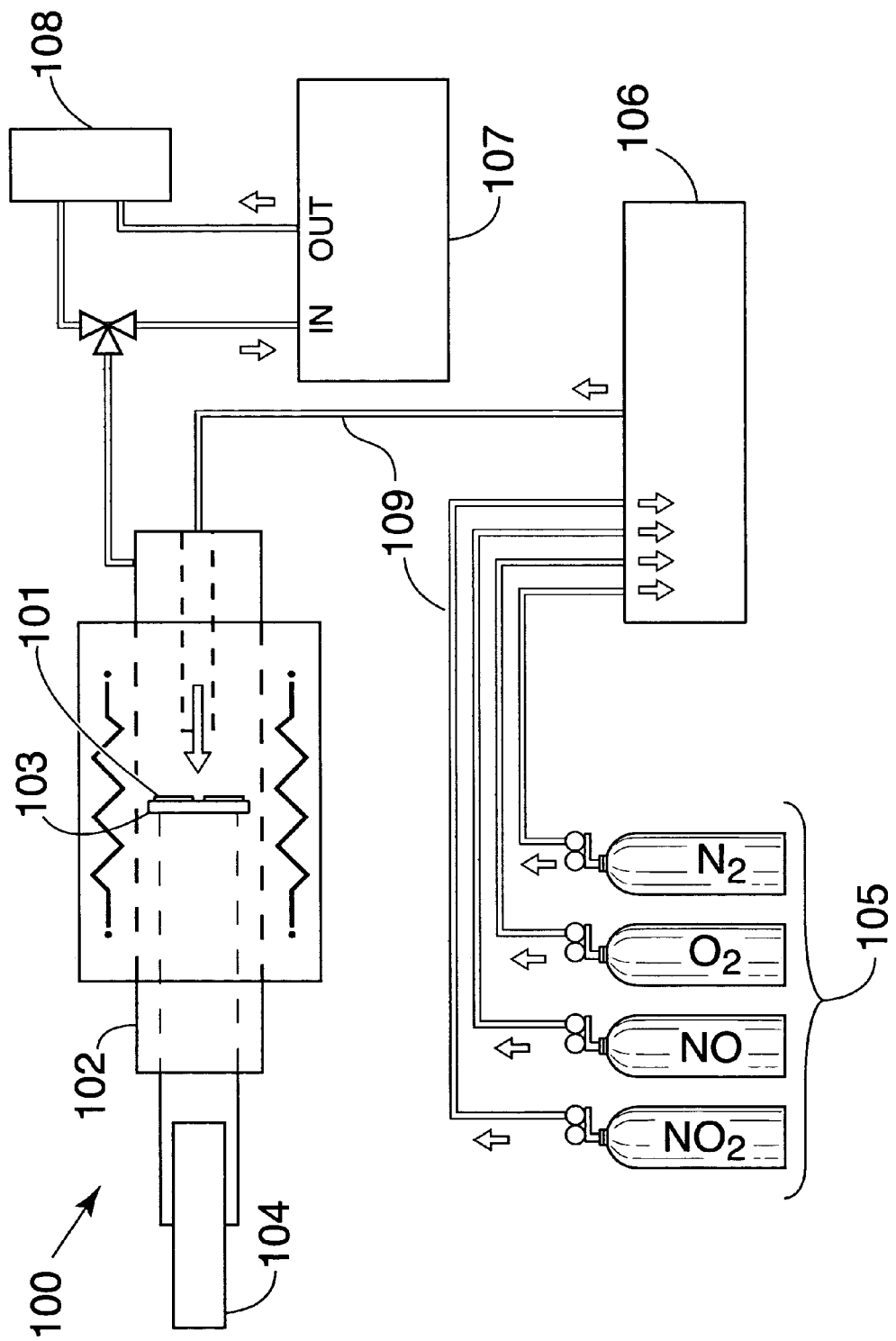
FIG. 10 shows schematically a testing apparatus which was used to assess the $NO_x$ sensing performance of the sensing elements shown schematically in FIG. 1-9.

A typical, well-known testing apparatus for testing $NO_x$ sensors, shown in FIG. 10, was used to test the invention. The apparatus 100 comprises: a tube-furnace 102, means for holding a sensor specimen 103; electronics package 104 for applying bias to the specimen 103 and measuring voltage and/or current changes during testing of the specimen 103; gas cylinders 105 containing appropriate test gases, a gas mixing unit 106 for mixing test gases; an $NO_x$ meter 107 for measuring $NO_x$ in gas eluted from the system; an exhaust system 108; and requisite plumbing connections, valves, pressure regulators, etc. 109.

Figure 11:
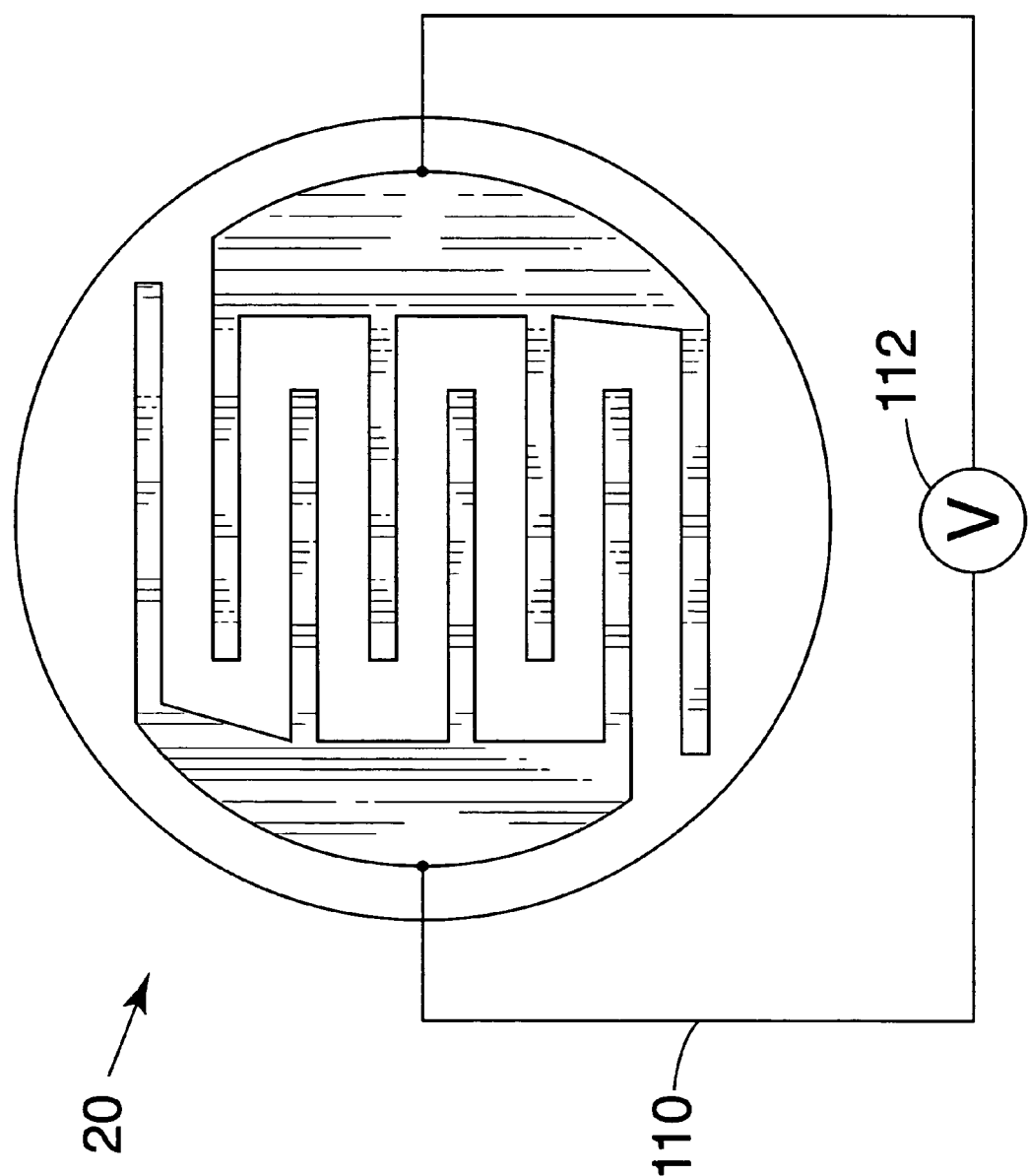
FIG. 11 shows electrical connections made to the sensing elements for no biasing. These electrical connections have been used for all the element geometries shown in FIGS. 1-9.

FIG. 11 shows a typical, well-known zero-biased testing circuit 110 including a DC voltmeter 112 in electrical communication with an embodiment 20 of the present invention.

Figure 12:
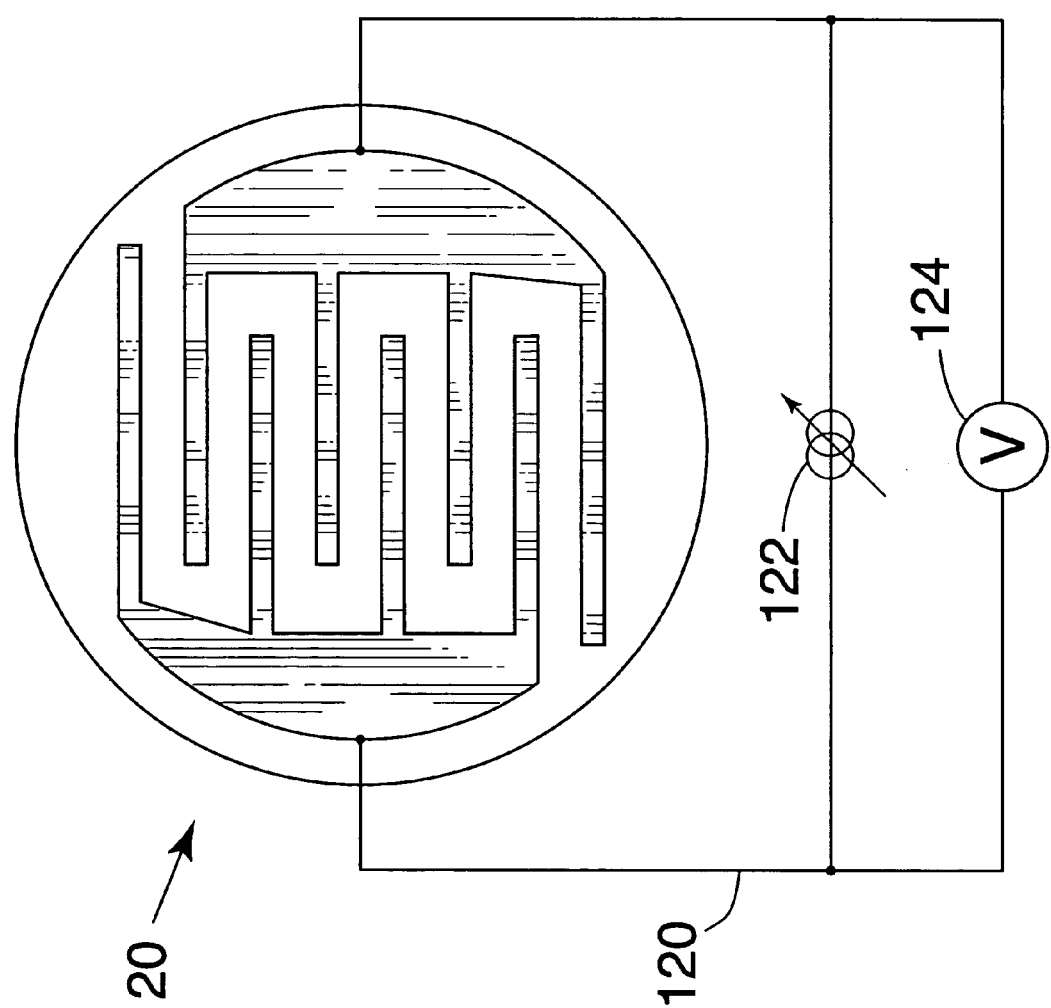
FIG. 12 shows electrical connections made to the sensing elements for current biasing. These electrical connections have been used for all the element geometries shown in FIGS. 1-9.

FIG. 12 shows a typical, well-known current-biased testing circuit 120 including a DC current biasing source 122 and DC voltmeter 124 in parallel electrical communication with an embodiment 20 of the present invention.

Figure 13:
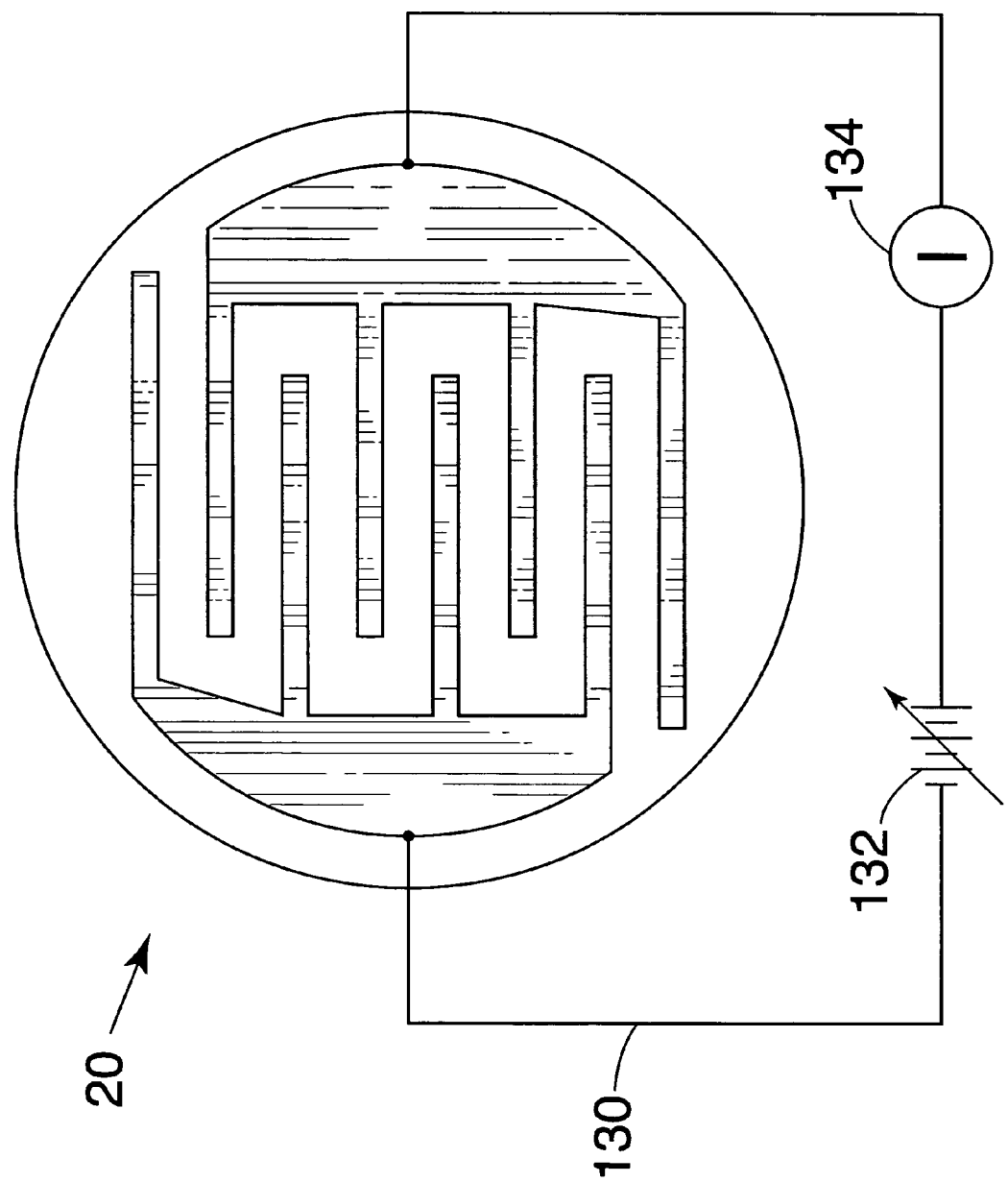
FIG. 13 shows electrical connections made to the sensing elements for voltage biasing. These electrical connections have been used for all the element geometries shown in FIGS. 1-9

FIG. 13 shows a typical, well-known voltage-biased testing circuit 130 including a DC voltage biasing source 132 and ammeter 134 in serial electrical communication with an embodiment 20 of the present invention.

Any device which can measure DC resistance or AC impedance across the two electrodes can substitute for the circuits described above.

Example I

NOx sensing elements having various electrode materials were fabricated with the general configuration shown in FIGS. 1a, 1b. The substrates were YSZ (8 mol % $Y_2O_3$) disks 1.6 cm in diameter and 0.1 cm in thickness prepared by tape-casting, laminating and sintering. The electrodes were produced by screen-printing followed by thermal treatment.

The sensing elements were mounted in the apparatus shown in FIG. 10. A gas mixing unit 106 (Environics 4000, available from Environics, Tolland, Conn.) was used to mix $N_2$, $O_2$, and $NO_x$ (NO or $NO_2$, 5000 $ppm_V$ in $N_2$)) from gas cylinders 105 at room temperature. Mixture compositions were in the range 7 vol %$\leq$[$O_2$]$\leq$20 vol %, 30 $ppm_V\leq$[$NO_x$] $\leq$1500 $ppm_V$, with the balance being $N_2$. These gas mixtures were presented to the side of the sensing element 103 supporting the electrodes 101, as shown by an arrow. The resistively heated furnace 102 was used to simulate the elevated temperature service conditions expected in practical implementations of the disclosed invention.

In order to demonstrate different aspects of the present invention, the sensing element was electrically connected to the electronics package 104 in the manner shown in either FIG. 11 (zero bias), FIG. 12 (current bias), or FIG. 13 (voltage bias).

Example II

NOx sensing elements having various electrode materials were fabricated as in Example I but with the geometry shown in FIG. 2.

Example III

NOx sensing elements having various electrode materials were fabricated as in Example I but with the geometry shown in FIG. 3.

Example IV

NOx sensing devices having various electrode materials were fabricated as in Example I but with the geometry shown in FIG. 4.

Example V

NOx sensing devices having various electrode materials were fabricated as in Example I but with the geometry shown in FIG. 5.

Example VI

NOx sensing devices having various electrode materials were fabricated as in Example I but with the geometry shown in FIG. 6.

Example VII

NOx sensing devices having various electrode materials were fabricated as in Example I but with the geometry shown in FIG. 7.

Example VIII

NOx sensing devices having various electrode materials were fabricated as in Example I but with the geometry shown in FIG. 8.

Example IX

NOx sensing devices having various electrode materials were fabricated as in Example I but with the geometry shown in FIG. 9.

Example X

NOx sensing devices made of $Ba_{0.08}Cu_{0.92}Cr_2O_4$ on YSZ in accordance with Example I were tested with the electrical connections shown in FIG. 11. In a three-step test, the specimen temperature was alternately raised and lowered at 2° C./min. while introducing test-gases into 7 vol % $O_2$, 93 vol % $N_2$:

1. Heating from 510° C. to 710° C. while introducing 5 minute pulses of 450 $ppm_V$ $NO_2$/0 ppm $NO_2$;
2. Cooling from 710° C. to 510° C. while introducing 5 minute pulses of 450 $ppm_V$ NO/0 ppm NO; and
3. Cooling from 610° C. to 510° C. while imposing a constant $O_2/N_2$ ratio with no input $NO_x$.

Figure 14:
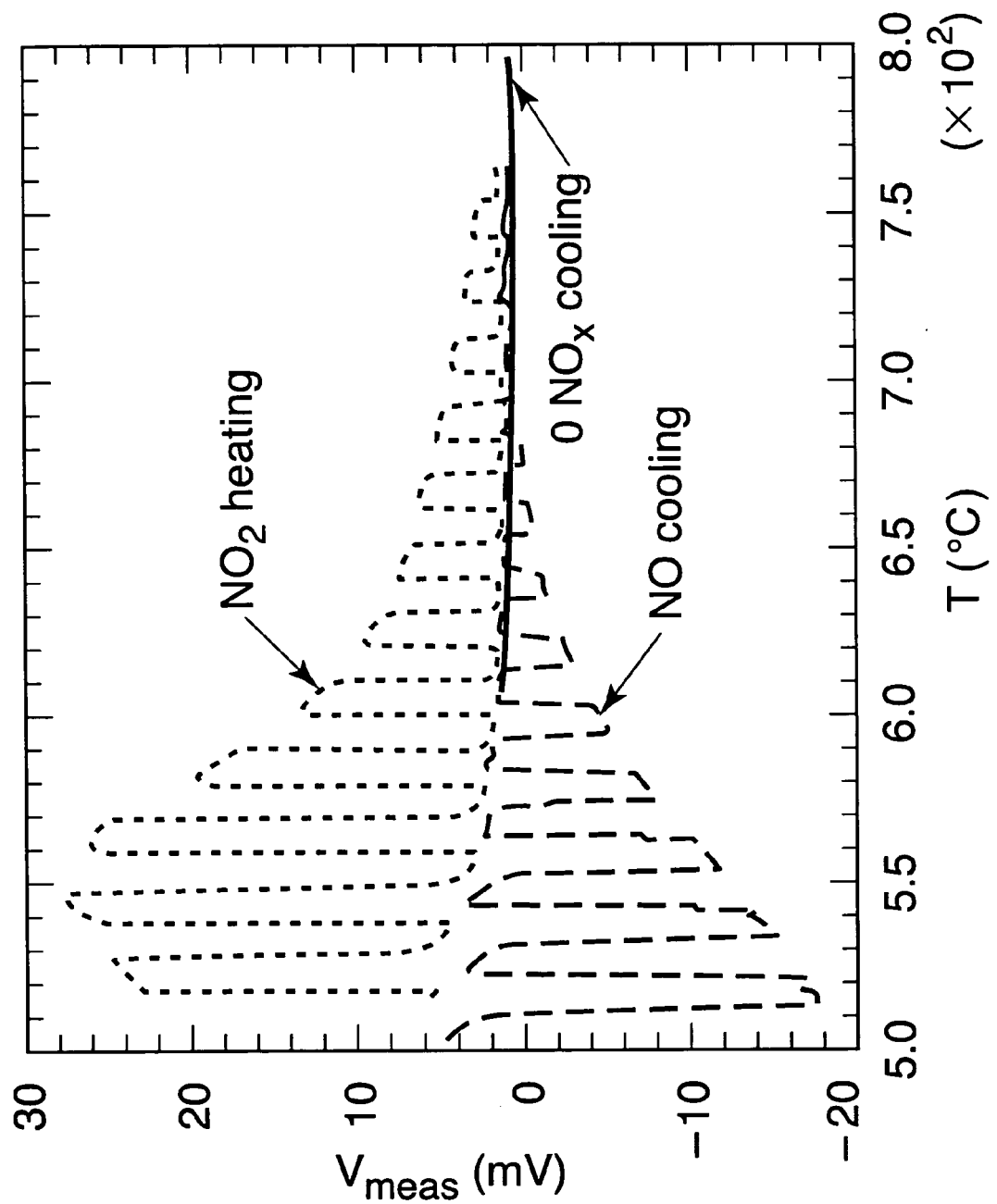
FIG. 14 is a graph showing data from testing of the present invention.

As seen in FIG. 14, the 450 $ppm_V$ pulses of $NO_2$ consistently produced positive voltages in the mV range, the magnitude of which decreases with T. On the other hand, the NO pulses produced voltage signals that are opposite in sign and in general smaller in magnitude than those produced by $NO_2$ at any given temperature. With zero input $NO_x$, the measured voltage is near zero. These data indicate that the present invention, when external electrical connections are made as shown in FIG. 11, can be used to detect both NO and $NO_2$. However, due to the differing sign and magnitude of the responses to NO and $NO_2$, the present invention (when external electrical connections are made as shown in FIG. 11) is unable to unambiguously determine [NO] or [$NO_2$] in mixtures that contain both gases. This can be extremely deleterious for many applications, as the relative abundance of NO and $NO_2$ may be unknown or impossible to predict a posteriori. The behavior illustrated in FIG. 14 is well known in the art and is an impediment to practical applications.

Example XI

Figure 15:
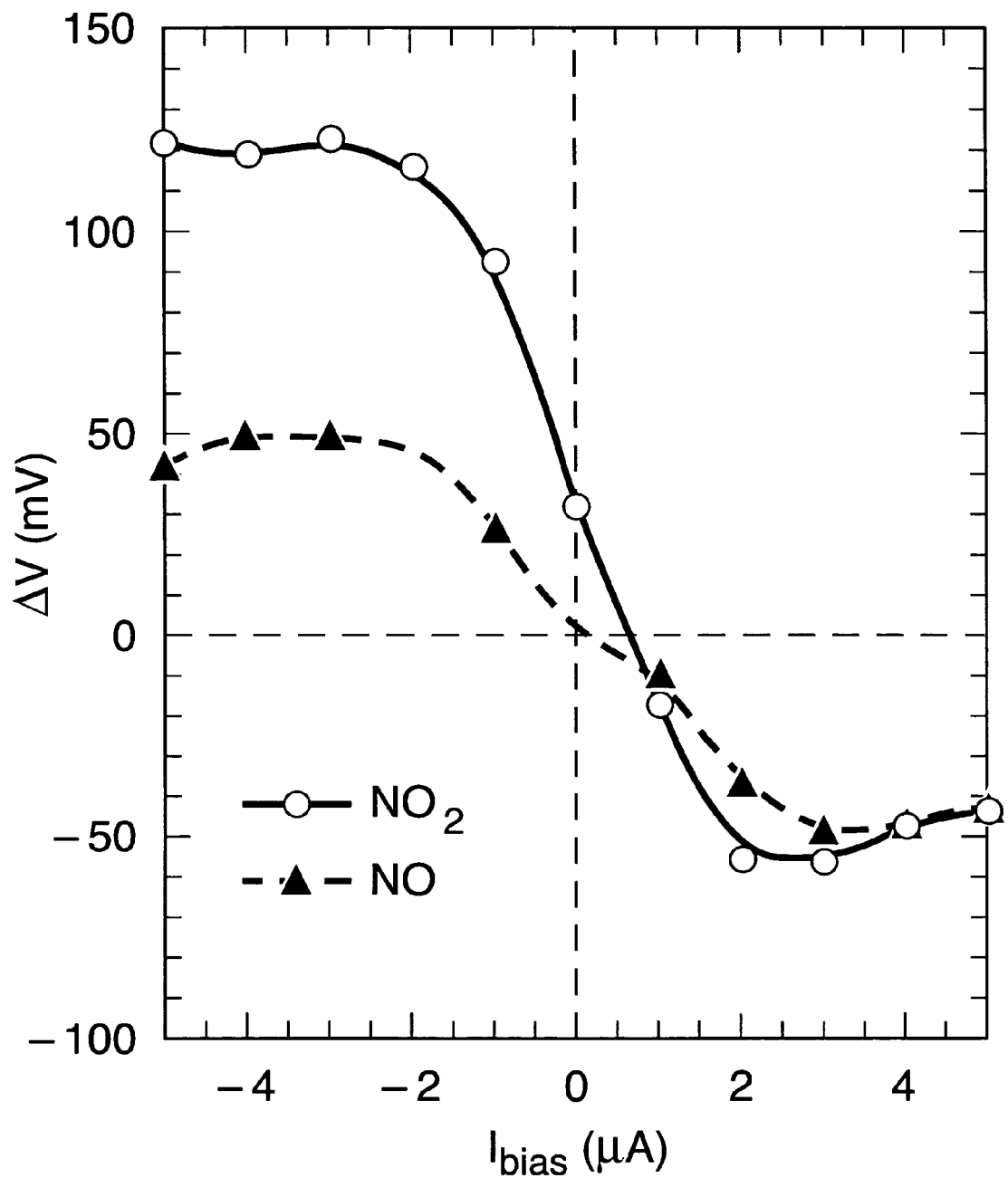
FIG. 15 is a graph showing data from testing of the present invention.

NOx sensing devices made of $Ba_{0.08}Cu_{0.92}Cr_2O_4$ on YSZ in accordance with Example X were tested with the electrical connections shown in FIG. 12. Bias "sweeps" were conducted (in which the current applied to the sensing element was stepped at discrete levels (−5, −4, −3, −2, −1, 0, 1, 2, 3, 4, 5 µA) at 600° C. under atmospheres of first 0 $ppm_V$ $NO_x$ and then 450 $ppm_V$ NO and finally 450 $ppm_V$ $NO_2$ (7 vol % $O_2$, balance $N_2$ in all three cases). The voltage readings were then compared at each bias level to deduce an approximate measure of the voltage change caused by the presence of NO and $NO_2$. The voltage changes thus determined are shown in FIG. 15. From this Fig. it can be seen that with current biases on the order of 2-4 µA, the voltage changes induced by 450 $ppm_V$ NO and $NO_2$ are approximately the same.

Example XII

Figure 16:
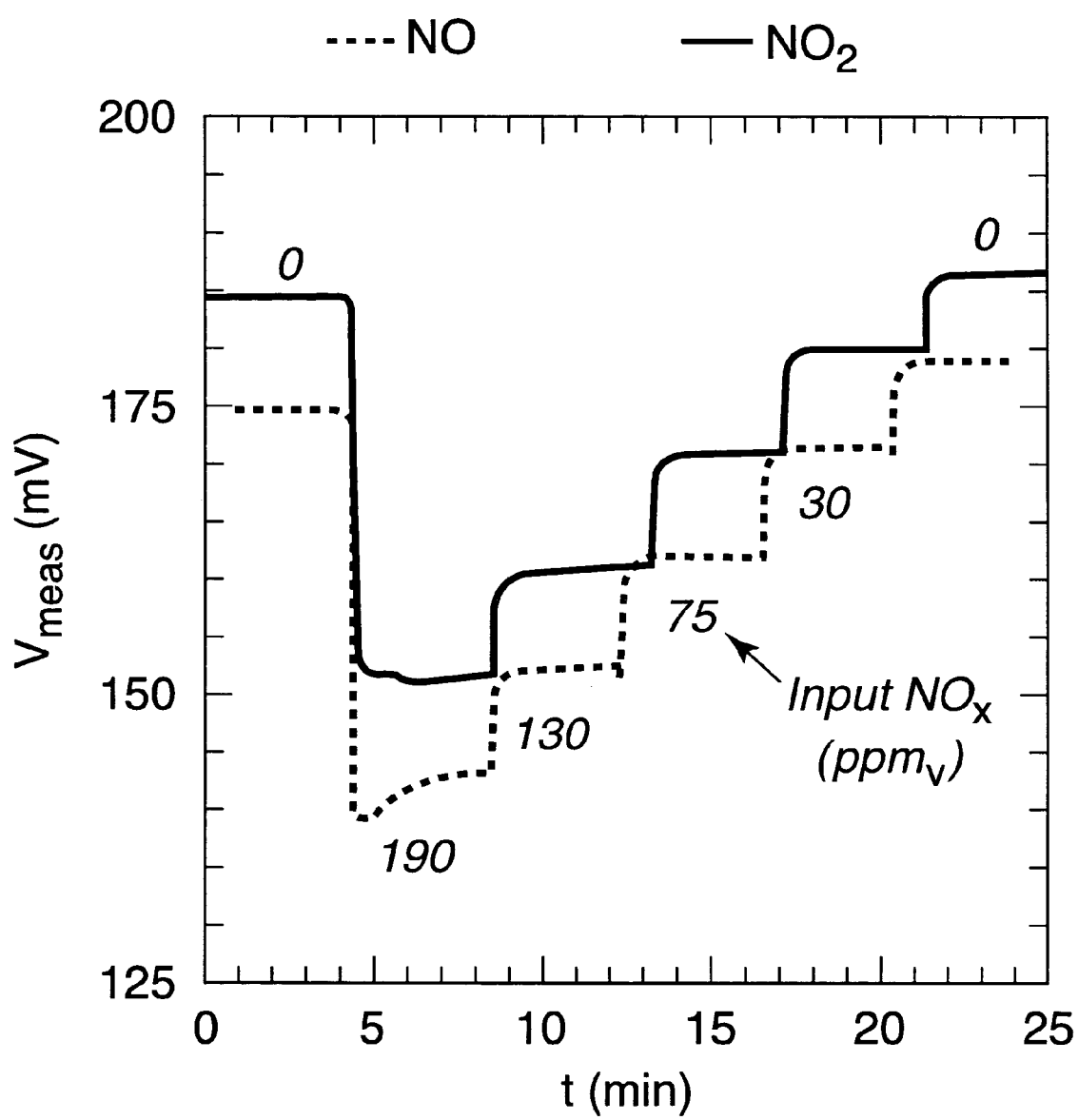
FIG. 16 is a graph showing data from testing of the present invention.
Figure 17:
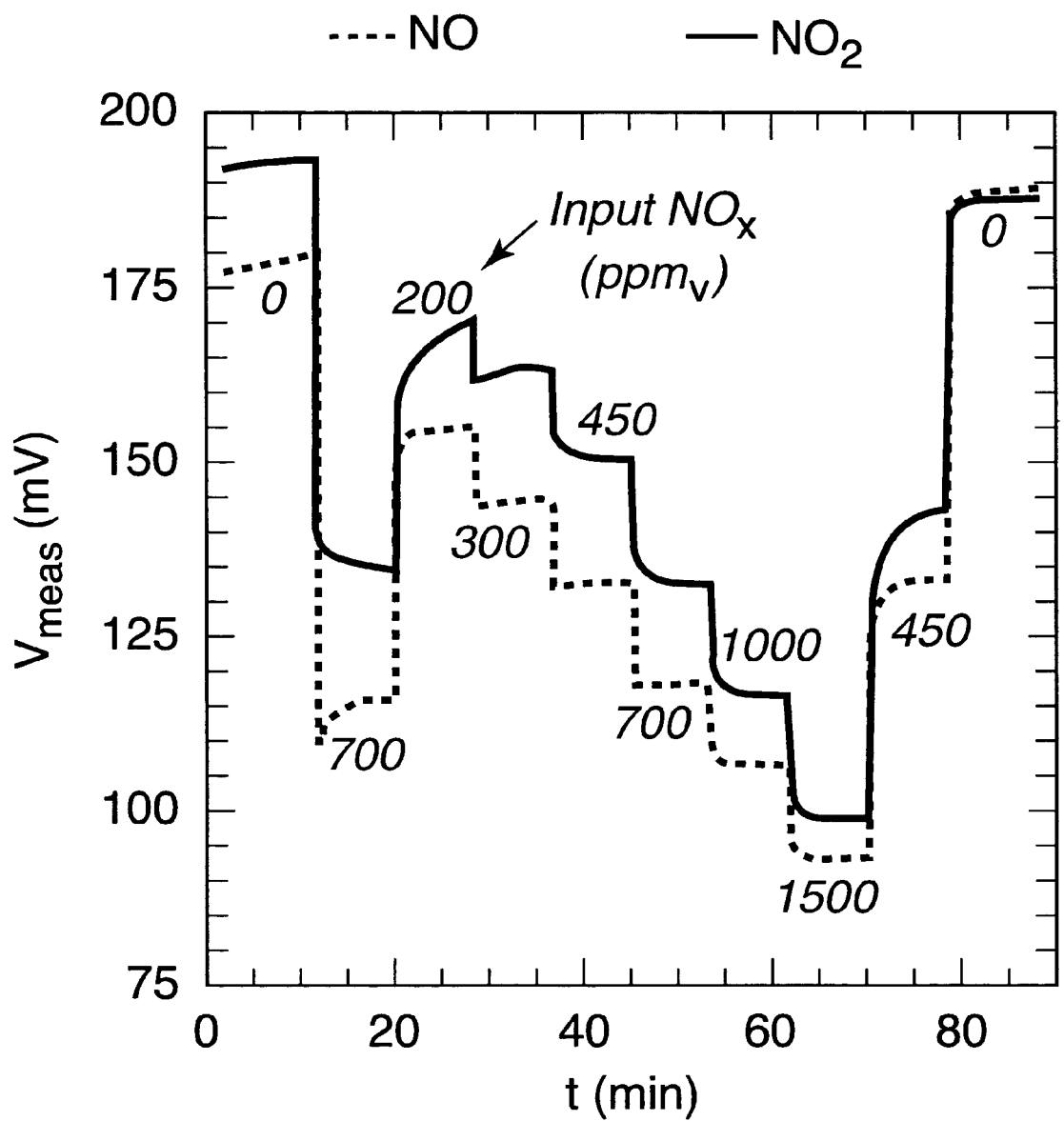
FIG. 17 is a graph showing data from testing of the present invention.

The current bias on the sensing device described in Example XI was fixed at 2.5 µA (a current bias that gave approximately the same response to NO and $NO_2$), the temperature at 600° C., and the input [$NO_x$] was systematically varied (with 7 vol % $O_2$, balance $N_2$). FIGS. 16-17 show that for [$NO_x$] concentrations in the range 30 $ppm_V\leq$1500 $ppm_V$ the current-biased sensing element yielded approximately the same response (in terms of the change in $V_{meas}$) irrespective of the identity of the input $NO_x$ species (NO or $NO_2$). Therefore, the data in FIGS. 16-17 indicate the important result that the current-biased sensing element is functioning as a "total $NO_x$" sensor, with both NO and $NO_2$ producing similar (in terms of algebraic sign and magnitude) sensing responses. It is important to the scope and aim of the present disclosure to realize that the application of "bias" has remediated the aforementioned difficulty of the element response to NO and $NO_2$ differing in algebraic sign (see FIG. 14).

Figure 18:
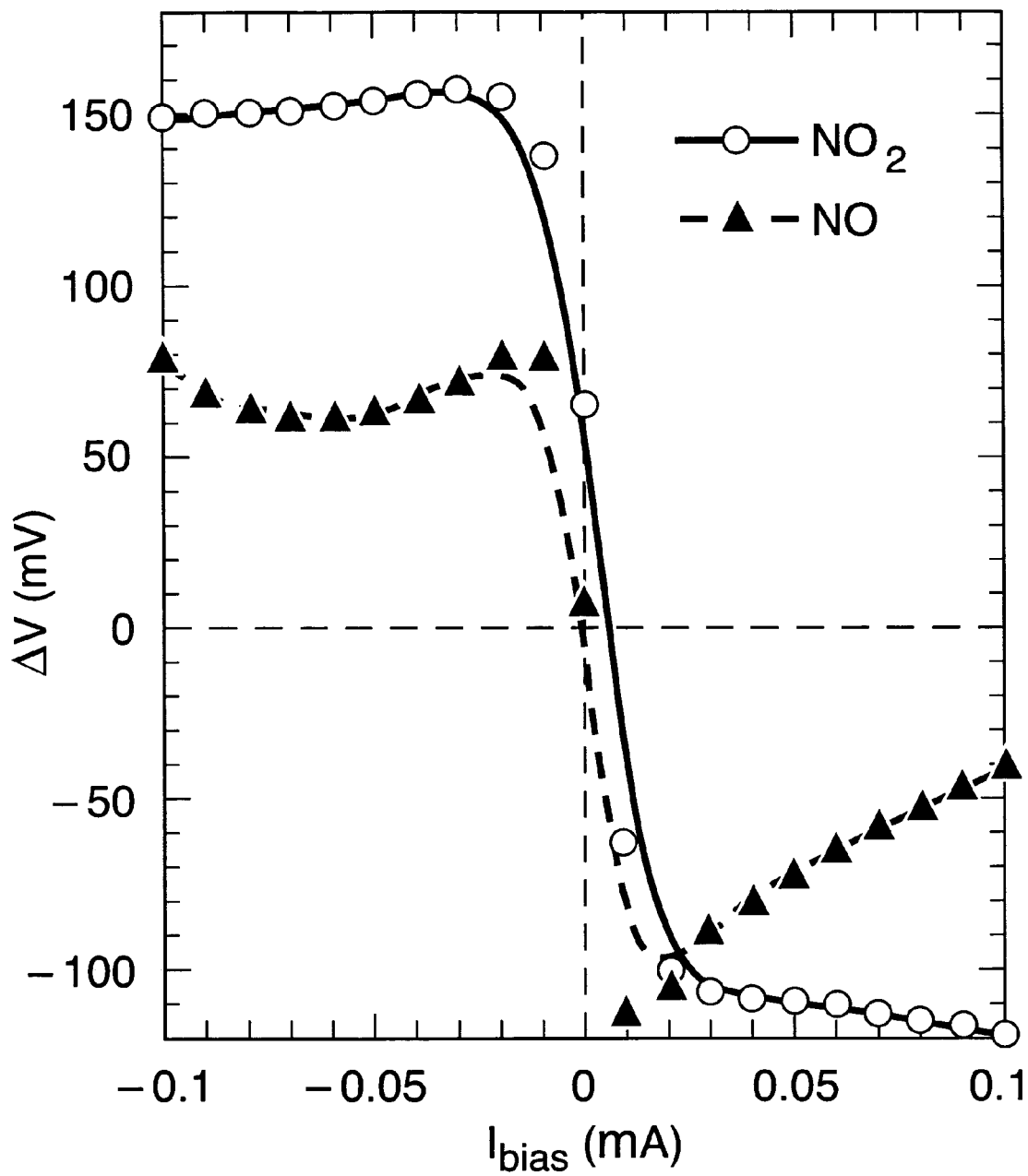
FIG. 18 is a graph showing data from testing of the present invention.

Example XIII $NO_x$ sensing devices made of $La_{0.85}Sr_{0.15}CrO_3$ on YSZ were made in accordance with Examples I, II, and III and tested in a manner according to Example I, with the electrical connections to the devices being made in accordance with FIG. 12. Testing as described in Example XI was conducted to determine the bias levels which gave approximately the same response to NO and $NO_2$. FIG. 18 shows the results of such testing on the device made in accordance with Example I. From this Fig. it is apparent that a bias of approximately 0.02 μA yielded "total $NO_x$" sensing behavior for this device.

Figure 19:
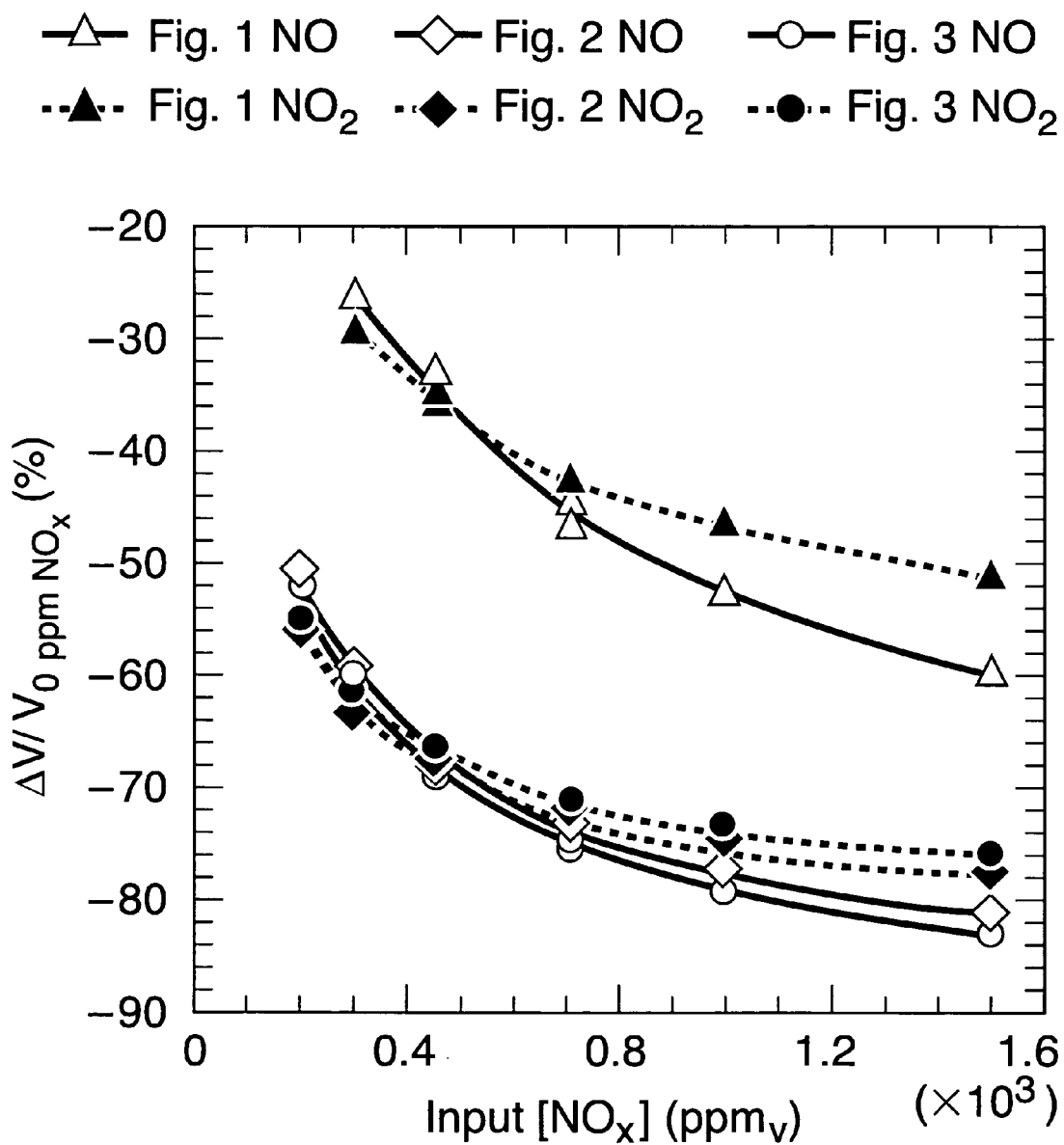
FIG. 19 is a graph showing data from testing of the present invention.
Figure 20:
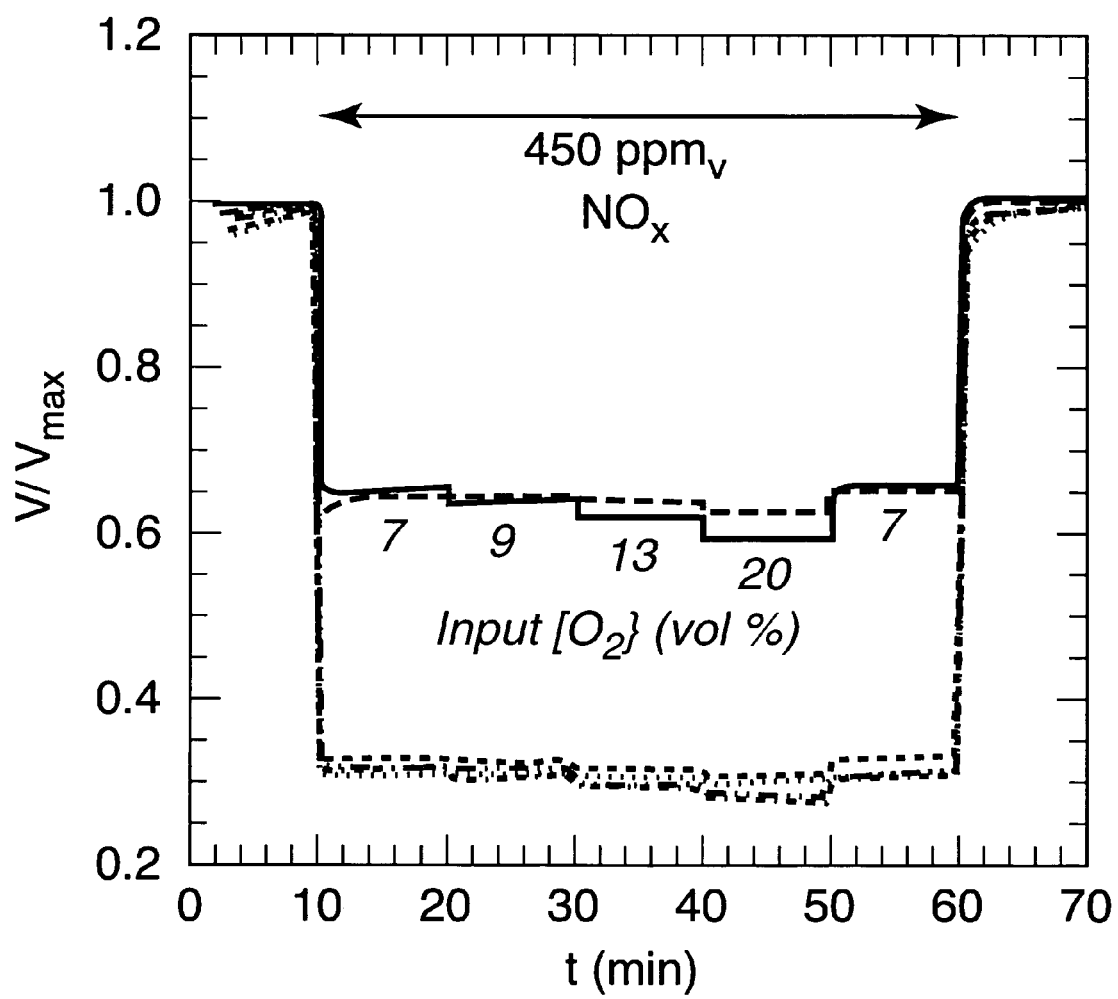
FIG. 20 is a graph showing data from testing of the present invention.

Testing at fixed bias (the bias that gave "total $NO_x$" sensing behavior, this bias was different for each of the devices), T (600° C.), and $[O_2]$ (7 vol %) was carried out for each of the devices in the manner described in Example XII and the resultant data are shown in FIG. 19. The $[O_2]$ in the test gas was also varied systematically at fixed $[NO_x]$ (450 $ppm_V$) for each of the devices and the resultant data are shown in FIG. 20. The data in FIG. 19-20 demonstrate that changing the element geometry from that shown in FIG. 1 to that shown in either FIG. 2 or 3 alters the magnitude of the sensing device response, but does not change the general "total $NO_x$" nature of said response.

Example XIV $NO_x$ sensing devices made of $La_{0.85}Sr_{0.15}CrO_3$ on YSZ were made in accordance with Examples I and IV and tested in a manner according to Example I, with the electrical connections to the devices being made in accordance with FIG. 12. Testing as described in Example XI was conducted to determine the bias levels which gave "total $NO_x$ sensing" (approximately the same response to NO and $NO_2$) (450 $ppm_V$ $NO_x$ in 7 vol % $O_2$ at 700° C.).

Figure 21:
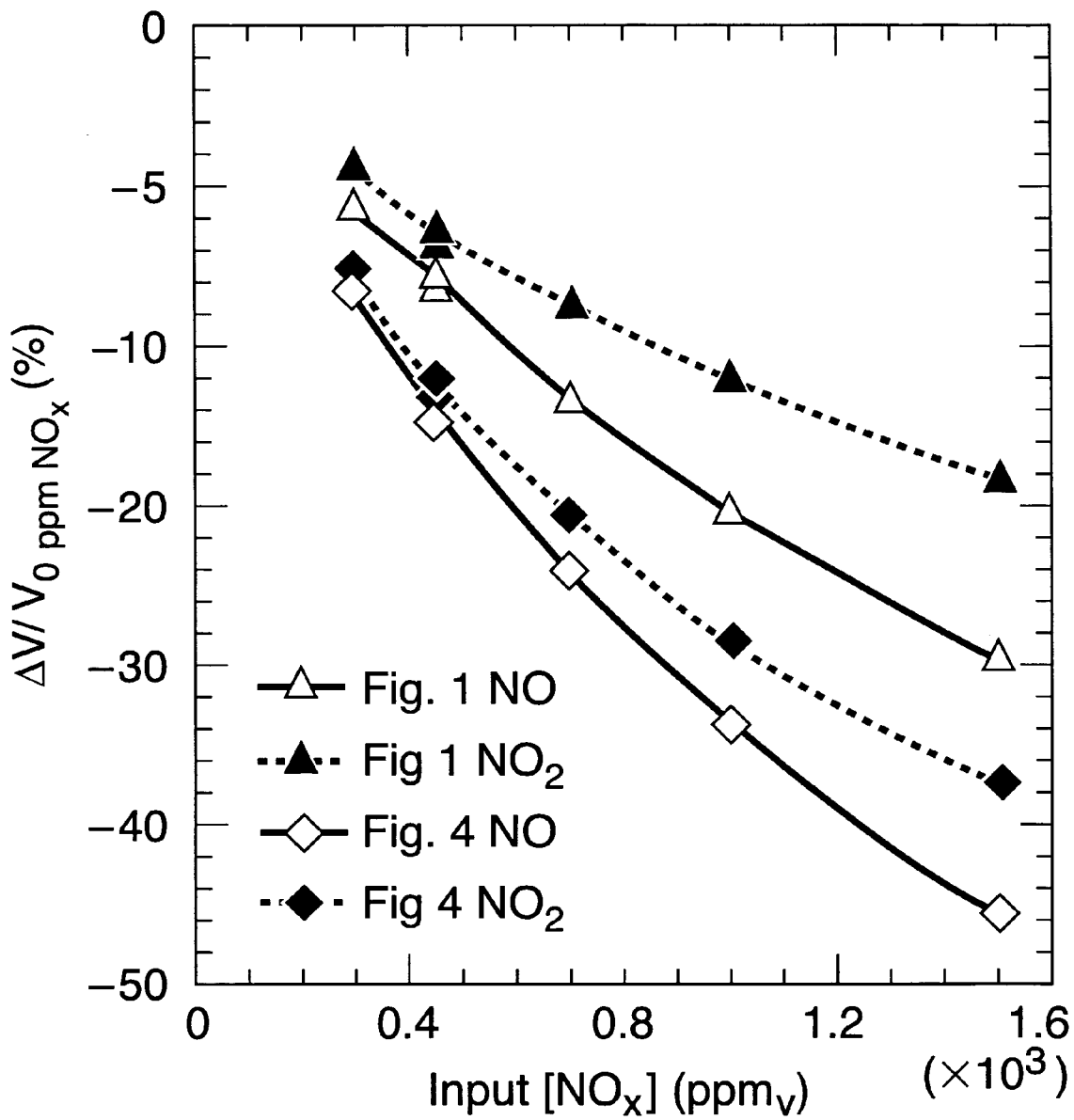
FIG. 21 is a graph showing data from testing of the present invention.

Testing at fixed bias (the bias that gave "total $NO_x$" sensing behavior, this bias was different for the device made according to Example I and that according to Example IV), T, (700° C.), and $[O_2]$ (13 vol %) was carried out for each of the devices in the manner described in Example XII and the resultant data are shown in FIG. 21. As was the case in the prior example, changing the geometry from that shown in FIG. 1 to that shown in FIG. 4 did not change the fundamental sensing behavior of the device.

The foregoing examples demonstrate that host of different geometries can be employed to fabricate sensing devices essentially similar to those described in Examples I-IV. Therefore it is contemplated that the precise geometry of the electrodes is not critical to the invention.

Mounting electrodes on different sides of the substrate (non-co-planar arrangement) is considered to be a variation of the geometry of the present invention. Details of the internal electrical field in the oxygen ion conductor may depend on geometry, but the fundamental technical aspect of the examples described hereinabove is compositionally identical oxide electrodes, in electrical communication via the oxygen ion conductor. Geometry changes that conspire to place electrodes in gases of different composition also do not change fundamental technical aspect.

Moreover, a plurality of spaced pairs of electrodes may be used on one or more sides (surfaces) of a substrate without departing from the scope of the present invention. For example, any of the embodiments described herein can have another pair of electrodes on the opposite side of the substrate. The electrode pairs can be identical or they can be different. The analytical behavior of such embodiments may be different and require adjustments in operating parameters, but the principles of operation are essentially the same.

Example XV $NO_x$ sensing devices made of $La_{0.85}Sr_{0.15}CrO_3$ on YSZ were made in accordance with Example III and tested in a manner according to Example I, with the electrical connections to the devices being made in accordance with FIG. 12. Testing as described in Example XI was conducted to determine the bias level which gave approximately the same response to NO and $NO_2$, but in this instance the input $[NO_x]$ concentration was 77 $ppm_V$.

Figure 22:
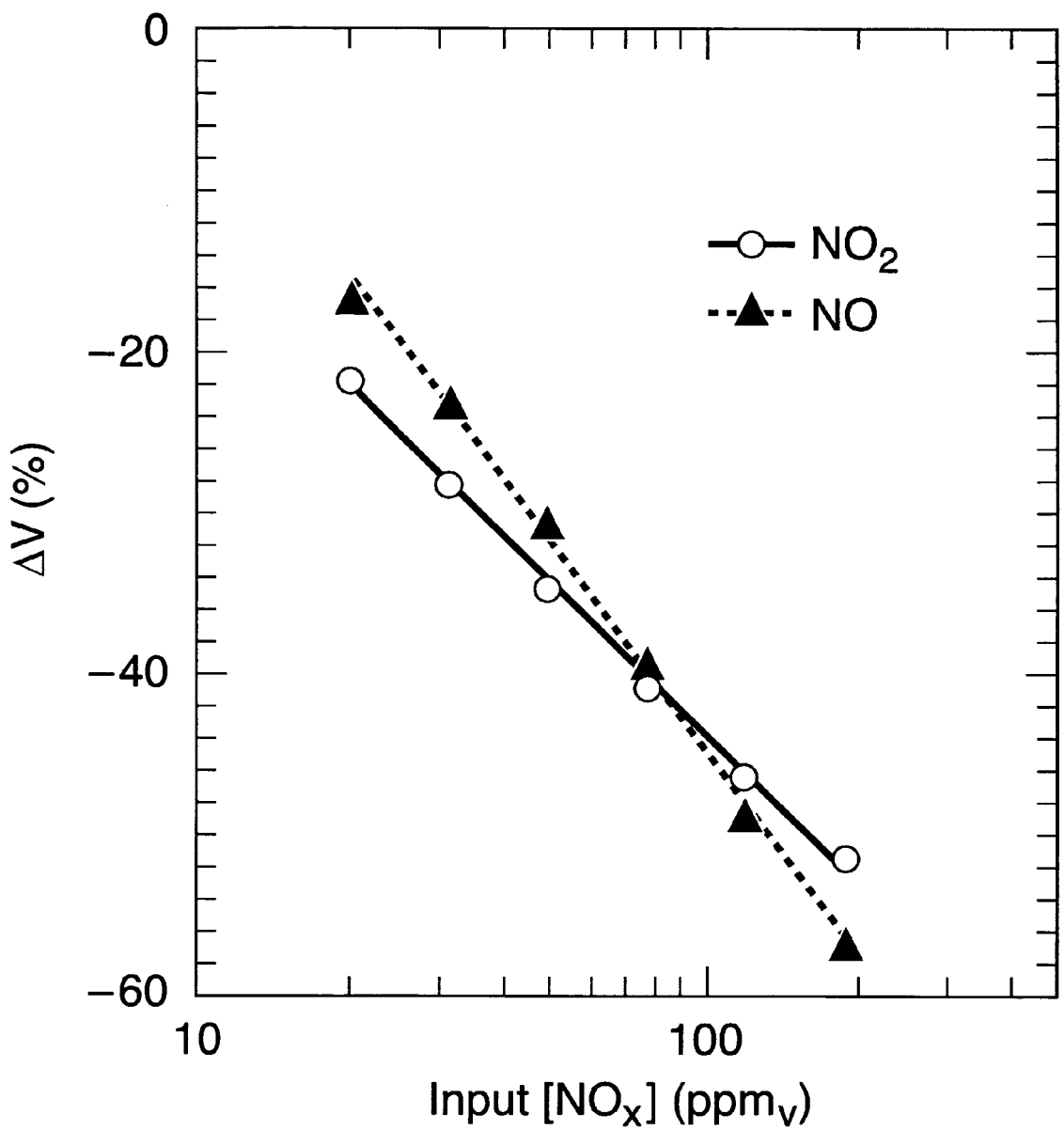
FIG. 22 is a graph showing data from testing of the present invention.

Testing was carried out as described in Example XII above at fixed bias, temperature 600° C., and $[O_2]$ 7 vol %. First the input [NO] and then the input $[NO_2]$ were varied systematically across the concentration range 20 $ppm_V$ to 190 $ppm_V$. FIG. 22 shows the voltage changes (in terms of the percent change from the voltage measured with no $NO_x$ present) induced by both NO and $NO_2$. It is clear from this Fig. that the "total $NO_x$" behavior exhibited in FIGS. 19 and 20 is preserved down to $NO_x$ concentrations on the order 10 to 100 $ppm_V$.

Example XVI

Figure 23:
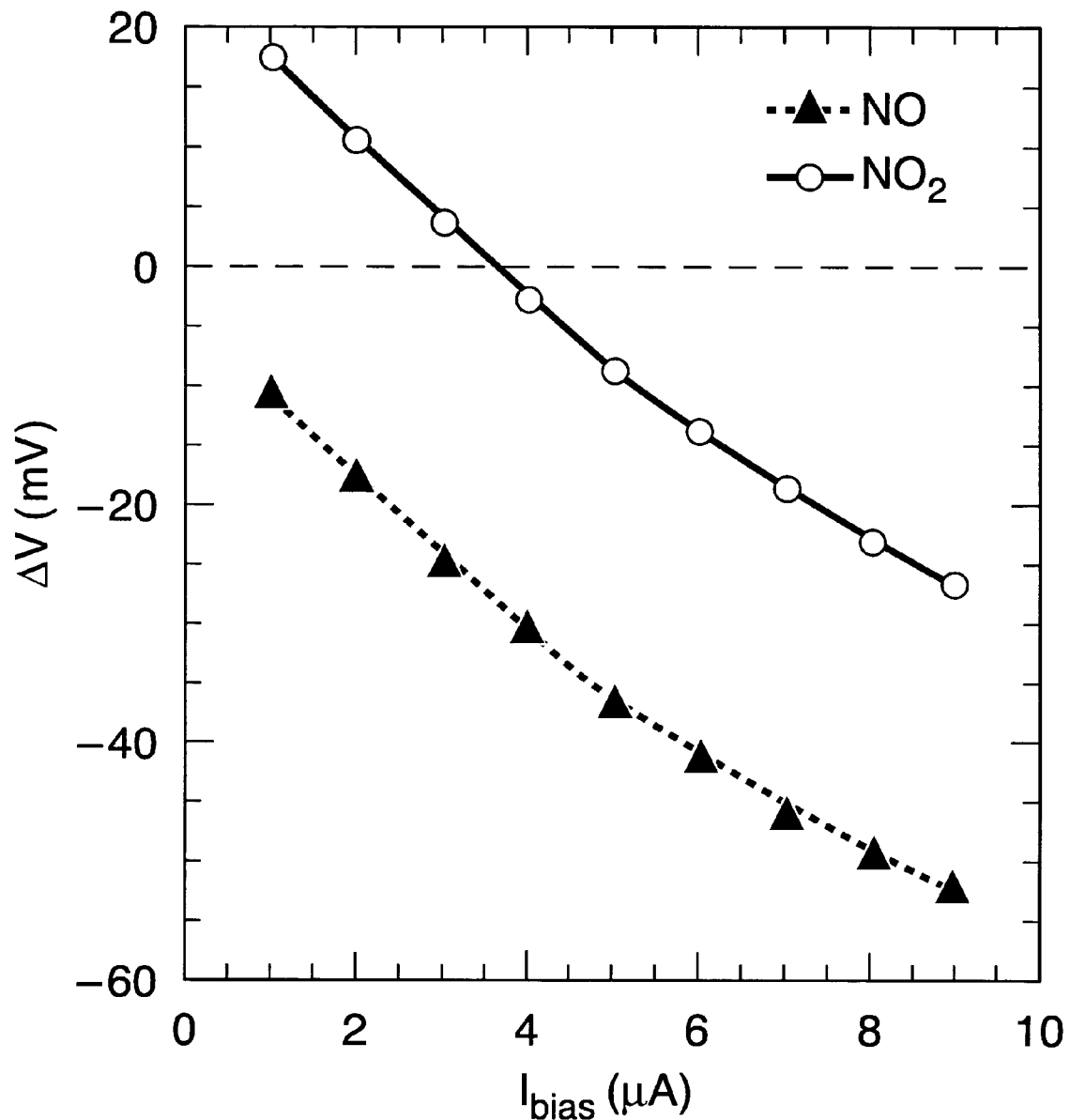
FIG. 23 is a graph showing data from testing of the present invention.
Figure 24:
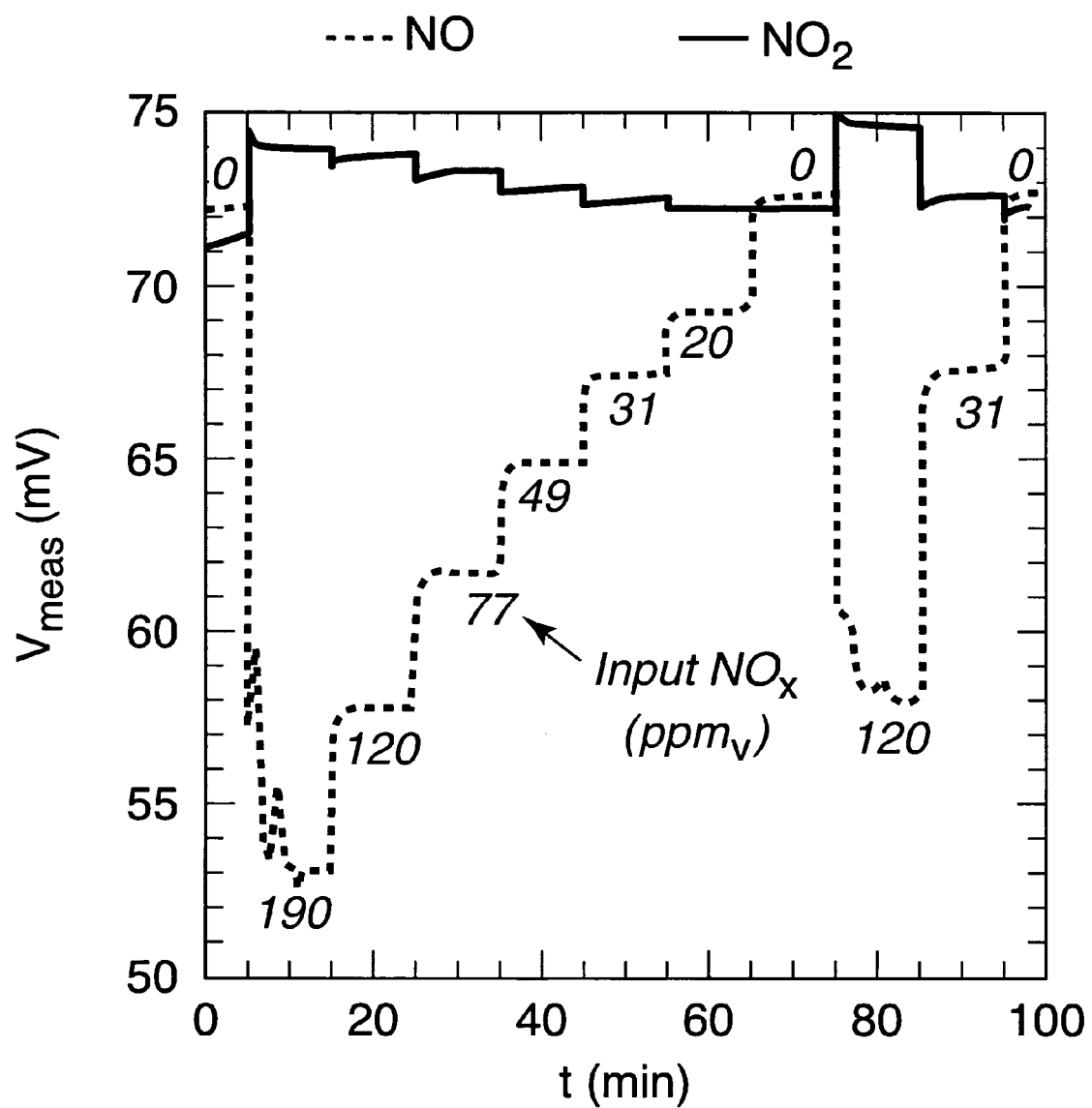
FIG. 24 is a graph showing data from testing of the present invention.

Sensing devices using $La_{0.85}Ba_{0.15}CrO_3$ (LBC) on YSZ were made in accordance with Example III and tested in the manner described in Example XI. As shown in FIG. 23, this testing indicated that at 600° C. and 7 vol % $O_2$, with a current bias of 3.5 μA, the response to NO was significantly larger than that to $NO_2$. FIG. 24 shows that this asymmetry held over the concentration range 20 $ppm_V \leq [NO_x] \leq 190$ $ppm_V$ at 600° C. with 7 vol % $O_2$.

Examples above indicate that embodiments of the present invention described in Examples I-IV can be used as either total $NO_x$ or selective NO sensors depending on the electrode material chosen. It is expected that a wide variety of electrode materials will be found suitable for each purpose and consider the most novel and original aspect of the embodiments in FIG. 1-4 to be the use of a single oxide electrode material, placed on a oxygen ion conductor, electrically biased to yield either "total $NO_x$" or "NO-selective" behavior. One might need to measure at least two out of three (NO, $NO_2$, $NO_x$) in order to fully characterize the $NO_x$. It can be seen that various embodiments of the present invention can achieve such measurements.

Figure 25:
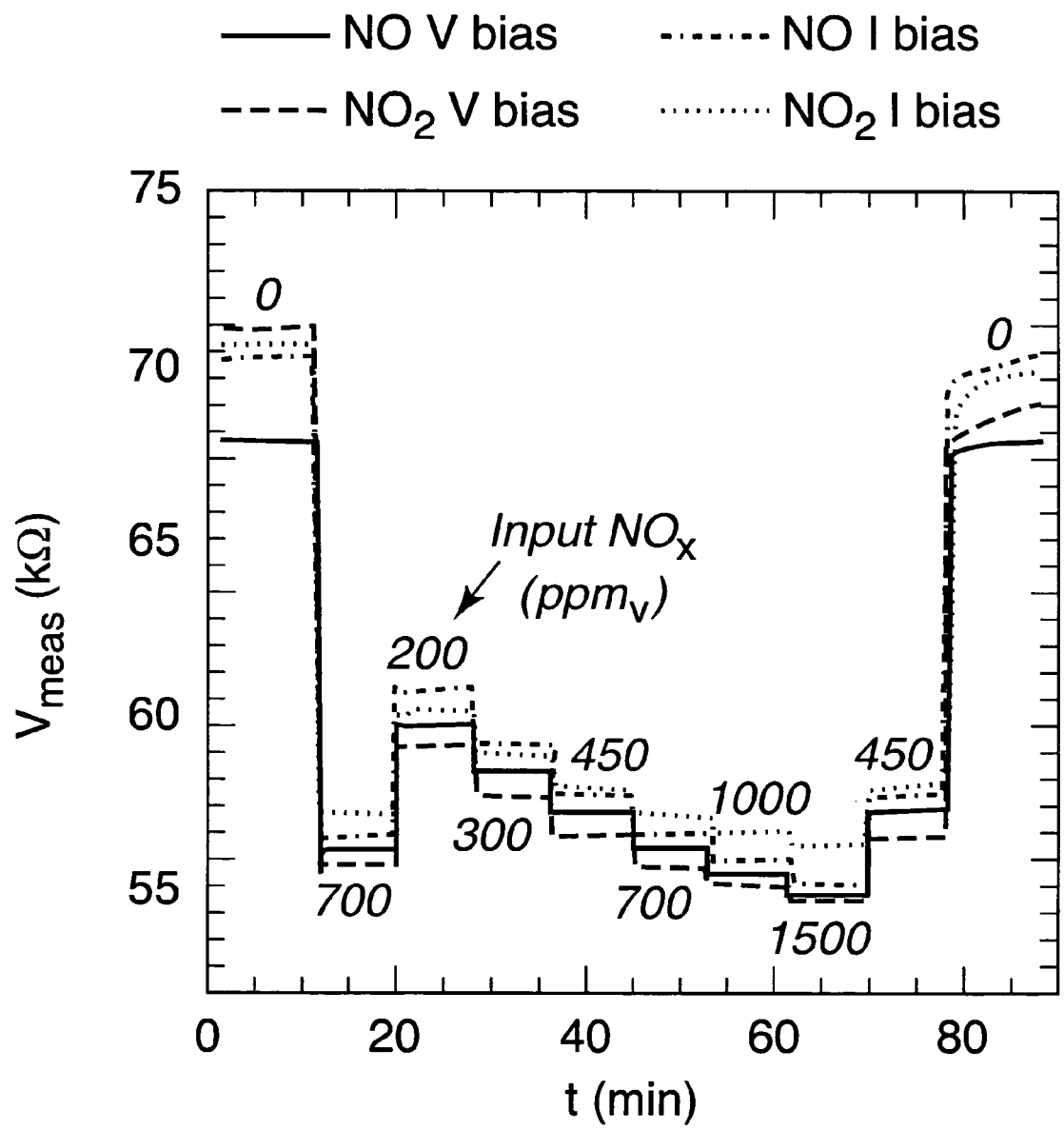
FIG. 25 is a graph showing data from testing of the present invention.

Example XVII $NO_x$ sensing devices made of $La_{0.85}Sr_{0.15}CrO_3$ on YSZ in accordance with Example III were tested as described in Example I, with the electrical connections to the device being made in accordance with FIG. 12 (current bias). Input NO and then input $NO_2$ were varied systematically (in identical fashion for the two different gases) at a fixed T of 600° C., a current bias of 5 μA, and an $O_2$ concentration of 7 vol %. The same device was then tested with the electrical connections to the device being made in accordance with FIG. 13 (voltage bias, $V_{bias}$=0.12 V, which was approximately the measured voltage with 5 μA current bias in the absence of $NO_x$). The measured currents or voltages during these four separate tests were converted to resistances using Ohm's law and are shown as a function of time in FIG. 25. This Fig. shows that the variation in resistance of the element with [NO$_x$] at 600° C. was similar irrespective of the input NO$_x$ species (NO or NO$_2$) or the method of biasing.

Example XVIII

Figure 26A:
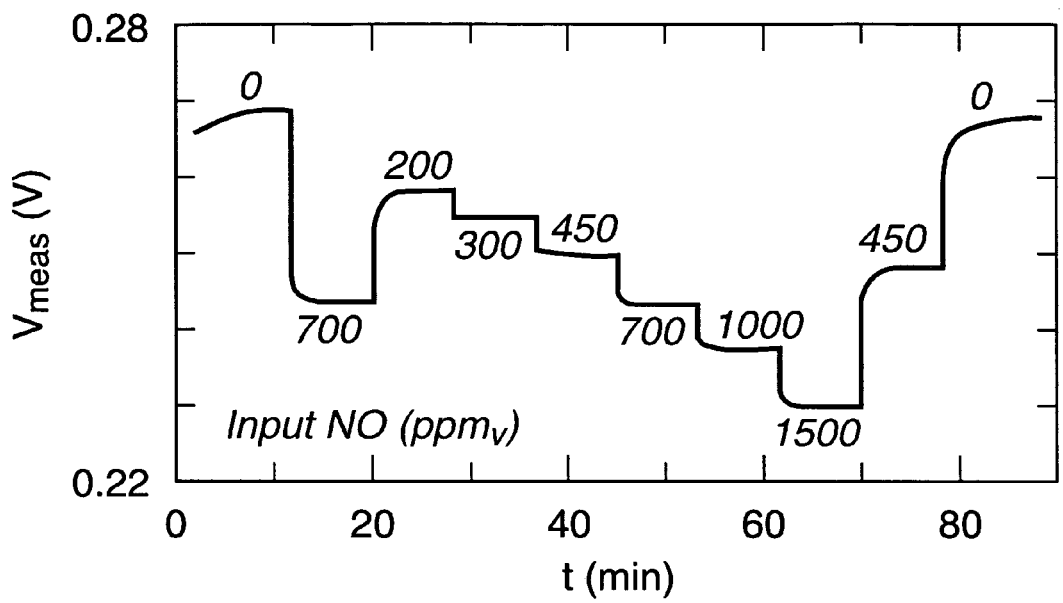
FIG. 26a is a graph showing data from testing of the present invention.
Figure 26B:
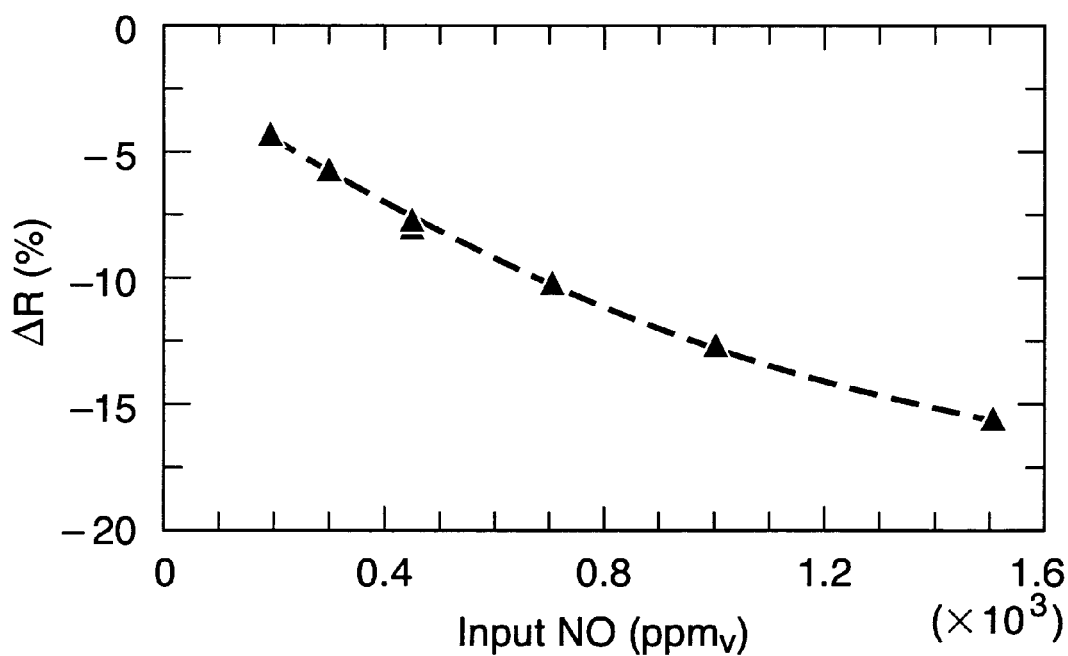
FIG. 26b is a graph showing data from testing of the present invention.

NO$_x$ sensing devices made of La$_{1.8}$Sr$_{0.2}$CoO$_4$ on YSZ in accordance with Example I were tested with the electrical connections shown in FIG. 12. Testing as was done in Example XVI was carried out to establish the "NO-selective" current biasing condition. This bias current was established and the voltage was measured as a function of time at an isotherm of 600° C. and a 7% O$_2$ concentration. As the NO concentration was varied systematically, proportional and reproducible changes in the measured voltage resulted. FIG. 26a shows the voltage measurement data, and FIG. 26b shows the measured voltages converted to resistance changes ($\Delta$R) as a function of the input NO using the formula $\Delta R = \Delta V/V_o$ where V$_0$ is the measured baseline voltage (0.268 V) with 7% O$_2$ and zero input NO, and $\Delta$V is the computed change from that baseline voltage.

Example XIX

Figure 27A:
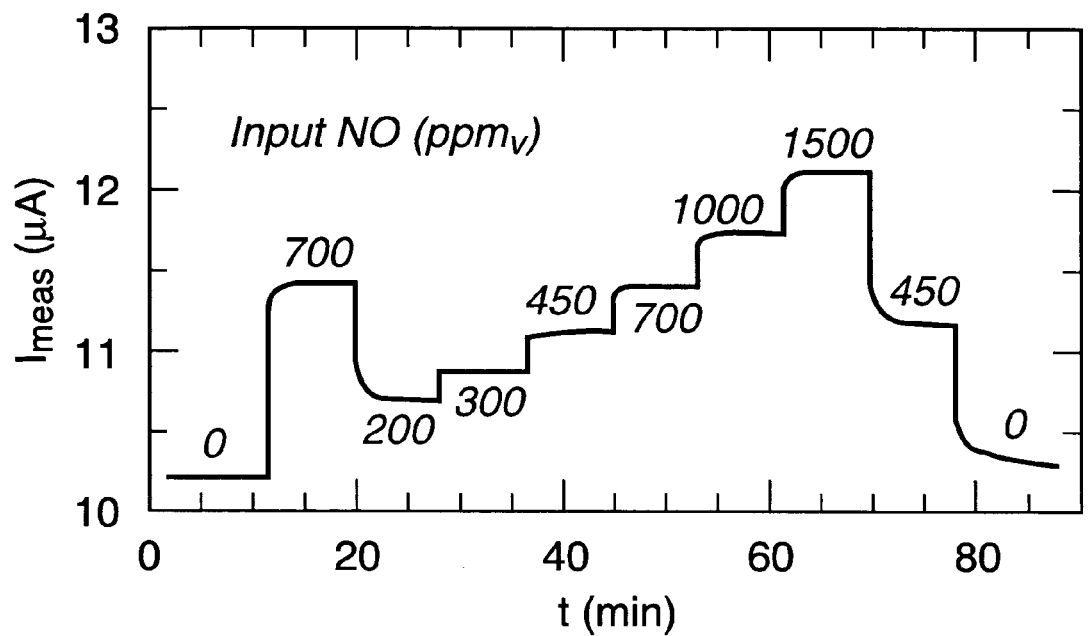
FIG. 27a is a graph showing data from testing of the present invention.
Figure 27B:
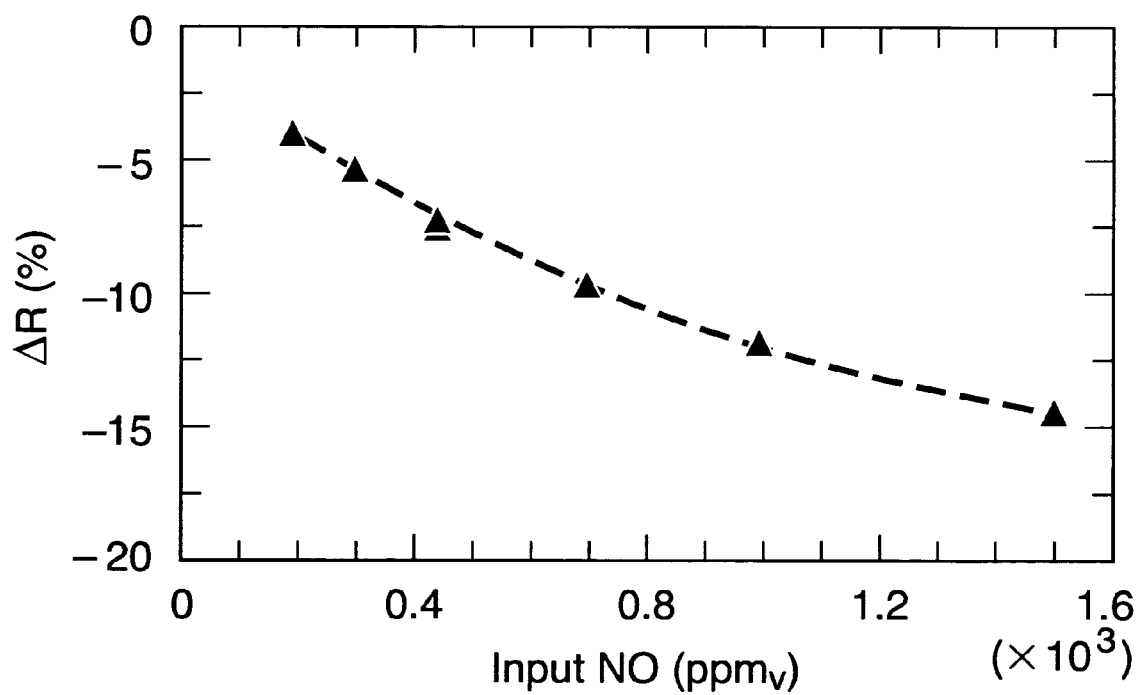
FIG. 27b is a graph showing data from testing of the present invention.

NO$_x$ sensing devices made in accordance with Example XVIII were tested as in Example XVIII, but with the electrical connections shown in FIG. 13. Analogous to Example XVII, voltage was selected to mirror V with I bias at no input NO$_x$. Current was measured as a function of time at an isotherm of 600° C. and a 7% O$_2$ concentration. As the NO concentration was varied systematically in nominally identical fashion to the prior example, proportional and reproducible changes in the measured current resulted. FIG. 27a shows the current measurement data, and FIG. 27b shows the measured currents converted to resistance changes ($\Delta$R) as a function of the input NO using the formula $\Delta R = [I_o/(I_o+\Delta I)] - 1$ where I$_o$ is the measured baseline current (10.25 µA) with 7% O$_2$ and zero input NO, and $\Delta$I is the computed change from the baseline.

It is clear from Examples XIV-XVI that the present invention, in the embodiments shown in FIG. 1-4 is useful as a current and/or voltage biased "total NO$_x$" or "NO-selective" sensing device at 600° C. The contemplated operating temperature range of sensors made in accordance with the present invention is about 450° C. to 750° C. Further, it is expected that the devices will be useful with any external electronics that can measure the DC resistance or AC impedance of the device, as examples that used both voltage and current biasing demonstrated that it is the resistance of the device that is changing in the presence of NO$_x$.

Example XX

Figure 28A:
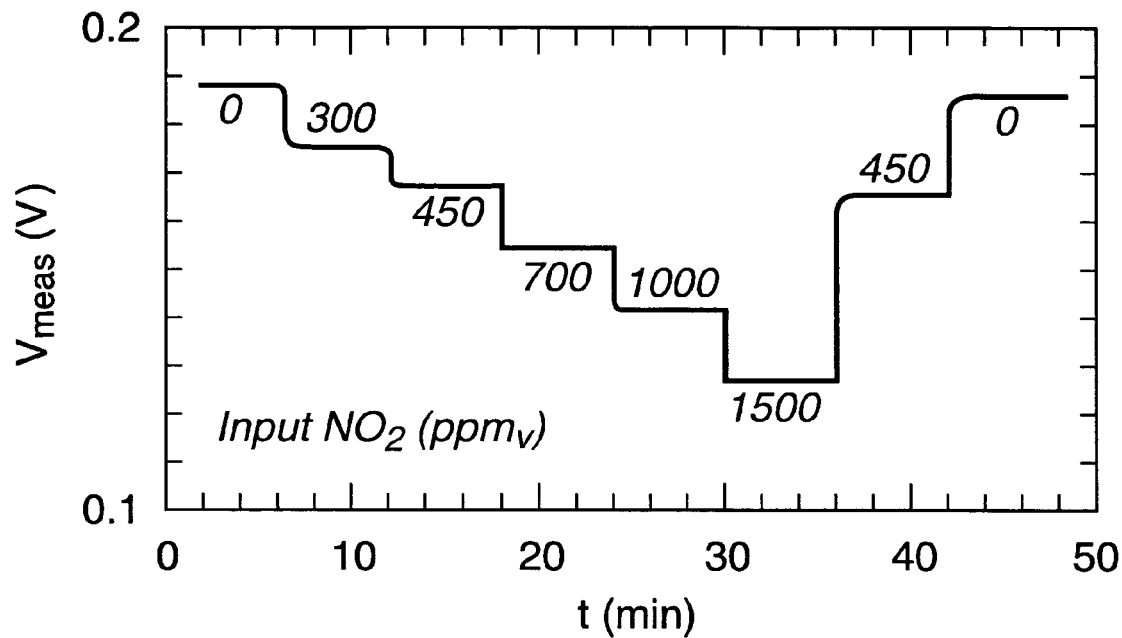
FIG. 28a is a graph showing data from testing of the present invention.
Figure 28B:
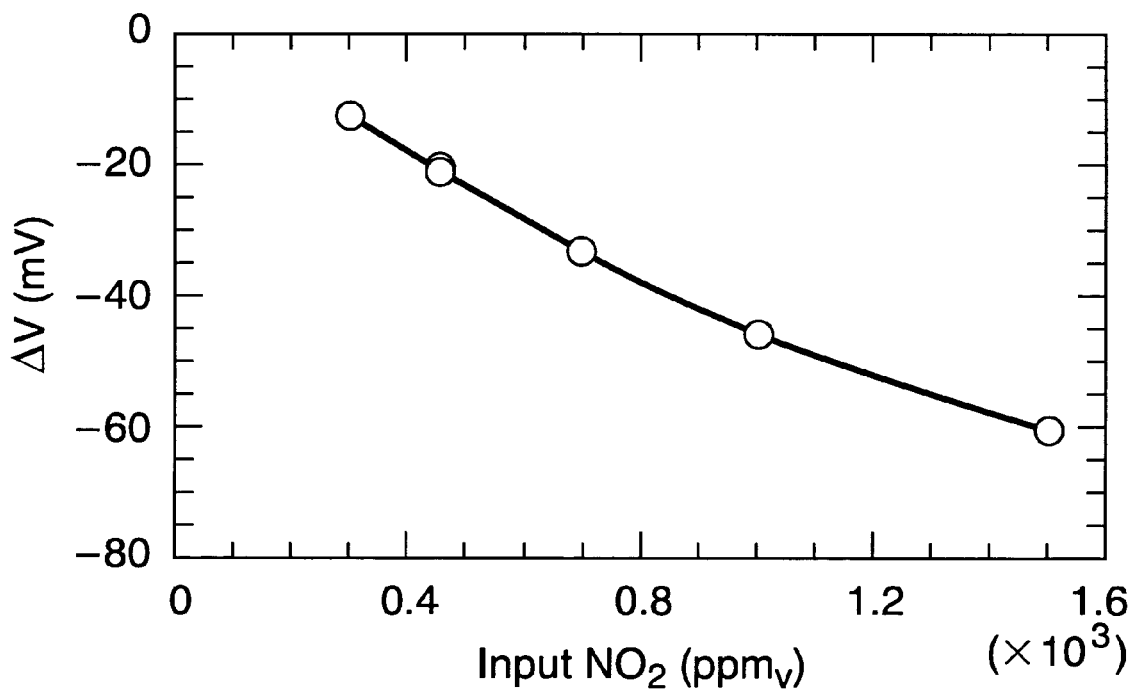
FIG. 28b is a graph showing data from testing of the present invention.

NO$_x$ sensing devices were made in accordance with Example V having La$_{0.85}$Sr$_{0.15}$CrO$_3$ (LSC) as the electronically conductive material and La$_{0.6}$Sr$_{0.4}$CO$_{0.2}$Fe$_{0.8}$O$_3$ as the overlayer. The devices were tested as described hereinabove using NO$_2$. FIG. 28a shows some typical traces of the measured voltage as the NO$_2$ concentration was varied at constant T, O$_2$, and current bias. The changes in voltage ($\Delta$V) as a function of input NO$_2$ are shown in FIG. 28b. These show that when electrically biased with a constant current, the disclosed invention is capable of producing a voltage change that is proportional to NO$_2$ concentration at 700° C.

Example XXI

Figure 29A:
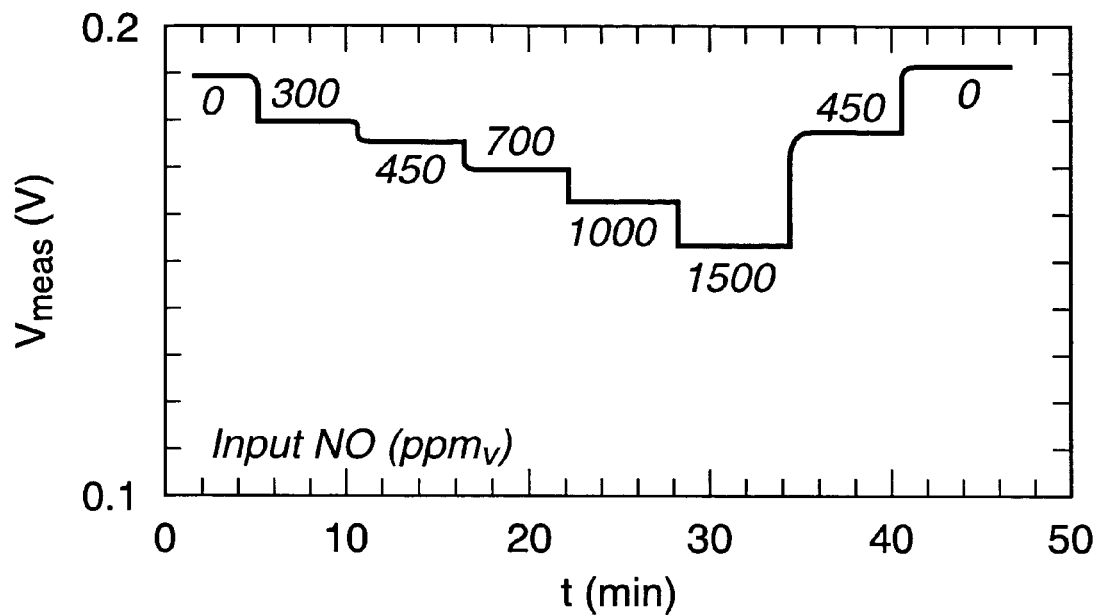
FIG. 29a is a graph showing data from testing of the present invention.
Figure 29B:
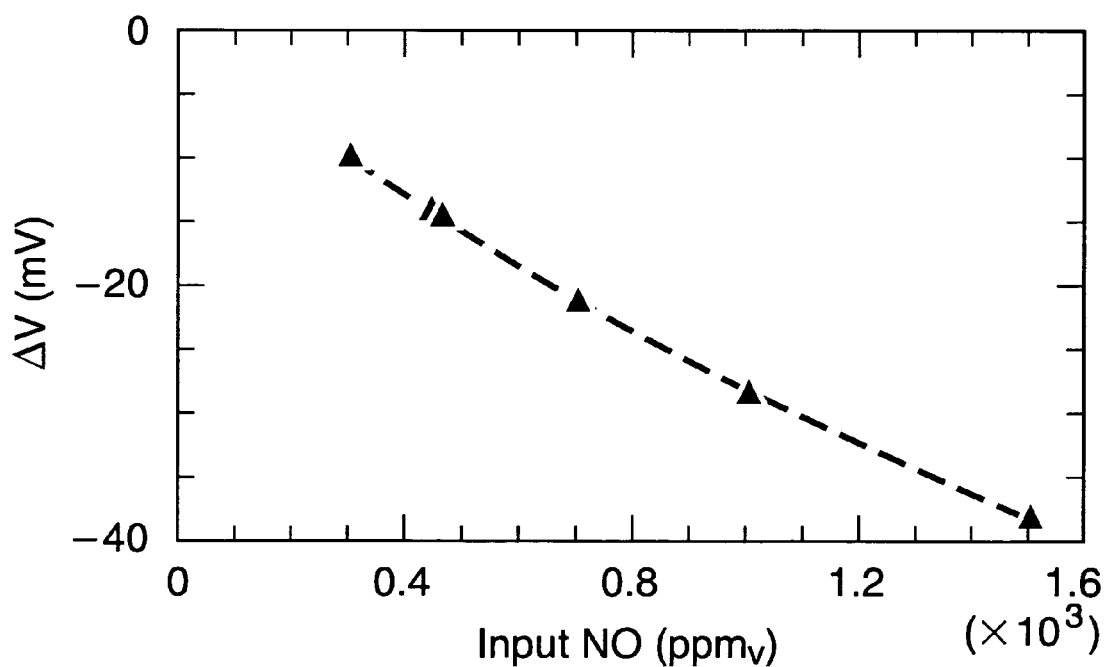
FIG. 29b is a graph showing data from testing of the present invention.

NO$_x$ sensing devices were made in accordance with Example XX and tested as described herein above using NO. FIG. 29a shows some typical traces of the measured voltage as the NO concentration was varied at constant T, O$_2$, and current bias. The changes in voltage ($\Delta$V) as a function of input NO$_2$ are shown in FIG. 29b. These data show that when electrically biased with a constant current, the disclosed invention is capable of producing a voltage change that is proportional to NO concentration at 700° C.

Example XXII

Figure 30A:
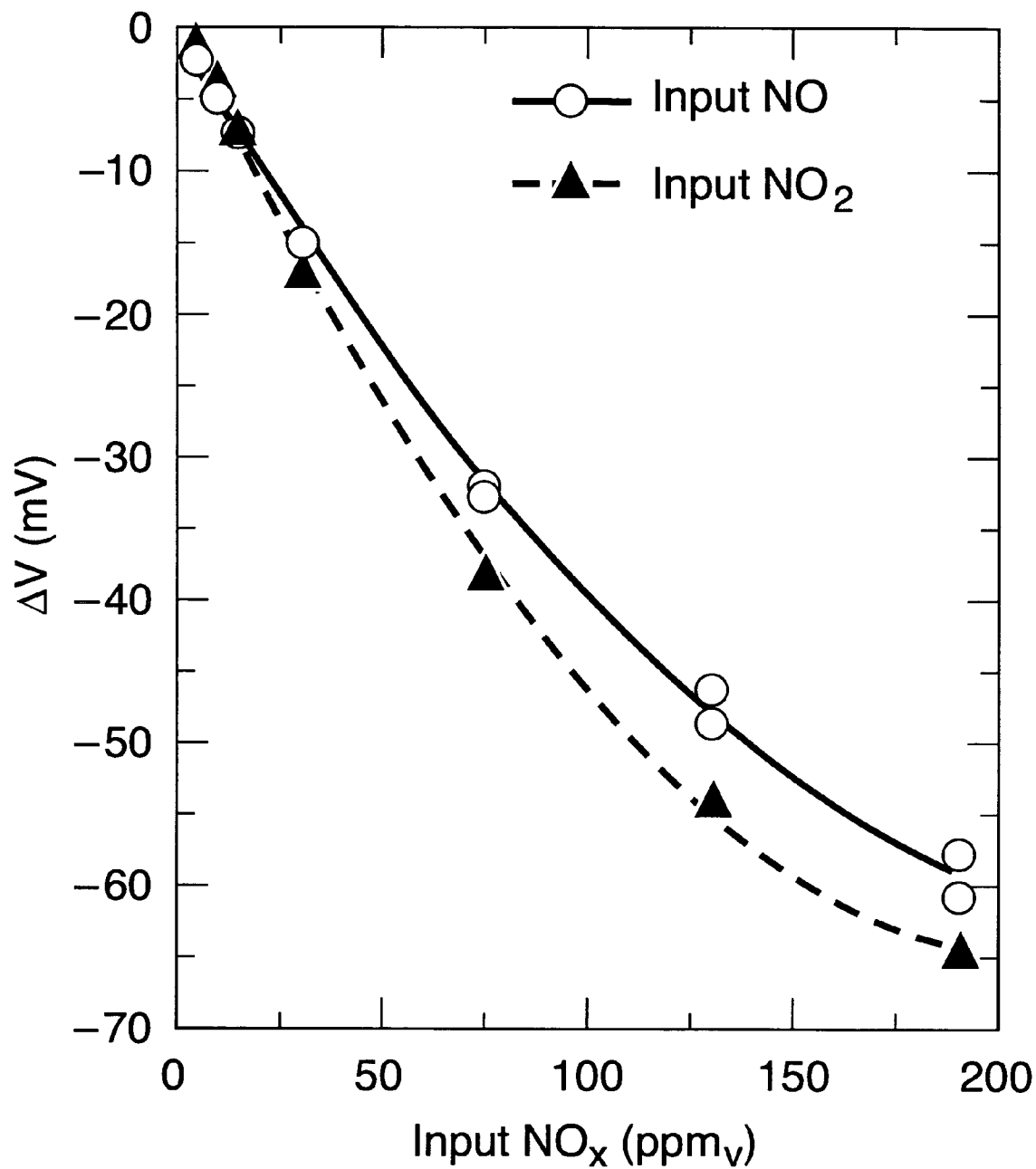
FIG. 30a is a graph showing data from testing of the present invention.
Figure 30B:
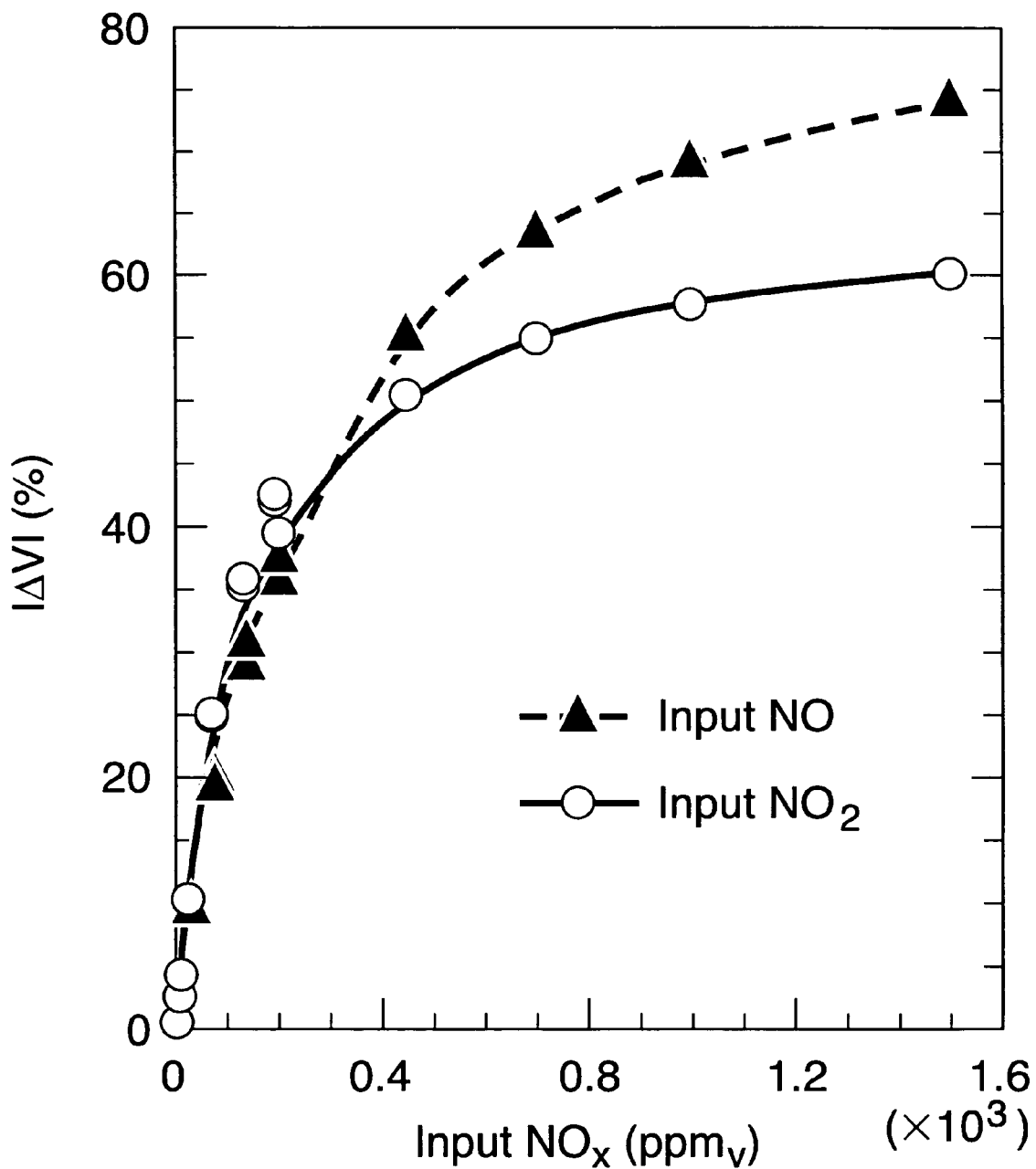
FIG. 30b is a graph showing data from testing of the present invention.

NO$_x$ sensing devices were made in accordance with Example V using La$_{0.85}$Sr$_{0.15}$CrO$_3$ as the electronically conducting layer and NiCr$_2$O$_4$ as the overlayer. The devices were tested for "Total NO$_x$" behavior over the concentration range typically found in diesel and lean-burn engine exhausts. The observed voltage changes as a function of input [NO$_x$] are shown in FIG. 30a for low input [NO$_x$]. FIG. 30b shows the percent changes in voltage. (|$\Delta$V|) due to NO$_x$ exposures in the range 5 ppm$_v \leq$ [NO$_x$] $\leq$ 1500 ppm$_v$, with the percent change defined by $\Delta V^{x\,ppm\,NOx} \equiv (V^{x\,ppm\,NOx}/V^{0\,ppm\,NOx}) \times 100$. Results shown in FIGS. 30a, 30b indicate that response to NO and NO$_2$ is nearly identical, particularly at low NO$_x$.

Example XXIII

Figure 31A:
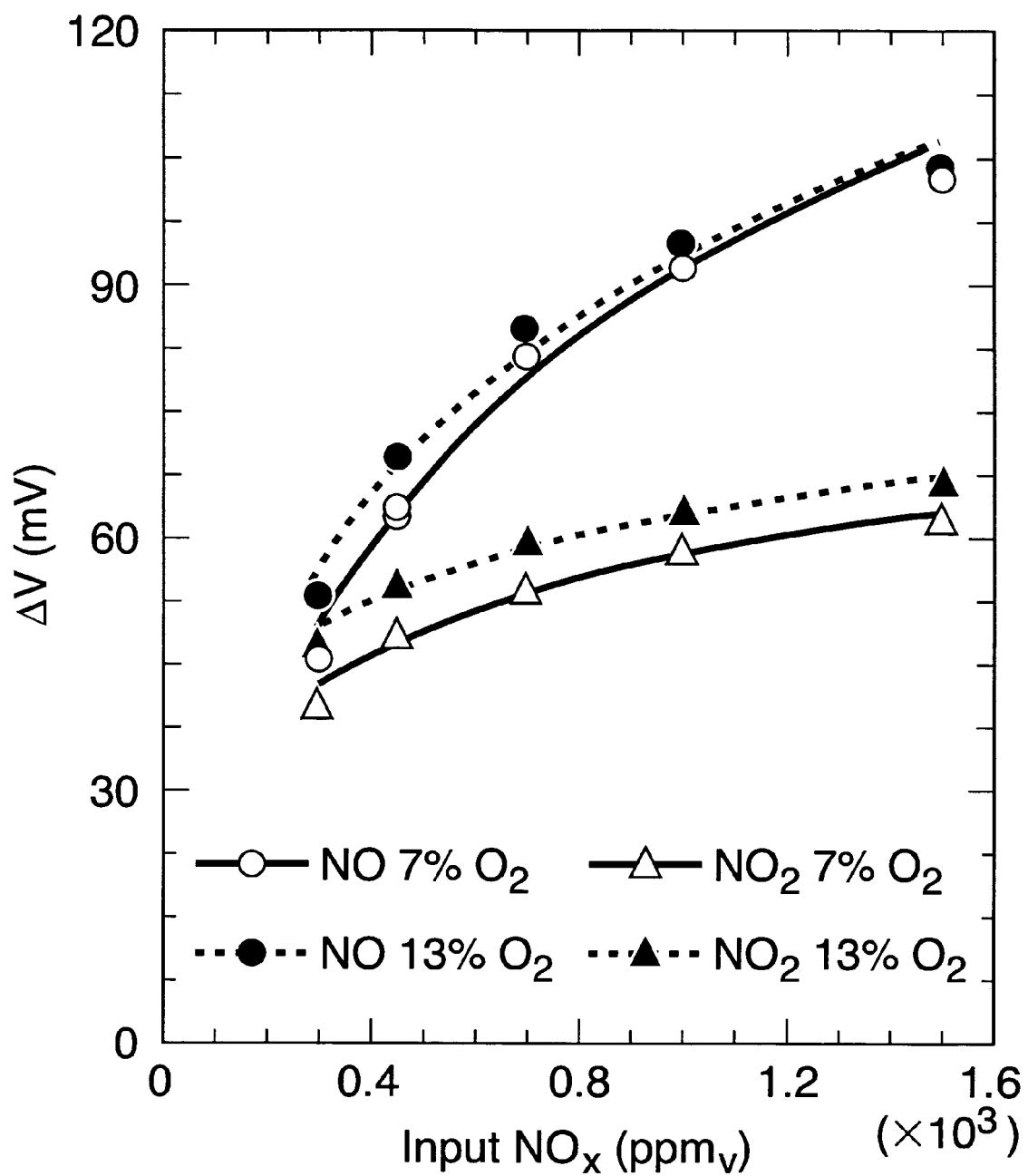
FIG. 31a is a graph showing data from testing of the present invention.
Figure 31B:
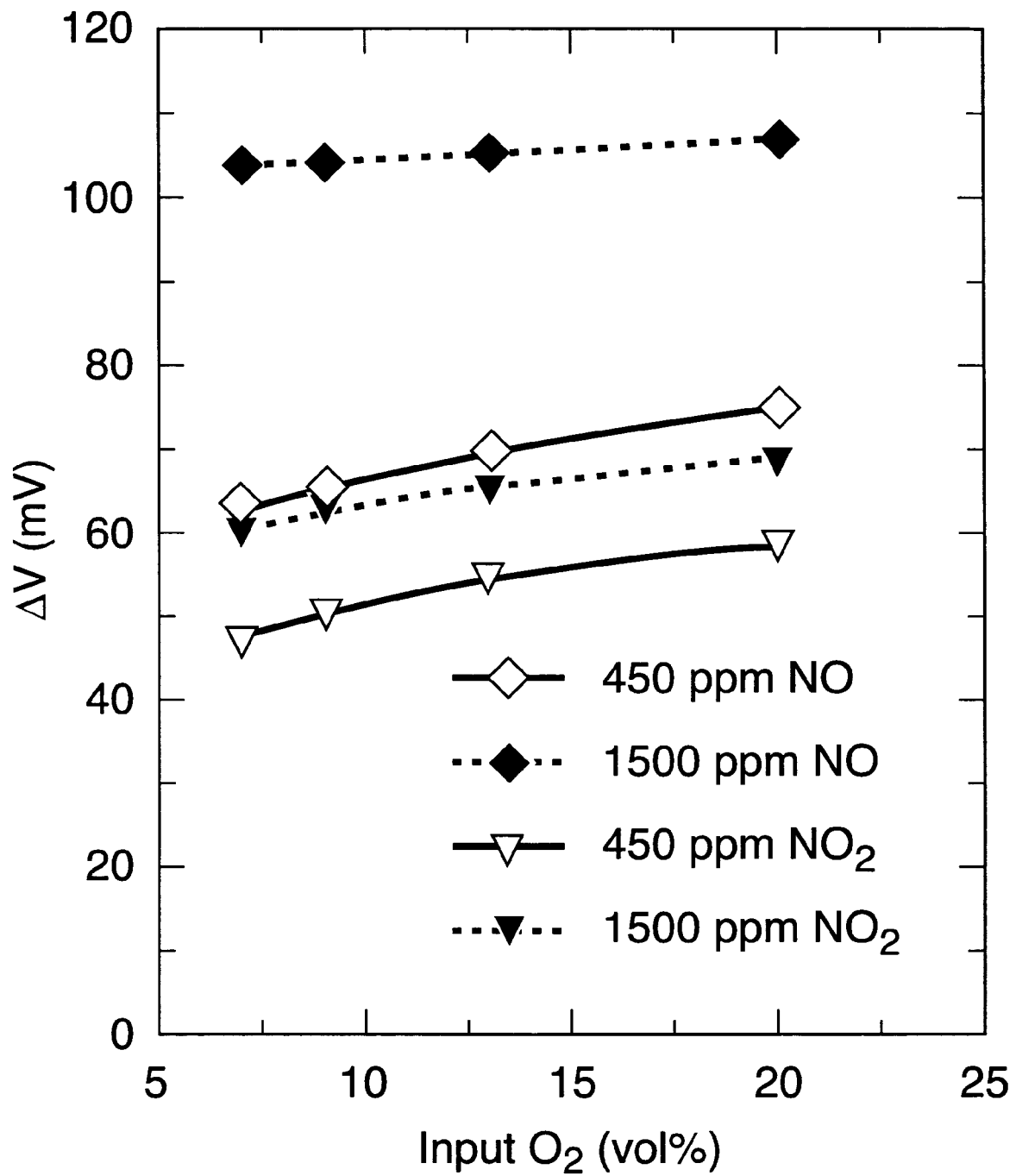
FIG. 31b is a graph showing data from testing of the present invention.

NO$_x$ sensing devices were made in accordance with Example VI using La$_{0.85}$Sr$_{0.15}$CrO$_3$, as the electronically conducting layer of both electrodes, La$_{0.6}$Sr$_{0.4}$CO$_{0.2}$Fe$_{0.8}$O$_3$ as the overlayer on one electrode, and NiCr$_2$O$_4$ as the overlayer on the other electrode. The devices were tested for "Total NO$_x$" behavior. As shown in FIG. 31a, response to NO and NO$_2$ were similar. Further, FIG. 31b shows that O$_2$ sensitivity was low.

Prior three examples show that geometries of FIGS. 5 and 6 can yield "total NO$_x$" behavior wherein LSC is used as the conducting material, either alone or with various overlayers. Similar behavior is expected for other conducting oxides described herein. Advantage of multi-layered approach may be to alter catalytic activity, or offer filtration, or bring gases over one electrode to equilibrium, or selectively adsorb one or more species.

Example XXIV

Figure 32A:
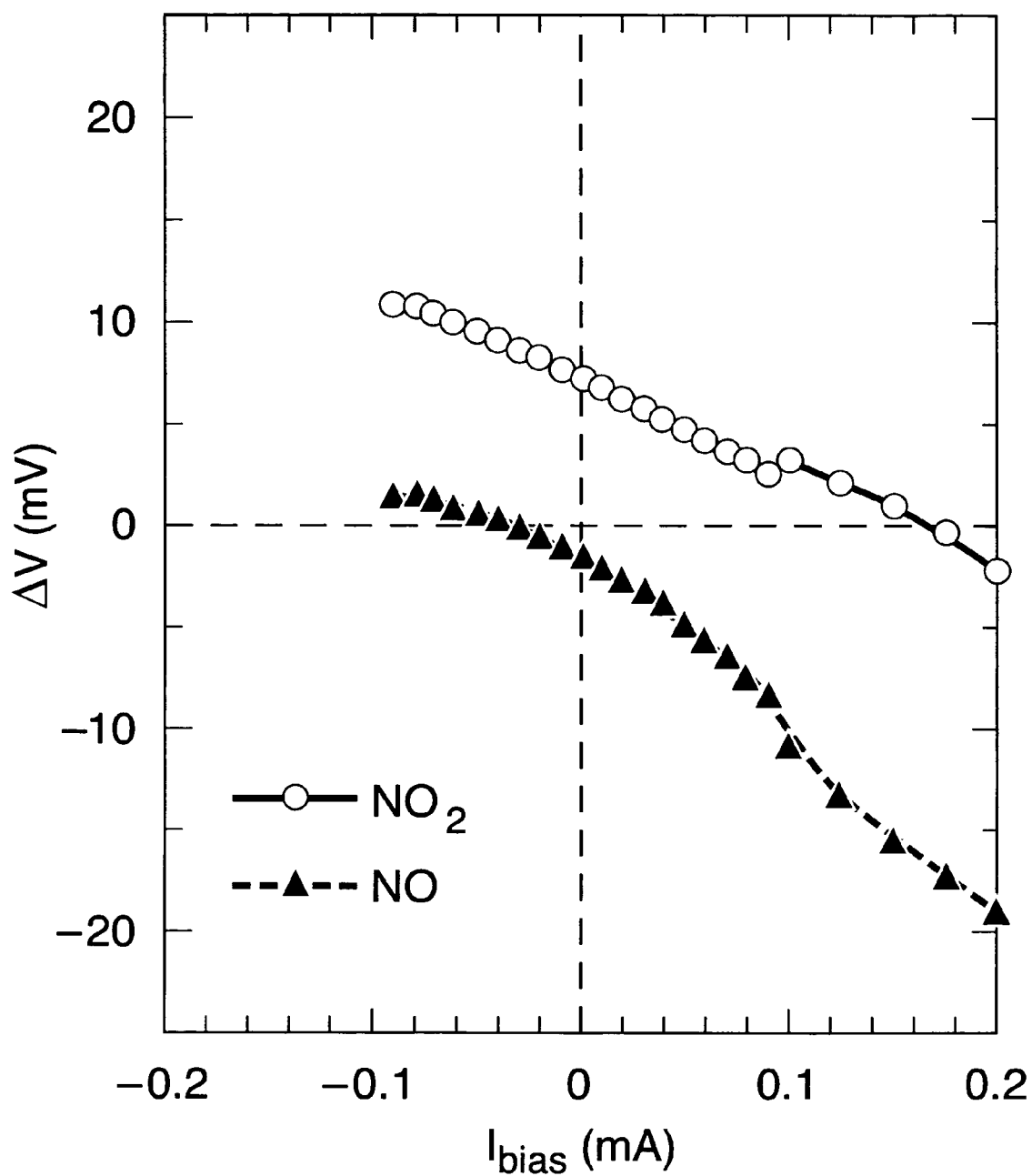
FIG. 32a is a graph showing data from testing of the present invention.
Figure 32B:
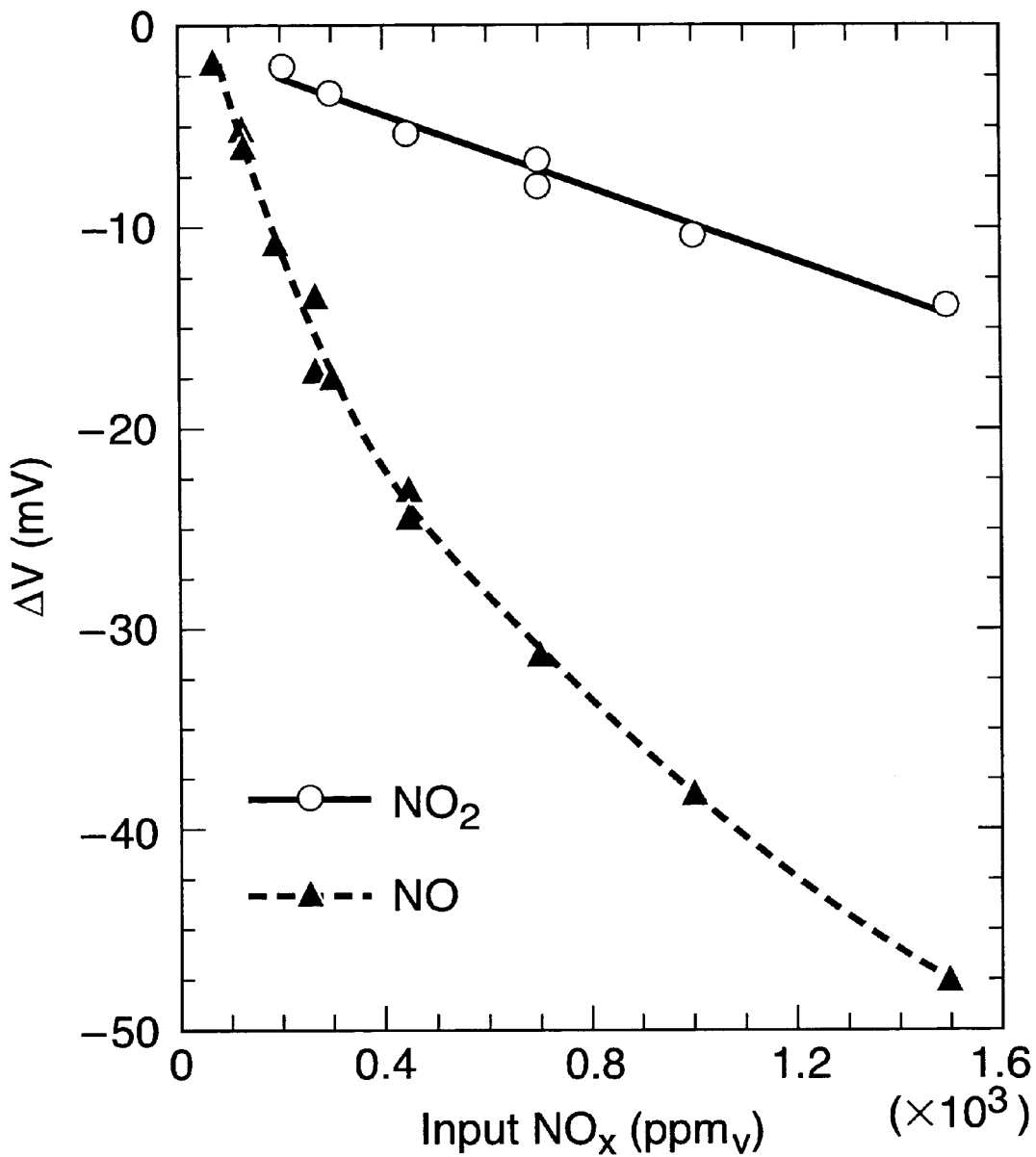
FIG. 32b is a graph showing data from testing of the present invention.

NO$_x$ sensing devices were made in accordance with Example V using Pt as the electronically conducting material and CuWO$_4$ as the overlayer. FIG. 32a shows the changes in measured voltage (as a function of I$_{bias}$) induced by 450 ppm$_v$ of NO and NO$_2$ in 93% N$_2$/7% O$_2$. At biases near +0.18 mA, the introduction of NO$_2$ resulted in little voltage change while the introduction of NO resulted in significant voltage change. FIG. 32b shows that this asymmetry held over the concentration range 30 ppm$_v \leq$ [NO$_x$] $\leq$ 1500 ppm$_v$, so this sensing element is useful as a selective NO sensor for diesel and lean-burn engine exhausts.

Example XXV

Figure 33A:
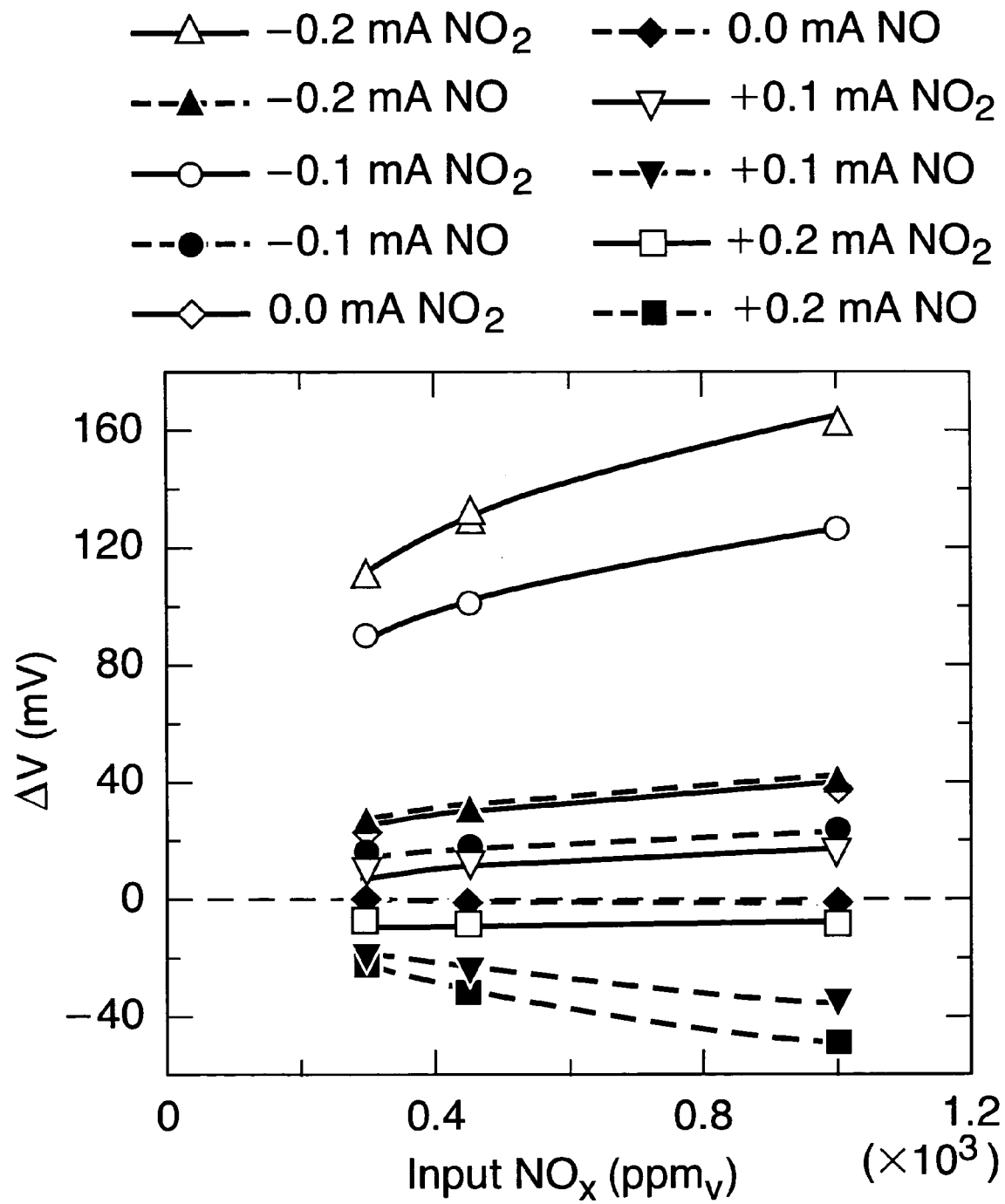
FIG. 33a is a graph showing data from testing of the present invention.
Figure 33B:
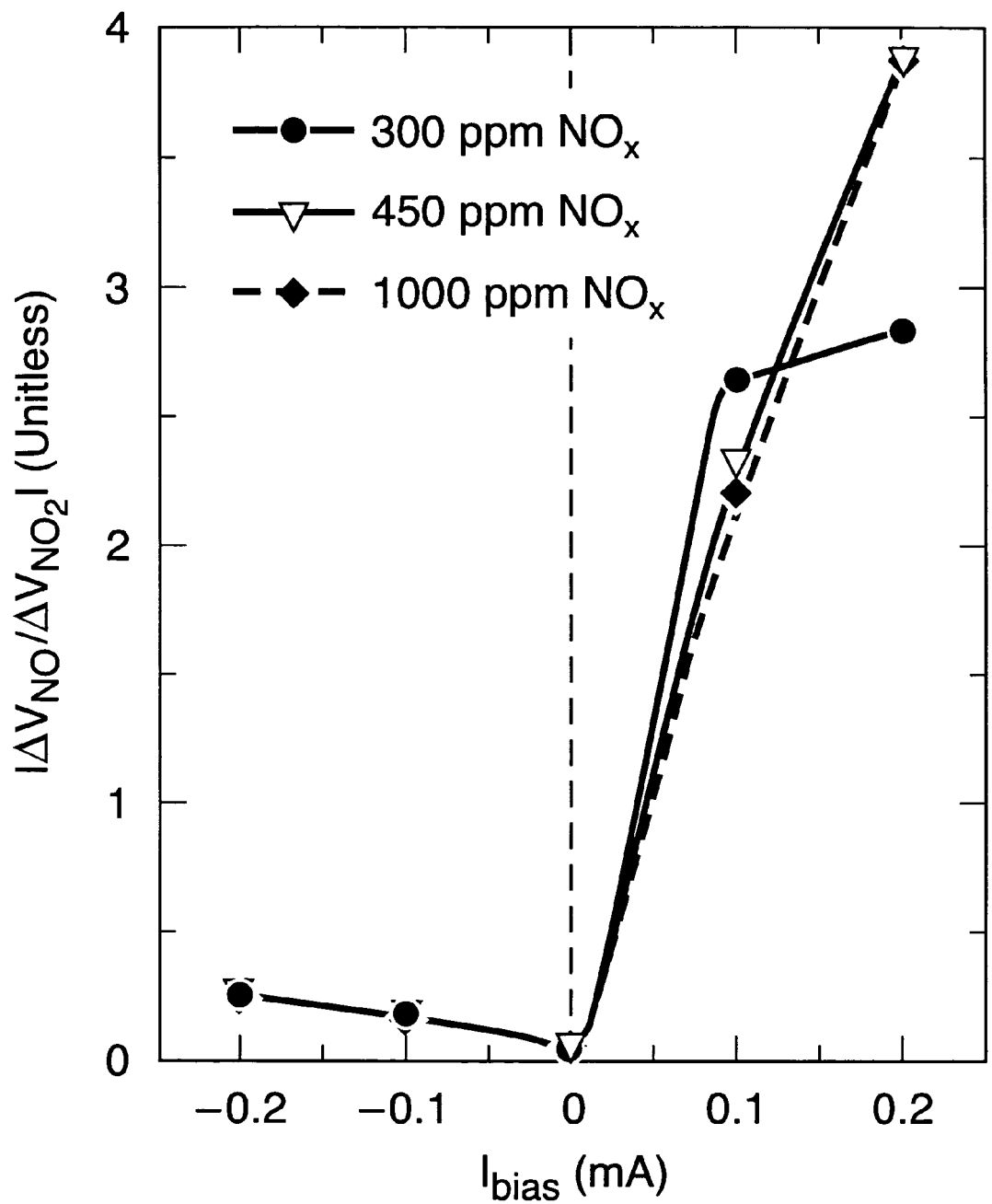
FIG. 33b is a graph showing data from testing of the present invention.

NO$_x$ sensing devices were made in accordance with Example V using Pt as the electronically conducting material and NiCr$_2$O$_4$ as the overlayer. "NO-selective" behavior was also observed this device. FIG. 33a shows the changes in measured voltage at 3 different NO$_x$ levels for biases of ±0.2, ±0.1, and 0.0 mA. At negative and zero biases, as shown in FIG. 33b, the response to NO$_2$ overwhelms that for NO. However, at positive biases, the NO response becomes much larger than the NO$_2$ response, which is qualitatively similar to the behavior seen in FIG. 32b.

Example XXVI

Figure 34:
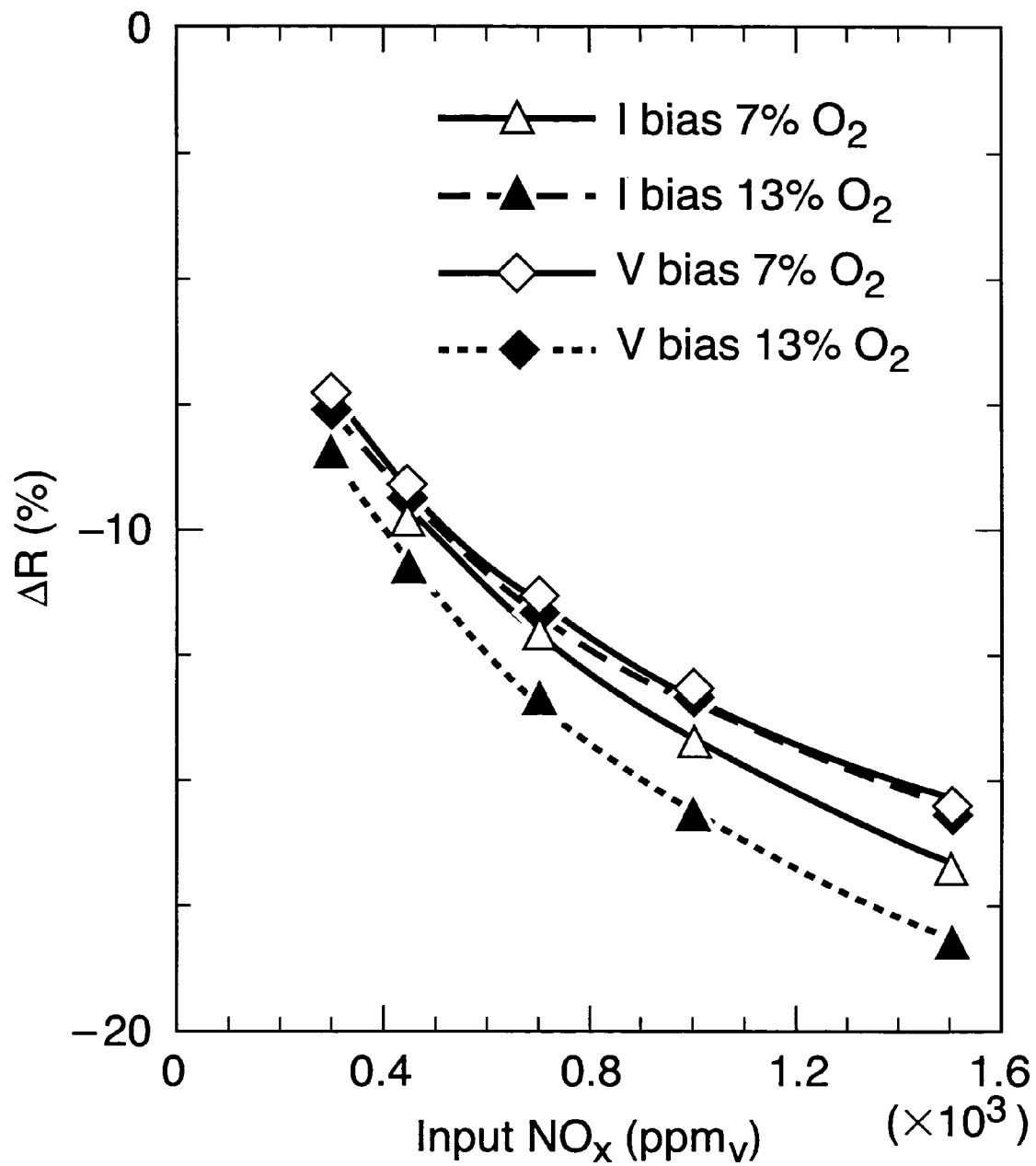
FIG. 34 is a graph showing data from testing of the present invention.
Figure 35:
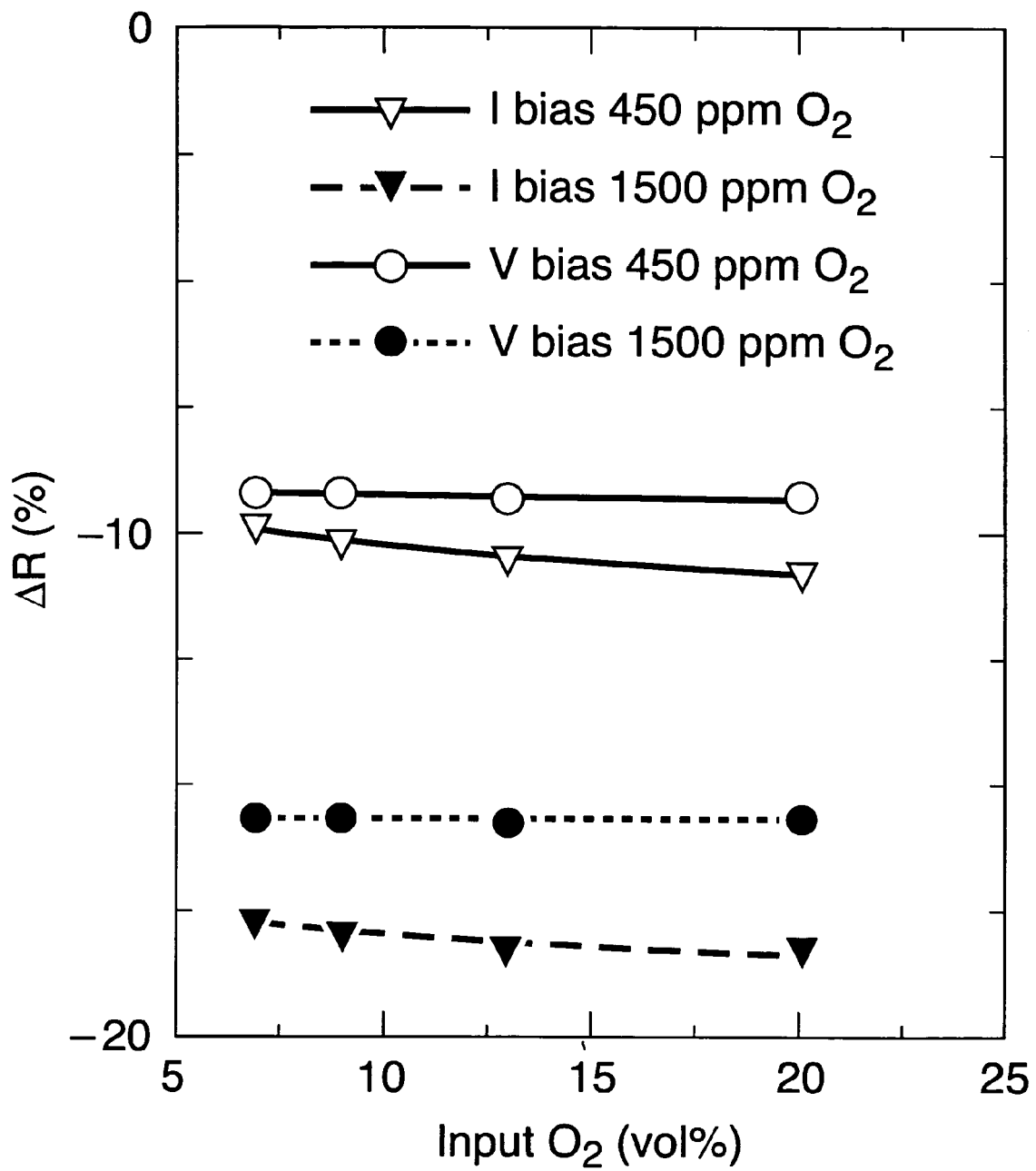
FIG. 35 is a graph showing data from testing of the present invention.

NO$_x$ sensing devices made in accordance with Example XXV were tested for NO sensitivity at 600° C. with both current and voltage bias conditions as detailed earlier in example XVII. The measured sensing responses to NO are plotted in FIG. 34 as resistance changes, with the changes in resistance computed in identical fashion to examples XVIII and XIX. This Fig. shows as was seen before, the resistance of the element is changing with NO, so any electronics that can measure resistance or impedance can be used to exploit the disclosed invention. It is important to point out that this sensing element, particularly when voltage biased, displayed very little [O$_2$] sensitivity, as shown in FIG. 35, since exhaust from diesel and lean burn engines is often of varying oxygen content.

Above examples demonstrated that geometry of FIG. 5 can give "NO-selective" behavior when conductive layer is Pt, and overcoat is a trans. metal oxide. This is expected to be true even if conductive layer is another noble metal or alloy, if the conductive layer on the bottom is different for each side, etc. Moreover, the sensing capability is generally independent of the amount of O$_2$ present.

It is important to the aim and scope of the present invention to realize that measuring the sensor resistance (by biasing) has enhanced the element response to nitric oxide (NO). The devices disclosed herein are intended for measurement of NO$_x$ (NO+NO$_2$) at temperatures in the range 450 to 750° C., and as Table I below shows, NO is the dominant equilibrium NO$_x$ species in this temperature range, particularly at the higher temperature portion. Table I shows the calculated equilibrium mole fraction of NO ($x_{NO}$, $=n_{NO}/(n_{NO}+n_{NO_2})$) in mixtures of N$_2$, O$_2$, NO and NO$_2$.

TABLE I

| T (° C.) | $x_{NO}$ (3.3 mol % O$_2$) | $x_{NO}$ (21 mol % O$_2$) |
|---|---|---|
| 300 | 0.20 | 0.09 |
| 400 | 0.61 | 0.38 |
| 500 | 0.86 | 0.71 |
| 600 | 0.94 | 0.87 |
| 700 | 0.98 | 0.94 |
| 800 | 0.99 | 0.97 |

Example XXVII

Figure 36:
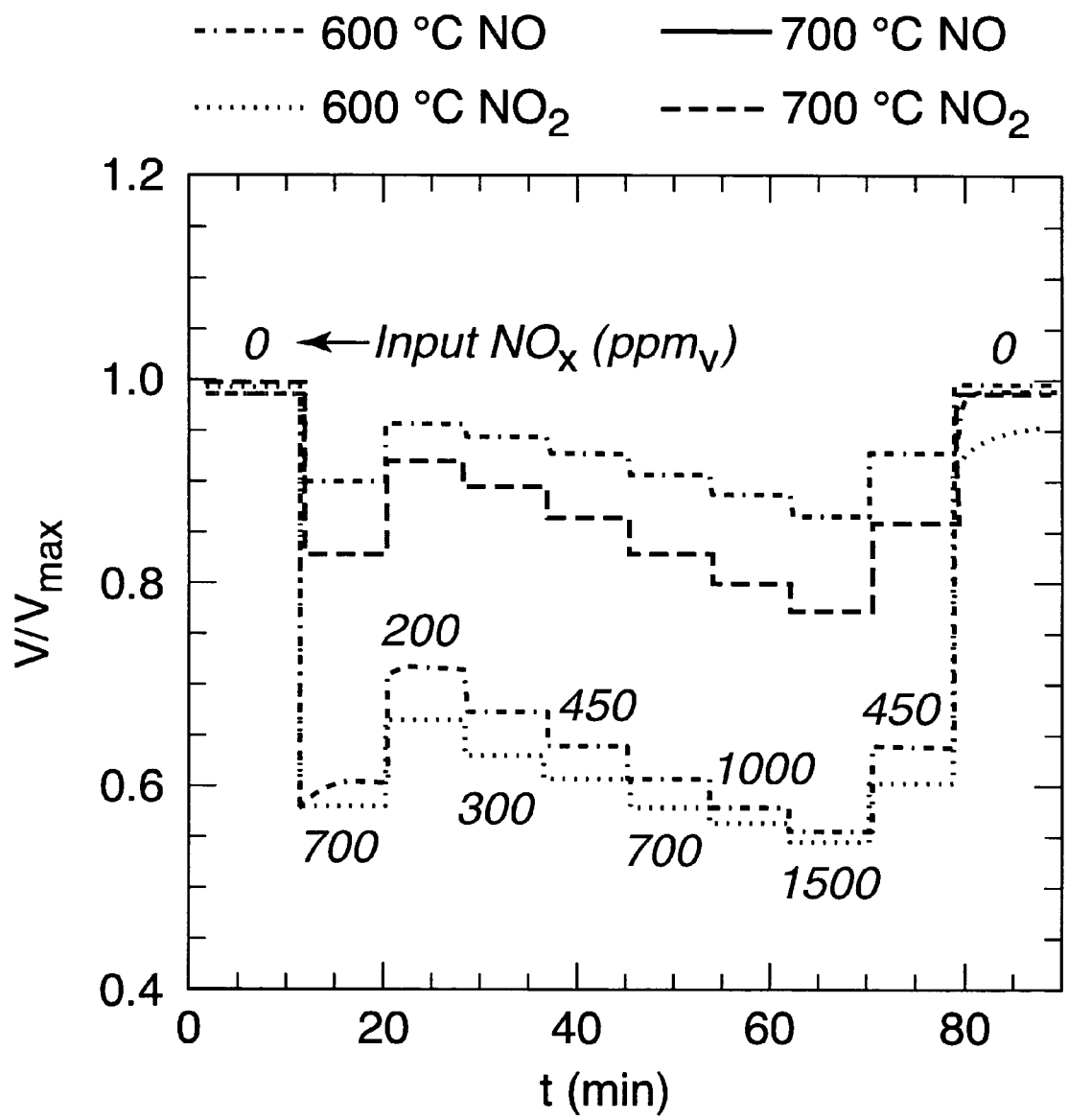
FIG. 36 is a graph showing data from testing of the present invention.

Sensing devices using La$_{0.85}$Sr$_{0.15}$CrO$_3$ (LSC) and YSZ on Al$_2$O$_3$, were made in accordance with Example VII and the bias that gave "total NO$_x$" sensing behavior was determined as detailed in Example XI at two different temperatures (600° C. and 700° C.). FIG. 36 shows how the measured voltage varied with [NO$_x$] when the temperature was held constant (at 600° C. and 700° C.) and the O$_2$ concentration was fixed at 7 vol %. This data indicates that thick-film configurations can serve as total NO$_x$ sensors.

In some embodiments of the present invention, one electrode is made of a conductive oxide and the other electrode consists essentially of a conductive metal, such as a noble metal, for example. FIGS. 8, 9 show examples of these embodiments.

Example XXVIII

Figure 37:
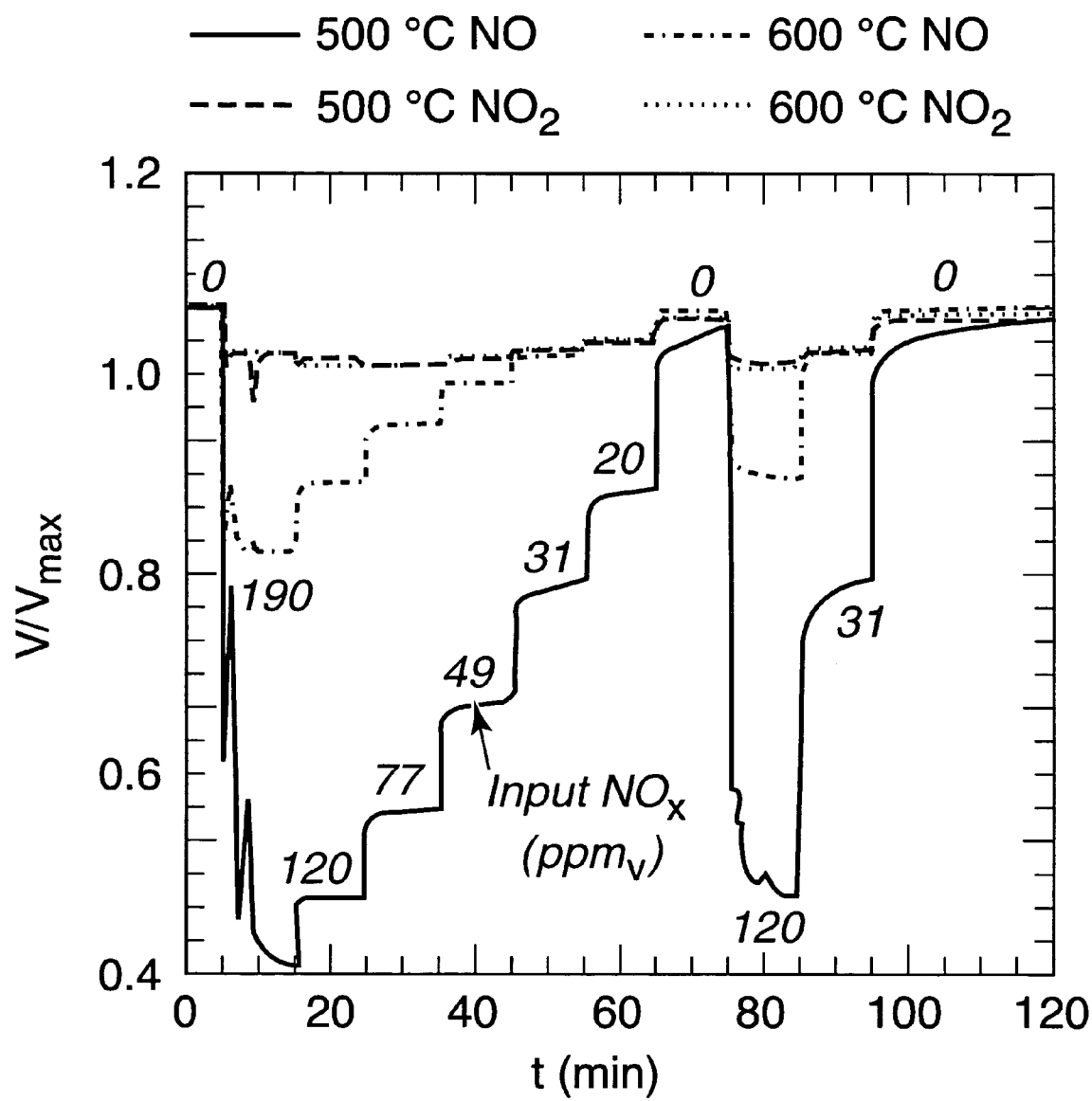
FIG. 37 is a graph showing data from testing of the present invention.

Sensing devices using La$_{0.85}$Sr$_{0.15}$CrO$_3$ (LSC) and Pt on YSZ, were made in accordance with Example VIII and the bias that gave NO-selective sensing behavior was determined as detailed in Example XVI at two different temperatures (500° C. and 600° C.). FIG. 37 shows how the measured voltage varied with [NO$_x$] when the temperature was held constant (at 500° C. and 600° C.) and [O$_2$] was fixed at 7 vol %, with the bias that gave "NO-selective" behavior.

Example XXIX

Figure 38:
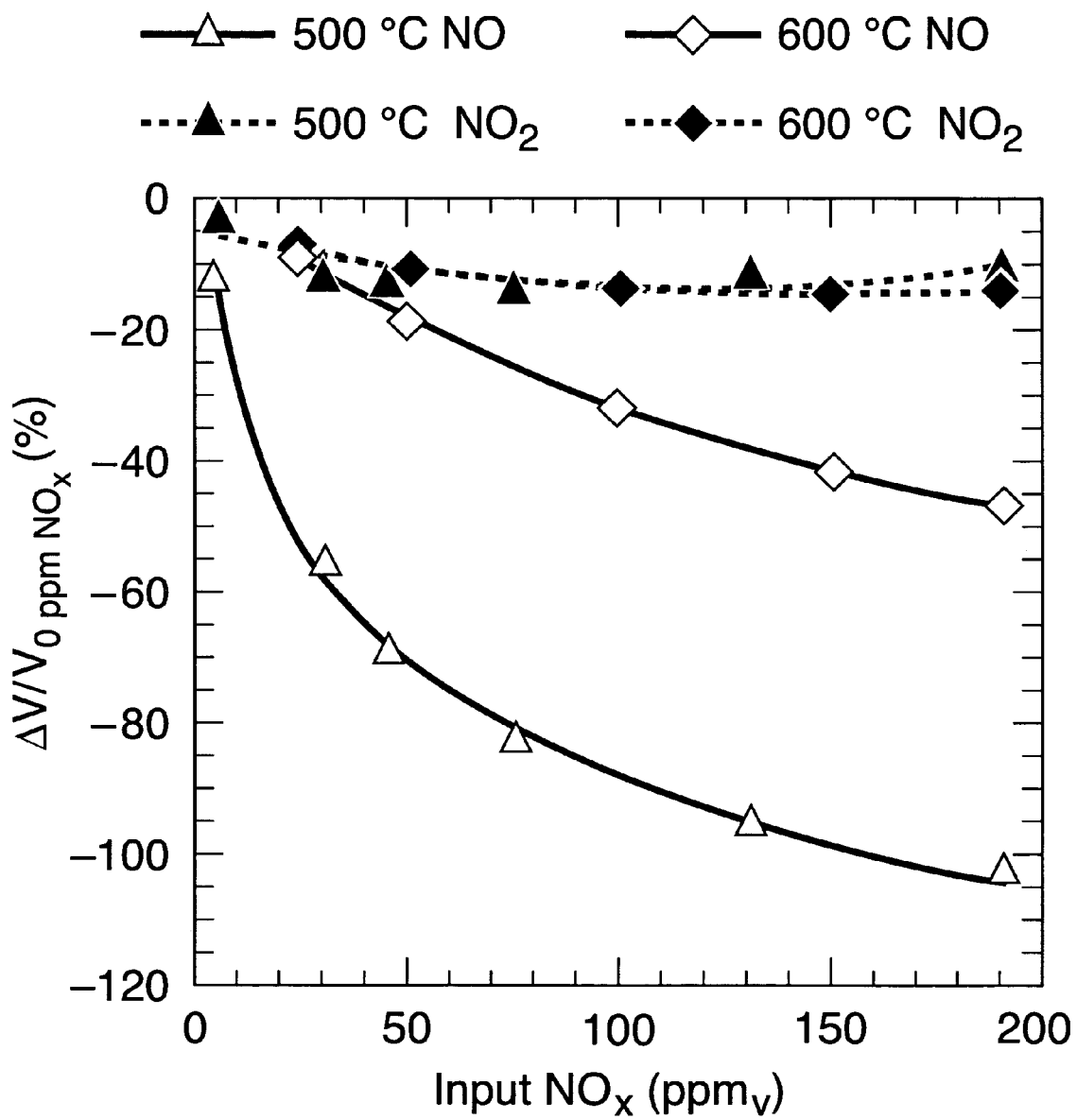
FIG. 38 is a graph showing data from testing of the present invention.

Sensing devices using La$_{0.85}$Sr$_{0.15}$CrO$_3$ (LSC) and Pt on YSZ, were made in accordance with Example IX and the bias that gave NO-selective sensing behavior was determined as detailed in Example XVI at 600° C.). FIG. 38 shows how the measured voltage varied with [NO$_x$] when the temperature was held constant (at 600° C.) and the O$_2$ concentration was fixed at 7 vol %.

Prior two examples showed how the use of a transition metal oxide and Pt allowed "NO-selective" sensing with bias.

It is often desirable in carrying out the present invention to use a noble metal as a means for facilitating electrical connections to conductive oxide electrode materials.

The present invention has demonstrated utility in NO$_x$ monitoring and remediation for diesel lean burn gasoline engines. The sensing elements disclosed herein might have use in NO$_x$ sensors for diesel and lean-burn gasoline engines, and in other applications where a compact and simple NO$_x$ sensor operating at elevated temperatures might be called for.

While there has been shown and described what are at present considered the preferred embodiments of the invention, it will be obvious to those skilled in the art that various changes and modifications can be prepared therein without departing from the scope of the inventions defined by the appended claims.

What is claimed is:

1. A NO$_x$ sensing device comprising:
   (i) at least two electrodes wherein both electrodes comprise the same conductive oxide material, at least one electrode is configured for sensing NO$_x$ gas, and both electrodes are exposed to the same sample gas,
   (ii) an oxygen-ion conducting material in bridging electrical communication with said electrodes, said device being configured to sense at least one chemical selected from the group consisting of NO and NO$_2$ when the device is biased at a selected electrical bias, and
   (iii) an electronics package including a means for measuring an electrical property between the first electrode and the second electrode, and an electrical biasing source for electrically biasing the sensing device, the electrical biasing source configured to produce a selected electrical bias between the first and second electrode, the electrical biasing source configured to produce the selected electrical bias, wherein the means for measuring an electrical property is selected from the group consisting of a voltmeter, an ammeter, and a combination thereof, and wherein the selected electrical bias is selected from the group consisting of electric current, voltage, and a combination thereof.

2. A NO$_x$ sensing device in accordance with claim 1 wherein said conductive oxide comprises at least one composition selected from the group consisting of Y$_{1-x}$A$_x$M$_{1-z}$M'$_z$O$_3$ and Ln$_{1-y}$A$_y$M$_{1-z}$M'$_z$O$_3$, wherein Ln is an element selected from the group consisting of La, Ce, Pr, Nd, Sm, Eu, Gd, Th, Dy, Ho, Er, Tm, Yb, Lu, wherein A is an element selected from the group consisting of Mg, Ca, Sr, Ba, wherein M is an element selected from the group consisting of Sc, Ti, V, Cr, Mn, Fe, Co, Ni, Cu, Zn, wherein M' is an element selected from the group consisting of Sc, Ti, V, Cr, Mn, Fe, Co, Ni, Cu, Zn) and wherein $0 \leq x \geq 0.4$, $0 \leq y \geq 0.4$, and $0 \leq z \geq 1$.

3. A $NO_x$ sensing device in accordance with claim 1 wherein said oxygen-ion conducting material comprises a substrate upon which said electrodes are supported.

4. A $NO_x$ sensing device in accordance with claim 1 further comprising a dielectric substrate that supports said oxygen-ion conducting material and said electrodes.

5. A $NO_x$ sensing device in accordance with claim 1 wherein at least one of said electrodes further comprises a first layer and an overlayer covering at least a portion of said first layer.

6. A $NO_x$ sensing device in accordance with claim 5 wherein said overlayer comprises a conductive oxide.

7. A $NO_x$ sensing device in accordance with claim 6 wherein said conductive oxide comprises at least one material selected from the group consisting of: $Y_{1-x}A_xM_{1-z}M'_zO_3$ and $Ln_{1-y}A_yM_{1-z}M'O_3$, wherein Ln is an element selected from the group consisting of La, Ce, Pr, Nd, Sm, Eu, Gd, Th, Dy, Ho, Er, Tm, Yb, Lu, wherein A is an element selected from the group consisting of Mg, Ca, Sr, Ba, wherein M is an element selected from the group consisting of Sc, Ti, V, Cr, Mn, Fe, Co, Ni, Cu, Zn, wherein M' is an element selected from the group consisting of Sc, Ti, V, Cr, Mn, Fe, Co, Ni, Cu, Zn) and wherein $0 \leq x \geq 0.4$, $0 \leq y \geq 0.4$, and $0 \leq z \geq 1$.

8. A $NO_x$ sensing device in accordance with claim 5 wherein said overlayer is a first overlayer, and wherein a second of said electrodes further comprises a first layer and a second overlayer covering at least a portion of said first layer.

9. A $NO_x$ sensing device in accordance with claim 8 wherein said first overlayer and said second overlayer are essentially compositionally identical.

10. A $NO_x$ sensing device in accordance with claim 8 wherein said first overlayer and said second overlayer are essentially compositionally different.

11. A $NO_x$ sensing device in accordance with claim 1 wherein said electrodes are coplanar.

12. A $NO_x$ sensing device in accordance with claim 1 wherein said electrodes are mounted in different planes.

13. A $NO_x$ sensing device in accordance with claim 1 wherein each of said electrodes further comprises a metal that facilitates electrical connection to said electrode.

14. A $NO_x$ sensing device in accordance with claim 1 wherein said conductive oxide comprises a noble metal.

15. A $NO_x$ sensing device in accordance with claim 1 wherein said sensing device can be electrically biased to provide analytical data selective for total $NO_x$.

16. A $NO_x$ sensing device in accordance with claim 1 wherein said sensing device can be electrically biased to provide analytical data selective for total $NO_2$.

17. A $NO_x$ sensing device in accordance with claim 1 wherein said sensing device can be electrically biased to provide analytical data selective for total NO.

18. A $NO_x$ sensing device in accordance with claim 1 wherein said sensing device is operable at a temperature in the range of up to 700° C.

19. A $NO_x$ sensing device in accordance with claim 1 wherein said sensing device is operable in the presence of up to 20 volume % $O_2$.

20. An apparatus for sensing $NO_x$ gas in a sample gas which includes oxygen, the apparatus comprising:
(i) a first electrode;
(ii) a second electrode, wherein both first and second electrodes comprise a first conductive oxide material, at least one electrode is configured for sensing $NO_x$ gas, and both electrodes are exposed to the same sample gas;
(iii) an oxygen-ion conducting substrate in electrical communication with the first electrode and the second electrode, wherein the oxygen-ion conducting substrate, the first electrode, and the second electrode together define a sensing device,
(iv) the sensing device having an electrical resistance that changes in proportion to the concentration of a member selected from the group consisting of (a) NO gas only and (b) NO gas and $NO_2$ gas;
(v) an electronics package including a means for measuring an electrical property between the first electrode and the second electrode, and an electrical biasing source for electrically biasing the sensing device, the electrical biasing source configured to produce a selected electrical bias, and
(vi) the sensing device made of materials that change in electrical resistance in proportion to local concentration changes in a member selected from the group consisting of (1) NO gas and (2) NO gas and $NO_2$ gas, when the sensing device is biased at the selected electrical bias, so that the change in electrical resistance of the sensing device while electrically biased indicates the local concentration of either (1) NO gas only or (2) NO gas and $NO_2$ gas in the sample gas which includes oxygen.

21. The apparatus of claim 20 wherein the oxygen-ion conducting material comprises at least one material selected from the group consisting of YSZ, $Mg_{1-a}Zr_aO_2$, $La_{2-b}Sr_bMo_2O_9$, $La_{2-b}Ba_bMo_2O_9$, $La_2MO_{2-e}Nb_eO_9$, $La_2Mo_{2-e}Ta_eO_9$, and $La_2Mo_{2-e}W_eO_9$ where $0<a<0.2$, $0<b<0.3$, $0<c<0.3$, $a+d<0.3$, and $0<e<1$.

22. The apparatus of claim 20 wherein the first conductive oxide material comprises at least one material selected from the group consisting of $Y_{1-x}A_xM_{1-z}M'_zO_3$ and $Ln_{1-y}A_yM_{1-z}M'_zO_3$, wherein Ln is an element selected from the group consisting of La, Ce, Pr, Nd, Sm, Eu, Gd, Th, Dy, Ho, Er, Tm, Yb, Lu, wherein A is an element selected from the group consisting of Mg, Ca, Sr, Ba, wherein M is an element selected from the group consisting of Sc, Ti, V, Cr, Mn, Fe, Co, Ni, Cu, Zn, wherein M' is an element selected from the group consisting of Sc, Ti, V, Cr, Mn, Fe, Co, Ni, Cu, Zn) and wherein $0 \leq x \geq 0.4$, $0 \leq y \geq 0.4$, and $0 \leq z \geq 1$.

23. The apparatus of claim 20 wherein the electrical biasing source is selected from the group consisting of (i) a constant current source for holding a substantially constant current between the electrodes and (ii) a constant voltage source for holding a substantially constant voltage across the sensing device.

24. The apparatus of claim 20 wherein:
(i) the electrical biasing source comprises a constant current source that holds the current between the electrodes substantially constant, and
(ii) the sensing device is selected from materials that produce a change in resistance that is substantially proportional to the concentration of NO gas in the $NO_x$ gas while the sensing device is being electrically biased at the selected electrical bias.

25. The apparatus of claim 20 wherein:
(i) the electrical biasing source comprises a constant voltage source that holds the voltage across the sensing device constant; and
(ii) the sensing device is selected from materials that produce a change in resistance that is substantially proportional to the concentration of NO gas in the $NO_x$ gas while the sensing device is being electrically biased at the selected electrical bias.

26. The apparatus of claim 20 wherein:
(i) the electrical biasing source comprises a constant current source that holds the current between the electrodes substantially constant, and
(ii) the sensing device is selected from materials that produce a change in resistance that is proportional to the concentration of NO and $NO_2$ gas in the $NO_x$ gas while the sensing device is being electrically biased at the selected electrical bias.

27. The apparatus of claim 20 wherein:
(i) the electrical biasing source comprises a constant voltage source that holds the voltage between the electrodes substantially constant, and
(ii) the oxygen-ion conductor is selected from a material that produces a change in resistance that is substantially proportional to the concentration of NO and $NO_2$ gas in the $NO_x$ gas while the sensing device is being electrically biased at the selected electrical bias.

28. The apparatus of claim 20 wherein the composition of the first electrode is substantially identical to the composition of the second electrode.

29. The apparatus of claim 27 wherein both the first electrode and the second electrode are metal oxides.

* * * * *

UNITED STATES PATENT AND TRADEMARK OFFICE
CERTIFICATE OF CORRECTION

PATENT NO. : 7,678,329 B2  
APPLICATION NO. : 10/949854  
DATED : March 16, 2010  
INVENTOR(S) : Frederick C. Montgomery et al.

Page 1 of 1

It is certified that error appears in the above-identified patent and that said Letters Patent is hereby corrected as shown below:

Title Page, Item (73) Assignee should read as follows:

UT-Battelle, LLC  
One Bethel Valley Road  
4500N, MS-6258  
Oak Ridge, Tennessee 37831-6258

Title Page, Item (74) Attorney, Agent, or Firm should read as follows:

Luedeka, Neely & Graham, P.C.

Signed and Sealed this  
Third Day of May, 2011

David J. Kappos  
*Director of the United States Patent and Trademark Office*